US008580807B2

(12) United States Patent
Boyle et al.

(10) Patent No.: US 8,580,807 B2
(45) Date of Patent: Nov. 12, 2013

(54) BICYCLIC PIPERIDINE AND PIPERAZINE DERIVATIVES AS GPCR MODULATORS FOR THE TREATMENT OF OBESITY, DIABETES AND OTHER METABOLIC DISORDERS

(75) Inventors: Craig D. Boyle, Branchburg, NJ (US); Claire M. Lankin, High Bridge, NJ (US); Unmesh G. Shah, Green Brook, NJ (US); William J. Greenlee, Teaneck, NJ (US); Samuel Chackalamannil, Califon, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 10 days.

(21) Appl. No.: 13/260,673

(22) PCT Filed: Apr. 1, 2010

(86) PCT No.: PCT/US2010/029554
§ 371 (c)(1),
(2), (4) Date: Sep. 27, 2011

(87) PCT Pub. No.: WO2010/114957
PCT Pub. Date: Oct. 7, 2010

(65) Prior Publication Data
US 2012/0021976 A1  Jan. 26, 2012

Related U.S. Application Data

(60) Provisional application No. 61/166,414, filed on Apr. 3, 2009.

(51) Int. Cl.
*A01N 43/40* (2006.01)
*A61K 31/435* (2006.01)
*C07D 239/02* (2006.01)

(52) U.S. Cl.
USPC .......................... 514/277; 544/242; 546/112

(58) Field of Classification Search
USPC .......................... 546/112; 544/242; 514/277
See application file for complete search history.

(56) References Cited

U.S. PATENT DOCUMENTS 7,132,426 B2   11/2006  Jones et al.
2005/0070562 A1   3/2005  Jones et al.

FOREIGN PATENT DOCUMENTS

| EP | 1338651 B1 | 12/2006 |
|---|---|---|
| WO | 2004/065380 | 8/2004 |
| WO | 2004/076413 A2 | 9/2004 |
| WO | 2004/076413 A3 | 9/2004 |
| WO | 2005/121121 | 12/2005 |
| WO | 2006/076231 | 7/2006 |
| WO | 2008/025798 | 3/2008 |
| WO | 2008/137435 | 11/2008 |
| WO | 2010/075269 | 7/2010 |
| WO | 2011/062889 | 5/2011 |

OTHER PUBLICATIONS

Vogt et al., "Exploring structure-selectivity relationships of biogenic amine GPCR antagonists . . . ", Mol. Diversity (2008), vol. 12, pp. 25-40.
Fyfe et al., "New nonpeptide-binding GPCRs as target for diabetes . . . ", Annual Reports in Med. Chemistry (2007), vol. 42, pp. 129-145.
Soltanshahi et al., "Balancing focused combinatorial libraries . . . ", J. Comput. Aided Molecular Design (2006), vol. 20, pp. 529-538.
Int'l Search Report of PCT/US2010/029554, dated Jul. 23, 2010.

*Primary Examiner* — Paul V. Ward
(74) *Attorney, Agent, or Firm* — Anna L. Cocuzzo; Catherine D. Fitch

(57) ABSTRACT

The present invention relates to Bicyclic Piperidine and piperazine Derivatives, compositions comprising a Bicyclic Piperidine and piperazine Derivative, and methods of using the Bicyclic Piperidine and piperazine Derivatives for treating or preventing obesity, diabetes, a metabolic disorder, a cardiovascular disease or a disorder related to the activity of a GPCR in a patient.

17 Claims, No Drawings

BICYCLIC PIPERIDINE AND PIPERAZINE DERIVATIVES AS GPCR MODULATORS FOR THE TREATMENT OF OBESITY, DIABETES AND OTHER METABOLIC DISORDERS

FIELD OF THE INVENTION

The present invention relates to Bicyclic Piperidine and piperazine Derivatives, compositions comprising a Bicyclic Piperidine and piperazine Derivative, and methods of using the Bicyclic Piperidine and piperazine Derivatives for treating or preventing obesity, diabetes, a diabetic complication, a metabolic disorder, a cardiovascular disease or a disorder related to the activity of a G-Protein Coupled Receptor ("GPCR") in a patient.

BACKGROUND OF THE INVENTION

Although a number of receptor classes exist in humans, by far the most abundant and therapeutically relevant is represented by the GPCR class. It is estimated that there are some 100,000 genes within the human genome, and of these, approximately 2% or 2,000 genes, are estimated to code for GPCRs. Receptors, including GPCRs, for which the endogenous ligand has been identified are referred to as "known" receptors, while receptors for which the endogenous ligand has not been identified are referred to as "orphan" receptors. GPCRs represent an important area for the development of pharmaceutical products, as evidenced by the fact that pharmaceutical products have been developed from approximately 20 of the 100 known GPCRs. This distinction is not merely semantic, particularly in the case of GPCRs.

GPCRs share a common structural motif. All these receptors have seven sequences of between 22 to 24 hydrophobic amino acids that form seven alpha helices, each of which spans the membrane (each span is identified by number, i.e., transmembrane-1 (TM-1), transmembrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when an endogenous ligand binds with the receptor (often referred to as "activation" of the receptor), there is a change in the conformation of the intracellular region that allows for coupling between the intracellular region and an intracellular "G-protein." It has been reported that GPCRs are "promiscuous" with respect to G proteins, i.e., that a GPCR can interact with more than one G protein. See, Kenakin, T., *Life Sciences* 43, 1095 (1988). Although other G proteins exist, currently, Gq, Gs, Gi, and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein.

Under physiological conditions, GPCRs exist in the cell membrane in equilibrium between two different conformations: an "inactive" state and an "active" state. A receptor in an inactive state is unable to link to the intracellular signaling transduction pathway to produce a biological response. Changing the receptor conformation to the active state allows linkage to the transduction pathway (via the G-protein) and produces a biological response. A receptor can be stabilized in an active state by an endogenous ligand or a compound such as a drug.

Modulation of G-protein coupled receptors has been well-studied for controlling various metabolic disorders. Small molecule modulators of the receptor GPR119, a G-protein coupled-receptor described in, for example, GenBank (see, e.g., accession numbers XM.sub.-066873 and AY288416), have been shown to be useful for treating or preventing certain metabolic disorders. GPR119 is a G protein-coupled receptor that is selectively expressed on pancreatic beta cells. GPR119 activation leads to elevation of a level of intracellular cAMP, consistent with GPR119 being coupled to Gs. Agonists to GPR119 stimulate glucose-dependent insulin secretion in vitro and lower an elevated blood glucose level in vivo. See, e.g., International Publication Nos. WO 04/065380, WO 04/076413, and EP 1338651, the disclosure of each of which is herein incorporated by reference in its entirety.

U.S. Pat. No. 7,136,426 discloses pyrazolo[3,4-d]pyrimidine ethers and related compounds as modulators of the GPR119 receptor that are useful for the treatment of various metabolic-related disorders such as type I diabetes, type II diabetes, inadequate glucose tolerance, insulin resistance, hyperglycemia, hyperlipidemia, hypertriglyceridemia, hypercholesterolemia, dyslipidemia or syndrome X. The compounds are also reported as being useful for controlling weight gain, controlling food intake, and inducing satiety in mammals. The promising nature of these GPCR modulators indicates a need in the art for additional small molecule GPCR modulators with improved efficacy and safety profiles. This invention addresses that need.

SUMMARY OF THE INVENTION

In one aspect, the present invention provides compounds of Formula (I):

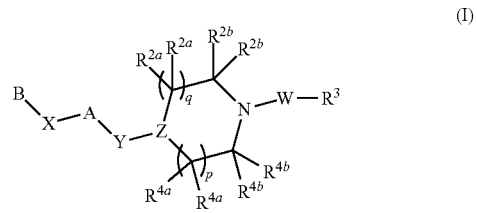

and pharmaceutically acceptable salts, solvates, esters, prodrugs and stereoisomers thereof, wherein:

A is aryl or -5- or 6-membered heteroaryl, wherein said aryl group or said -5- or 6-membered heteroaryl group can be optionally substituted with up to 4 groups, which can be the same or different, and are selected from alkyl, aryl, alkenyl, cycloalkyl, cycloalkenyl, haloalkyl, hydroxyalkyl, halo, —OH, —O-haloalkyl, —O-alkyl, —O-alkyl-OH, —O-alkyl-O-alkyl, —O-aryl, -alkylene-O-alkyl, —CN, —N($R^4$)$_2$, —C(O)H, —C(O)$R^4$, —C(O)O$R^4$, —C(O)N($R^4$)$_2$, —NHC(O)$R^4$, —NHS(O)$_m$$R^4$, —S(O)$_n$$R^4$ and —S(O)$_m$N($R^4$)$_2$;

B is aryl or heteroaryl, wherein said aryl group or said heteroaryl group can be the same or different, and are selected from alkyl, aryl, alkenyl, cycloalkyl, cycloalkenyl, haloalkyl, hydroxyalkyl, heteroaryl, halo, —OH, —O-haloalkyl, —O-alkyl, —O-aryl, -alkylene-O-alkyl, -alkylene-S(O)$_2$-alkyl, —CN, —N($R^4$)$_2$, —C(O)$R^4$, —C(O)O$R^4$, —C(O)N($R^4$)$_2$, —NHC(O)$R^4$, —NHS(O)$_m$$R^4$, —S(O)$_n$$R^4$ and —S(O)$_m$N($R^4$)$_2$, wherein said cycloalkyl or said heteroaryl substituent group can be unsubstituted or optionally substituted with $R^9$, and wherein when B is aryl, the aryl group can be optionally fused to a 4 to 7-membered cycloalkyl group or cycloalkanoyl group;

W is —C(O)O—, alkylene, —C(O)—, —C(O)—O—, —S(O)$_2$—, —S(O)$_2$—N($R^7$)— or —C(O)—N($R^7$)—;

X is —C($R^1$)$_2$—, —O—, —N($R^{10}$)— or —S—;

Y is a bond, alkylene, -(alkylene)$_t$-O-(alkylene)$_t$-, -(alkylene)$_t$-N($R^{12}$)-(alkylene)$_t$- or -(alkylene)$_t$-S-(alkylene)$_t$-;

Z is —N— or —C($R^7$)—, such that when Z is —N—, then group Y is joined to group Z via a carbon atom;

each occurrence of $R^1$ is independently H, alkyl, cycloalkyl, halo or —O$R^7$; wherein said alkyl group can be unsubstituted or optionally substituted with one or more of the following groups: —O-alkyl, —OH or —N($R^4$)$_2$; and wherein any two geminal $R^1$ groups, together with the common carbon atom to which they are attached, can join to form a spirocyclic 3- to 6-membered cycloalkyl group, a spirocyclic 3- to 6-membered heterocycloalkyl group or a spirocyclic 3- to 6-membered heterocycloalkenyl group; and wherein any two $R^1$ groups present on separate ring carbon atoms can join to form a cycloalkyl or heterocycloalkyl bridge; and wherein any particular $R^1$ group is —OH, then any other $R^1$ group attached to the same carbon atom must be other than halo or —O$R^7$;

each occurrence of $R^{2a}$ is H or alkyl, wherein: (i) any two $R^{2a}$ groups, together with the carbon atoms to which each are attached, can join to form a cycloalkyl or heterocycloalkyl group; (ii) an $R^{2a}$ group and an $R^{2b}$ group, together with the carbon atoms to which each are attached, can join to form a cycloalkyl or heterocycloalkyl group; or (iii) $R^7$ and an $R^{2a}$ group that is attached to a carbon atom adjacent to Z, together with the carbon atoms to which each are attached, can join to form a cycloalkyl or heterocycloalkyl group;

each occurrence of $R^{2b}$ is H or alkyl, wherein (i): any two $R^{2b}$ groups, together with the carbon atoms to which each are attached, can join to form a cycloalkyl or heterocycloalkyl group; or (ii) an $R^{2b}$ group and an $R^{2a}$ group, together with the carbon atoms to which each are attached, can join to form a cycloalkyl or heterocycloalkyl group;

$R^3$ is alkyl, alkenyl, alkynyl, haloalkyl, -alkylene-O-(alkylene)$_t$-aryl, alkylene-S-aryl, -alkylene-N($R^4$)C(O)O-alkyl, —CH(cycloalkyl)$_2$, —CH(heterocycloalkyl)$_2$, -(alkylene)$_t$-aryl, -(alkylene)$_t$-cycloalkyl, -(alkylene)$_t$-cycloalkenyl, -(alkylene)$_t$-heterocycloalkyl, -(alkylene)$_t$-heterocycloalkenyl or -(alkylene)$_t$-heteroaryl, wherein said aryl, cycloalkyl, cycloalkenyl, heterocycloalkyl, heterocycloalkenyl or heteroaryl groups can be unsubstituted or optionally substituted with $R^8$;

each occurrence of $R^4$ is H, alkyl, cycloalkyl or -(alkylene)$_t$-alkenyl, wherein said alkyl group can be optionally substituted with halo, —OH or —O-alkyl;

each occurrence of $R^{4a}$ is H or alkyl, wherein (i) any two $R^{4a}$ groups, together with the carbon atoms to which each are attached, can join to form a cycloalkyl or heterocycloalkyl group, (ii) an $R^{4a}$ group and an $R^{4b}$ group, together with the carbon atoms to which each are attached, can join to form a cycloalkyl or heterocycloalkyl group, or (iii) $R^7$ and an $R^{4a}$ group that is attached to a carbon atom adjacent to Z, together with the carbon atoms to which each are attached, can join to form a cycloalkyl or heterocycloalkyl group;

each occurrence of $R^{4b}$ is H or alkyl, wherein (i) any two $R^{4b}$ groups, together with the carbon atoms to which each are attached, can join to form a cycloalkyl or heterocycloalkyl group, or (ii) an $R^{4b}$ group and an $R^{4a}$ group, together with the carbon atoms to which each are attached, can join to form a cycloalkyl or heterocycloalkyl group;

$R^7$ is H or alkyl, or: (i) $R^7$ and an $R^{2a}$ group that is attached to a carbon atom adjacent to Z, together with the carbon atoms to which each are attached, can join to form a cycloalkyl or heterocycloalkyl group, or (ii) $R^7$ and an $R^{4a}$ group that is attached to a carbon atom adjacent to Z, together with the carbon atoms to which each are attached, can join to form a cycloalkyl or heterocycloalkyl group;

$R^8$ is aryl, heteroaryl, heterocycloalkyl, cycloalkenyl, cycloalkyl or heterocycloalkyl, any of which can be optionally substituted with $R^9$;

$R^9$ represents from 1 to 4 optional substituents, which can be the same or different, and which are selected from alkyl, alkenyl, alkynyl, halo, haloalkyl, —CN, —NO$_2$, —O-(alkylene)$_t$-$R^{13}$, —S-(alkylene)$_t$-$R^{13}$, —N($R^{13}$)-(alkylene)$_t$-$R^{13}$, -(alkylene)$_t$-$R^{13}$, —C(O)-(alkylene)$_t$-$R^{13}$, —C(O)O-(alkylene)$_t$-$R^{13}$, —N($R^7$)C(O)-(alkylene)$_t$-$R^{13}$, —C(O)N($R^7$)-(alkylene)$_t$-$R^{13}$, —OC(O)-(alkylene)$_t$-$R^{13}$, —N($R^7$)C(O)N($R^7$)-(alkylene)$_t$-$R^{13}$—N($R^7$)C(O)O-(alkylene)$_t$-$R^{13}$, —S(O)-(alkylene)$_t$-$R^{13}$ or —S(O)$_2$(alkylene)$_t$-$R^{13}$;

$R^{10}$ is H, alkyl, aryl, or —C(O)O$R^4$, wherein said alkyl group is unsubstituted or optionally substituted with —OH or —O-alkyl;

$R^{12}$ is H, alkyl or aryl;

each occurrence of $R^{13}$ is independently H, haloalkyl, aryl, cycloalkyl, cycloalkenyl, heterocycloalkyl, heterocycloalkenyl or heteroaryl;

each occurrence of m is independently 1 or 2;

each occurrence of n is independently 0, 1 or 2, such that the sum of n and m is an integer ranging from 0 to 4;

p is an integer ranging from 0 to 4;

q is an integer ranging from 0 to 4; and each occurrence of t is independently 0 or 1, such that (i) at least one of $R^{2a}$, $R^{2b}$, $R^{4a}$ or $R^{4b}$ and the carbon atom to which it is attached, must combine with a separate $R^{2a}$, $R^{2b}$, $R^{4a}$ or $R^{4b}$ group and the carbon atom to which it is attached, to form a cycloalkyl or heterocycloalkyl group, or (ii) $R^7$ and an $R^{2a}$ group that is attached to a carbon atom adjacent to Z, together with the carbon atoms to which each are attached, must combine to form a cycloalkyl or heterocycloalkyl group, or (iii) $R^7$ and an $R^{4a}$ group that is attached to a carbon atom adjacent to Z, together with the carbon atoms to which each are attached, must combine to form a cycloalkyl or heterocycloalkyl group.

The compounds of formula (I) and pharmaceutically acceptable salts, solvates, esters or prodrugs thereof (referred to collectively herein as the "Bicyclic Piperidine and piperazine Derivatives") can be useful for treating or preventing obesity, diabetes, a diabetic complication, metabolic syndrome, a cardiovascular disease or a disorder related to the activity of a GPCR (each being a "Condition") in a patient.

Also provided by the invention are methods for treating or preventing a Condition in a patient, comprising administering to the patient an effective amount of one or more Bicyclic Piperidine and piperazine Derivatives.

The present invention further provides compositions comprising an effective amount of one or more Bicyclic Piperidine and piperazine Derivatives or a pharmaceutically acceptable salt, solvate, ester, prodrug or stereoisomer thereof, and a pharmaceutically acceptable carrier. The compositions can be useful for treating or preventing a Condition in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides Bicyclic Piperidine and piperazine Derivatives of formula (I), compositions comprising one or more Bicyclic Piperidine and piperazine Derivatives, and methods of using the Bicyclic Piperidine and piperazine Derivatives for treating or preventing a Condition in a patient.

DEFINITIONS AND ABBREVIATIONS

As used above, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "obesity" as used herein, refers to a patient being overweight and having a body mass index (BMI) of 25 or greater. In one embodiment, an obese patient has a BMI of 25 or greater. In another embodiment, an obese patient has a BMI from 25 to 30. In another embodiment, an obese patient has a BMI greater than 30. In still another embodiment, an obese patient has a BMI greater than 40.

The term "obesity-related disorder" as used herein refers to: (i) disorders which result from a patient having a BMI of 25 or greater; and (ii) eating disorders and other disorders associated with excessive food intake. Non-limiting examples of an obesity-related disorder include edema, shortness of breath, sleep apnea, skin disorders and high blood pressure.

The term "metabolic syndrome" as used herein, refers to a set of risk factors that make a patient more susceptible to cardiovascular disease and/or type 2 diabetes. A patient is said to have metabolic syndrome if the patient simultaneously has three or more of the following five risk factors:
1) central/abdominal obesity as measured by a waist circumference of greater than 40 inches in a male and greater than 35 inches in a female;
2) a fasting triglyceride level of greater than or equal to 150 mg/dL;
3) an HDL cholesterol level in a male of less than 40 mg/dL or in a female of less than 50 mg/dL;
4) blood pressure greater than or equal to 130/85 mm Hg; and
5) a fasting glucose level of greater than or equal to 110 mg/dL.

The term "effective amount" as used herein, refers to an amount of Bicyclic Piperidine and piperazine Derivative and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

The term "alkyl," as used herein, refers to an aliphatic hydrocarbon group which may be straight or branched and which contains from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, -D-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)ON and —C(O)O-alkyl. Unless otherwise indicated, an alkyl group is unsubstituted. In one embodiment, an alkyl group is linear. In another embodiment, an alkyl group is branched.

The term "alkenyl," as used herein, refers to an aliphatic hydrocarbon group containing at least one carbon-carbon double bond and which may be straight or branched and contains from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. Unless otherwise indicated, an alkenyl group is unsubstituted.

The term "alkynyl," as used herein, refers to an aliphatic hydrocarbon group containing at least one carbon-carbon triple bond and which may be straight or branched and contains from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-β-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. Unless otherwise indicated, an aryl group is unsubstituted. In one embodiment, an aryl group is phenyl.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 5 to about 7 ring atoms. The term "cycloalkyl" also encompasses a cycloalkyl group, as defined above, that is fused to an aryl (e.g., benzene) or heteroaryl ring. A cycloalkyl group can be joined via a ring carbon or ring nitrogen atom. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

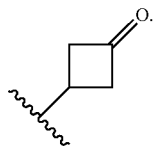

The term "cycloalkenyl," as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. Unless otherwise indicated, a cycloalkenyl group is unsubstituted. In one embodiment, a cycloalkenyl group is a 5-membered cycloalkenyl. In another embodiment, a cycloalkenyl group is a 6-membered cycloalkenyl.

The term "heteroalkylene," as used herein, refers to group having the formula -alkylene-X-alkylene- wherein X is —O—, —S— or —NH—. Non-limiting examples of heteroalkylene groups include —CH$_2$OCH$_2$—, —CH$_2$SCH$_2$—, —CH$_2$N(H)CH$_2$—, —CH$_2$OCH$_2$CH$_2$—, —CH$_2$SCH$_2$CH$_2$— and —CH$_2$N(H)CH$_2$CH$_2$—. In one embodiment, a heteroalkylene group has from 2 to about 6 carbon atoms. In another embodiment, a heteroalkylene group has from 2 to about 3 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, that is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. Unless otherwise indicated, a heteroaryl group is unsubstituted. In one embodiment, a heteroaryl group is a 5-membered heteroaryl. In another embodiment, a heteroaryl group is a 6-membered heteroaryl.

The term "heterocycloalkyl," as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. A heterocycloalkyl group can be joined via a ring carbon or ring nitrogen atom. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, that is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone and the like, and all isomers thereof. A ring carbon atom of a heterocycloalkyl group may be functionalized as a carbonyl group. An illustrative example of such a heterocycloalkyl group is pyrrolidonyl:

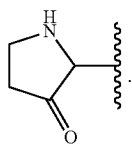

Unless otherwise indicated, a heterocycloalkyl group is unsubstituted. In one embodiment, a heterocycloalkyl group is a 5-membered heterocycloalkyl. In another embodiment, a heterocycloalkyl group is a 6-membered heterocycloalkyl.

The term "heterocycloalkenyl," as used herein, refers to a heterocycloalkyl group, as defined above, wherein the heterocycloalkyl group contains from 3 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 5 to 10 ring atoms. In another embodiment, a heterocycloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocycloalkenyl group may be functionalized as a carbonyl group. Unless otherwise indicated, a heterocycloalkenyl group is unsubstituted. In one embodiment, a heterocycloalkenyl group is a 5-membered heterocycloalkenyl. In another embodiment, a heterocycloalkenyl group is a 6-membered heterocycloalkenyl.

It should also be noted that tautomeric forms such as, for example, the moieties:

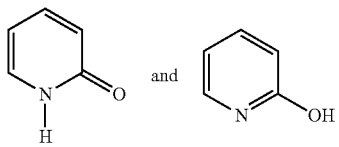 [SMILES: O=c1cccc[nH]1 ; Oc1ccccn1]

are considered equivalent in certain embodiments of this invention.

The term "ring system substituent," as used herein, refers to a substituent group attached to an aromatic or non-aromatic ring system which, for example, replaces an available hydrogen atom on the ring system. Ring system substituents may be the same or different, each being independently selected from the group consisting of alkyl, alkenyl, alkynyl, aryl, heteroaryl, -alkyl-aryl, -aryl-alkyl, -alkylene-heteroaryl, -alkenylene-heteroaryl, -alkynylene-heteroaryl, hydroxy, hydroxyalkyl, haloalkyl, —O-alkyl, —O-haloalkyl, -alkylene-O-alkyl, —O-aryl, aralkoxy, acyl, aroyl, halo, nitro, cyano, carboxy, —C(O)O-alkyl, —C(O)O-aryl, —C(O)O-alkelene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NS(O)$_2$— and —S(O)$_2$NY$_1$Y$_2$, wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

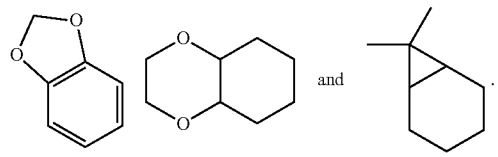

"Halo" means —F, —Cl, —Br or —I. In one embodiment, halo refers to —F, —Cl or —Br.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "purified", "in purified form" or "in isolated and purified form" for a compound refers to the physical state of the compound after being isolated from a synthetic process (e.g. from a reaction mixture), or natural source or combination thereof. Thus, the term "purified", "in purified form" or "in isolated and purified form" for a compound refers to the physical state of the compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a Bicyclic Piperidine and piperazine Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a Bicyclic Piperidine and piperazine Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di$(C_1$-$C_2)$alkylcarbamoyl-$(C_1$-$C_2)$alkyl and piperidino-, pyrrolidino- or morpholino $(C_2$-$C_3)$alkyl, and the like.

Similarly, if a Bicyclic Piperidine and piperazine Derivative contains an alcohol functional group, a prodrug can be formed by the replacement of the hydrogen atom of the alcohol group with a group such as, for example, $(C_1-C_6)$alkanoyloxymethyl, 1-(($C_1$-$C_6$)alkanoyloxy)ethyl, 1-methyl-1-(($C_1$-$C_6$)alkanoyloxy)ethyl, $(C_1$-$C_6)$alkoxycarbonyloxymethyl, N—$(C_1$-$C_6)$alkoxycarbonylaminomethyl, succinoyl, $(C_1$-$C_6)$alkanoyl, α-amino$(C_1$-$C_4)$alkyl, α-amino$(C_1$-$C_4)$alkylene-aryl, arylacyl and α-aminoacyl, or α-aminoacyl-α-aminoacyl, where each α-aminoacyl group is independently selected from the naturally occurring L-amino acids, P(O)$(OH)_2$, —P(O)(O$(C_1$-$C_6$)alkyl$)_2$ or glycosyl (the radical resulting from the removal of a hydroxyl group of the hemiacetal form of a carbohydrate), and the like.

If a Bicyclic Piperidine and piperazine Derivative incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$)alkyl and Y$^3$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The Bicyclic Piperidine and piperazine Derivatives can form salts which are also within the scope of this invention. Reference to a Bicyclic Piperidine and piperazine Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Bicyclic Piperidine and piperazine Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the compounds of the Formula (I) may be formed, for example, by reacting a Bicyclic Piperidine and piperazine Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (for example, methyl, ethyl, n-propyl, isopropyl, t-butyl, sec-butyl or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or —O—$C_{1-4}$alkyl or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Bicyclic Piperidine and piperazine Derivatives may be atropisomers (e.g., substituted biaryls) and are considered as part of this invention. Enantiomers CaO also be separated by use of chiral HPLC column.

It is also possible that the Bicyclic Piperidine and piperazine Derivatives may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a Bicyclic Piperidine and piperazine Derivative incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Pyrimidine Derivatives (e.g., those labeled with $^{3}H$ and $^{14}C$) are useful in compound and/or substrate tissue distribution assays. In one embodiment, ritiated (i.e., $^{3}H$) and carbon-14 (i.e., $^{14}C$) isotopes are employed for their ease of preparation and detectability. In another embodiment, substitution with heavier isotopes such as deuterium (i.e., $^{2}H$) may afford certain therapeutic advantages resulting from greater metabolic stability (e.g., increased in vivo half-life or reduced dosage requirements). Isotopically labelled compounds of Formula (I) can generally be prepared by following procedures analogous to those disclosed in the Schemes and/or in the Examples herein below, by substituting an appropriate isotopically labelled reagent for a non-isotopically labelled reagent.

Polymorphic forms of the Bicyclic Piperidine and piperazine Derivatives, and of the salts, solvates, hydrates, esters and prodrugs of the Bicyclic Piperidine and piperazine Derivatives, are intended to be included in the present invention.

The following abbreviations are used below and have the following meanings:
BINAP is 2,2'-bis(diphenylphosphino)-1,1'-binaphthyl, Boc or BOC is N-tert-butoxycarbonyl, (Boc)$_2$O is N-tert-butoxycarbonyl anhydride, BuLi is n-butyllithium, t-butyl is tertiary butyl, t-BuOH is tertiary butanol, t-BuOK is potassium tert-butoxide, dba is dibenzylidene acetone, DCM is dichloromethane, DIEA is diisopropylethylamine, DMEM is Dulbecco's modified eagle medium, DMF is N,N-dimethylformamide, DMSO is dimethylsulfoxide, EtOAc is ethyl acetate, EtOH is ethanol, Et$_3$N is triethylamine, LAH is lithium aluminum hydride, LCMS is liquid chromatography mass spectrometry, MeOH is methanol, NaBH(OAc)$_3$ is sodium triacetoxyborohydride, Nat-BuO or NaOt-Bu is sodium tert-butoxide, NMR is nuclear magnetic resonance, Pd/C is palladium on carbon, Pd(PPh$_3$) is tetrakis triphenylphosphine palladium, Ph is phenyl, THF is tetrahydrofuran, TLC is thin-layer chromatography, TMSOTf is trimethylsilyl trifluoromethanesulfonate and XPhos is 2-dicyclohexylphosphino-2',4',6'-triisopropylbiphenyl.

The Bicyclic Piperidine and piperazine Derivatives of Formula (I)

The present invention provides Bicyclic Piperidine and piperazine Derivatives of Formula (I):

(I)

and pharmaceutically acceptable salts, solvates, esters, prodrugs and stereoisomers thereof, wherein A, B, W, X, Y, Z, R$^{2a}$, R$^{2b}$, R$^3$, R$^{4a}$, p and q are defined above for the compounds of formula (I).

In one embodiment, A is aryl.
In another embodiment, A is 5 or 6-membered heteroaryl.
In another embodiment, A is phenyl.
In still another embodiment, A is pyrimidinyl.
In one embodiment, -A- is:

wherein Q is H, halo, cyaloalkyl, alkyl or —O-alkyl.

In another embodiment, -A- is:

wherein Q is H, halo, alkyl or —O-alkyl.
In another embodiment, -A- is:

wherein Q is H, F, methyl or —OCH$_3$.
In still another embodiment, A is:

In one embodiment, A is pyridyl.
In another embodiment, A is:

wherein Q is H, alkyl, halo, cycloalkyl or —O-alkyl.
In another embodiment, A is:

wherein Q is H, methyl, cyclopropyl, F or methoxy.
In still another embodiment, A is:

wherein Q is F or methoxy.
In one embodiment, B is aryl.
In another embodiment, B is heteroaryl.
In another embodiment, B is 5 or 6-membered heteroaryl.

In another embodiment, B is phenyl.

In still another embodiment, B is pyrimidinyl.

In another embodiment, B is pyridyl.

In one embodiment, B is phenyl, which is unsubstituted or optionally substituted with up to 3 groups, each independently selected from alkyl, —CN, —S(O)₂-alkyl, —S(O)₂-cycloalkyl, heteroaryl and halo.

In another embodiment, B is phenyl, which is unsubstituted or optionally substituted with up to 3 groups, each independently selected from —CN, —S(O)₂-alkyl and halo.

In one embodiment, B is:

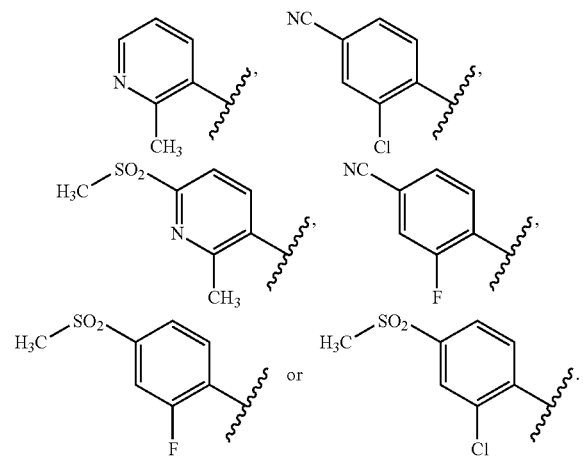

In another embodiment, B is:

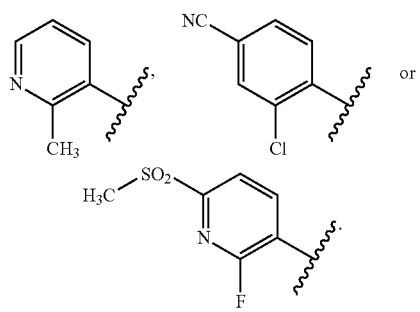

In one embodiment, A and B are each independently aryl or 5- or 6-membered heteroaryl.

In another embodiment, A and B are each independently phenyl or 5- or 6-membered heteroaryl.

In another embodiment, A and B are each independently phenyl or pyridyl.

In another embodiment, A and B are each independently phenyl, pyridyl or pyrimidinyl.

In one embodiment, A and B are each independently heteroaryl.

In another embodiment, A and B are each independently a 5 or 6-membered heteroaryl.

In another embodiment, A is a 5 or 6-membered heteroaryl and B is pyridyl.

In one embodiment, A is 5 or 6-membered heteroaryl and B is phenyl.

In another embodiment, A is pyrimidinyl and B is phenyl or pyridyl.

In another embodiment, A is pyrimidinyl and B is phenyl.

In still another embodiment, A is pyrimidinyl and B is pyridyl.

In another embodiment, A and B are each independently a 5 or 6-membered heteroaryl, each of which is unsubstituted or optionally substituted with one substituent, independently selected from alkyl, —CN, —S(O)₂-alkyl, —S(O)₂-cycloalkyl, heteroaryl and halo.

In yet another embodiment, A and B are each independently selected from phenyl, pyridyl and pyrimidinyl, each of which is unsubstituted or optionally substituted with one substituent, independently selected from alkyl, —CN, —S(O)₂-alkyl, —S(O)₂-cycloalkyl, heteroaryl and halo.

In another embodiment, A and B are each independently selected from phenyl, pyridyl and pyrimidinyl, each of which is unsubstituted or optionally substituted with one or more substituents, each independently selected from methyl, triazolyl, —CN, —Cl, —F, —S(O)₂CH₃ or —S(O)₂-cyclopropyl.

In one embodiment, B is phenyl which is optionally substituted with up to 3 groups, each independently selected from alkyl, —CN, —S(O)₂-alkyl, —S(O)₂-cycloalkyl, heteroaryl and halo; and A is:

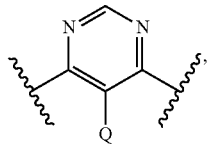

wherein Q is H, halo, alkyl or —O-alkyl.

In another embodiment, B is phenyl which is optionally substituted with up to 3 groups, each independently selected from methyl, triazolyl, —ON, —Cl, —F, —S(O)₂CH₃ and —S(O)₂-cyclopropyl; and A is:

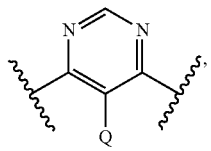

wherein Q is H, F, methyl or methoxy.

In another embodiment, B is pyridyl and A is:

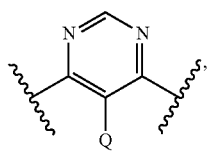

wherein Q is H, halo, alkyl or —O-alkyl.

In one embodiment, A is:

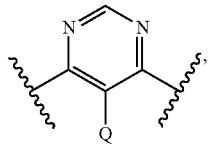

wherein Q is H, halo, alkyl or —O-alkyl, and B is aryl or heteroaryl.

In another embodiment, A is:

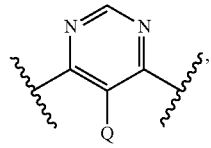

wherein Q is H, F, methyl or methoxy, and B is aryl or heteroaryl.

In another embodiment, A is:

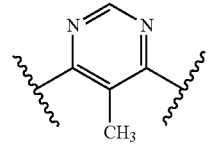

and B is aryl or heteroaryl.

In another embodiment, A is:

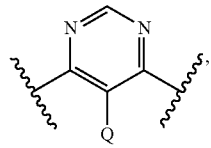

wherein Q is H, halo, alkyl or —O-alkyl; and B is heteroaryl.

In another embodiment, A is:

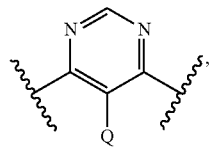

wherein Q is H, halo, alkyl or —O-alkyl; and B is pyridyl.

In another embodiment, A is:

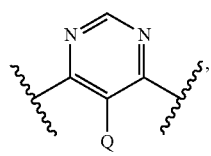

wherein is H, halo, alkyl or —O-alkyl; and B is:

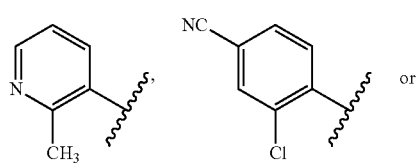

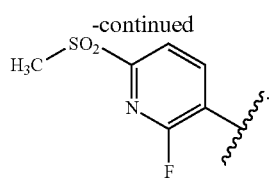

In another embodiment, A is:

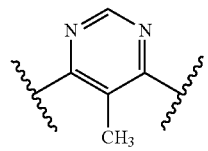 [SMILES: *c1ncnc(*)c1C]

and B is:

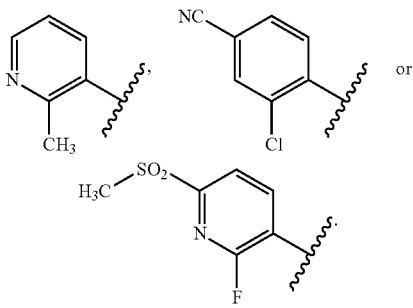

In one embodiment, A is 6-membered heteroaryl and B is:

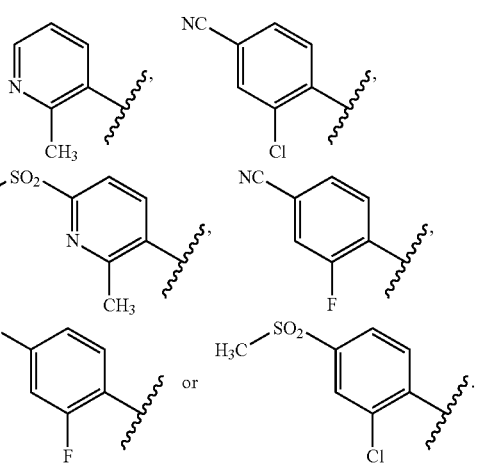

In another embodiment, A is 6-membered heteroaryl and B is:

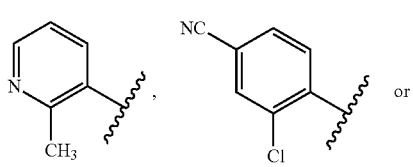

-continued
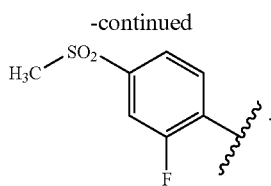
In one embodiment, A is:
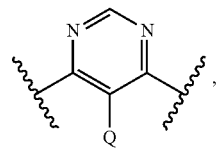
wherein Q is H, halo, alkyl or —O-alkyl, and B is
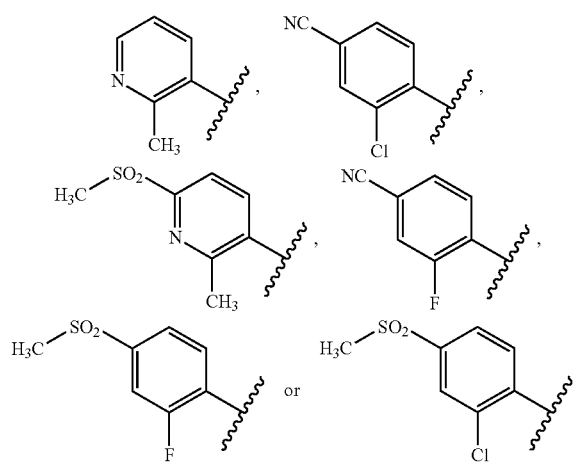
In another embodiment, A is:
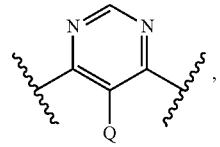
wherein Q is H, F, methyl or methoxy, and B is
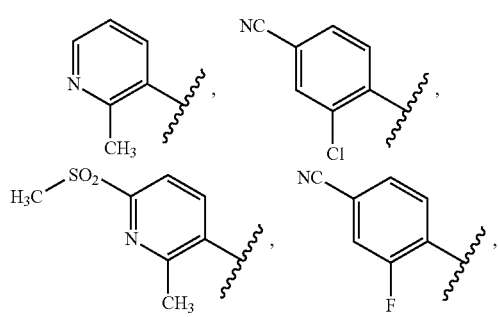
-continued
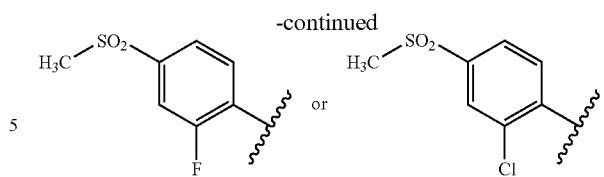
In another embodiment, A is:
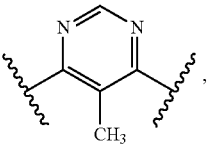
and B is
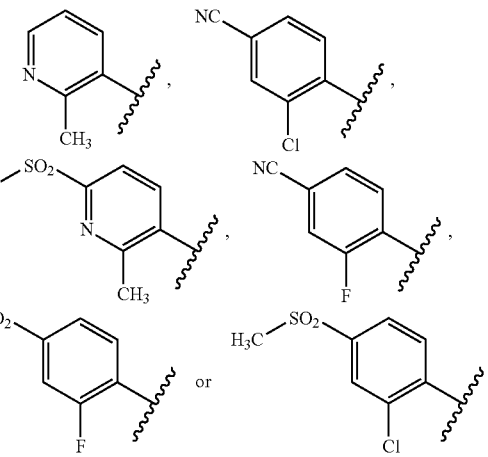
In still another embodiment, A is:
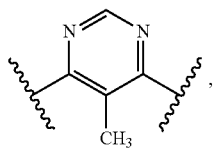
and B is
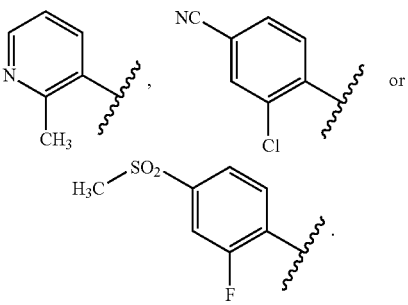
In one embodiment, W is a bond.
In another embodiment, W is —C(O)—.

In another embodiment, W is —C(O)O—.
In yet another embodiment, W is —S(O)$_2$—.
In another embodiment, W is —S(O)$_2$N(R$^7$)—.
In a further embodiment, W is —C(O)N(R$^7$)—.
In one embodiment, X is —C(R$^1$)$_2$—.
In another embodiment, X is —O—.
In another embodiment, X is —S—.
In yet another embodiment, X is —N(R$^{10}$)—.
In another embodiment, X is —NH—.
In one embodiment, Y is a bond.
In another embodiment, Y is -alkylene-.
In another embodiment, Y is -(alkylene)$_t$-O-(alkylene)$_t$-.
In still another embodiment, Y is -(alkylene)$_t$-N(R$^{12}$)-(alkylene)$_t$-.
In another embodiment, Y is -(alkylene)$_t$-S-(alkylene)$_t$-.
In yet another embodiment, Y is —O—.
In another embodiment, Y is —NH—.
In a further embodiment, Y is —O-alkylene-.
In another embodiment, Y is —OCH$_2$—.
In a further embodiment, X and Y are each independently —O— or —NH—.
In one embodiment, Z is —N—.
In another embodiment, Z is —C(R$^7$)—.
In another embodiment, Z is —CH—.
In one embodiment, each occurrence of R$^{2a}$ is H.
In another embodiment, each occurrence of R$^{2b}$ is H.
In another embodiment, each occurrence of R$^{2a}$ and R$^{2b}$ is H.
In one embodiment, two geminal R$^{2a}$ groups, together with the common carbon atom to which each are attached, combine to form a cycloalkyl group.
In another embodiment, two geminal R$^{2a}$ groups, together with the common carbon atom to which each are attached, combine to form a heterocycloalkyl group.
In another embodiment, two geminal R$^{2a}$ groups, together with the common carbon atom to which each are attached, combine to form a cyclopropyl group.
In still another embodiment, two geminal R$^{2a}$ groups, together with the common carbon atom to which each are attached, combine to form a cyclobutyl group.
In another embodiment, two geminal R$^{2a}$ groups, together with the common carbon atom to which each are attached, combine to form a cyclopentyl group.
In yet another embodiment, two geminal R$^{2a}$ groups, together with the common carbon atom to which each are attached, combine to form a cyclohexyl group.
In one embodiment, two geminal R$^{2b}$ groups, together with the common carbon atom to which each are attached, combine to form a cycloalkyl group.
In another embodiment, two geminal R$^{2b}$ groups, together with the common carbon atom to which each are attached, combine to form a heterocycloalkyl group.
In another embodiment, two geminal R$^{2b}$ groups, together with the common carbon atom to which each are attached, combine to form a cyclopropyl group.
In still another embodiment, two geminal R$^{2b}$ groups, together with the common carbon atom to which each are attached, combine to form a cyclobutyl group.
In another embodiment, two geminal R$^{2b}$ groups, together with the common carbon atom to which each are attached, combine to form a cyclopentyl group.

In yet another embodiment, two geminal R$^{2b}$ groups, together with the common carbon atom to which each are attached, combine to form a cyclohexyl group.
In one embodiment, an R$^{2a}$ group and an R$^{2b}$ group, together with the carbon atoms to which they are attached, combine to form a cycloalkyl group.
In another embodiment, an R$^{2a}$ group and an R$^{2b}$ group, together with the carbon atoms to which they are attached, combine to form a heterocycloalkyl group.
In yet another embodiment, an R$^{2a}$ group and an R$^{2b}$ group, together with the carbon atoms to which they are attached, combine to form a cyclopentyl group.
In another embodiment, an R$^{2a}$ group and an R$^{2b}$ group, together with the carbon atoms to which they are attached, combine to form a cyclohexyl group.
In a further embodiment, an R$^{2a}$ group and an R$^{2b}$ group, together with the carbon atoms to which they are attached, combine to form a cyclobutyl group.
In one embodiment, R$^3$ is alkyl.
In another embodiment, R$^3$ is a linear alkyl group.
In another embodiment, R$^3$ is a branched alkyl group.
In still another embodiment, R$^3$ is methyl.
In another embodiment, R$^3$ is ethyl.
In another embodiment, R$^3$ is isopropyl or t-butyl.
In another embodiment, R$^3$ is isopropyl.
In a further embodiment, R$^3$ is t-butyl.
In another embodiment, R$^3$ is alkenyl.
In another embodiment, R$^3$ is alkynyl.
In yet another embodiment, R$^3$ is haloalkyl.
In one embodiment, R$^3$ is cycloalkyl.
In another embodiment, R$^3$ is cyclopropyl.
In another embodiment, R$^3$ is cyclopropyl, substituted with a methyl group.
In another embodiment, R$^3$ is cyclobutyl.
In still another embodiment, R$^3$ is cyclopentyl.
In another embodiment, R$^3$ is cyclohexyl.
In one embodiment, R$^3$ is alkyl or cycloalkyl.
In one embodiment, R$^3$ is aryl.
In another embodiment, R$^3$ is phenyl.
In another embodiment, R$^3$ is phenyl, optionally substituted with halo.
In one embodiment, R$^3$ is heteroaryl.
In another embodiment, R$^3$ is 5-membered heteroaryl.
In another embodiment, R$^3$ is 6-membered heteroaryl.
In another embodiment, R$^3$ is 4-fluorophenyl, ethyl, t-butyl, isopropyl, —CH$_2$OCH$_3$, —CH$_2$OCH$_2$CH(CH$_3$)$_2$, —CH$_2$OCH$_2$CH$_2$CH(CH$_3$)$_2$ or —CH$_2$O-(4-methyl-2-pyridyl).
In another embodiment, R$^3$ is -alkylene-aryl.
In a further embodiment, R$^3$ is benzyl.
In one embodiment, each occurrence of R$^{4a}$ is H.
In another embodiment, each occurrence of R$^{4b}$ is H.
In another embodiment, each occurrence of R$^{4a}$ and R$^{4b}$ is H.
In one embodiment, each occurrence of R$^{2b}$ and R$^{4b}$ is H.
In another embodiment, each occurrence of R$^{2a}$, R$^{2b}$ and R$^{4b}$ is H.
In one embodiment, an R$^{2a}$ group and an R$^{4a}$ group join to form a bond between the carbon atoms that each are attached to.
In one embodiment, each occurrence of R$^{2a}$ and R$^{2b}$ is H, and both R$^{4a}$ groups, together with the common carbon atom to which they are attached, combine to form a cycloalkyl group.

In another embodiment, each occurrence of $R^{2a}$ and $R^{2b}$ is H, and both $R^{4a}$ groups, together with the common carbon atom to which they are attached, combine to form a heterocycloalkyl group.

In another embodiment, each occurrence of $R^{2a}$ and $R^{2b}$ is H, and both $R^{4a}$ groups, together with the common carbon atom to which they are attached, combine to form a cyclopropyl group.

In one embodiment, p is 0.
In another embodiment, p is 1.
In another embodiment, p is 2.
In one embodiment, q is 0.
In another embodiment, q is 1.
In another embodiment, q is 2.
In one embodiment, p and q are each 1.
In one embodiment, W is —C(O)O— and Z is —N—.
In another embodiment, W is —C(O)O— and Z is —CH—.
In one embodiment, W is —C(O)O—, Z is —CH— and X is —O—.
In another embodiment, W is —C(O)O—, Z is —CH—, and X is —NH—.
In one embodiment, W is —C(O)O— and $R^3$ is alkyl.
In another embodiment, Z is —CH— and $R^3$ is alkyl.
In another embodiment, W is —C(O)O— and $R^3$ is isopropyl or t-butyl.
In another embodiment, W is —C(O)O— and $R^3$ is isopropyl.
In still another embodiment, W is —C(O)O— and $R^3$ is t-butyl.
In one embodiment, X is —O— and A is pyrimidinyl.
In another embodiment, X is —NH— and A is pyrimidinyl.
In another embodiment, Y is —O— and A is pyrimidinyl.
In still another embodiment, Y is —NH— and A is pyrimidinyl.

In one embodiment, X is O— and -A- is:

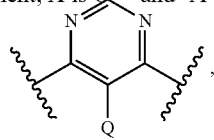

wherein Q is H, halo, alkyl or —O-alkyl.

In another embodiment, X is —NH— and -A- is:

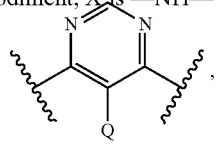

wherein Q is H, halo, alkyl or —O-alkyl.

In another embodiment, X is O— and -A- is:

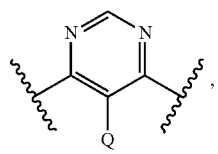

wherein Q is H, F, methyl or methoxy.

In still another embodiment, X is —NH— and -A- is:

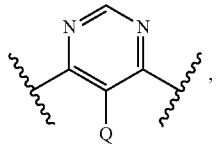

wherein Q is H, F, methyl or methoxy.

In one embodiment, X is —O—, Y is —O—, and -A- is:

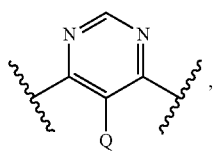

wherein Q is H, halo, alkyl or —O-alkyl.

In another embodiment, X is —NH—, Y is —O—, and -A- is:

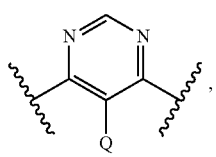

wherein Q is H, halo, alkyl or —O-alkyl.

In another embodiment, X is —O—, Y is —NH—, and -A- is:

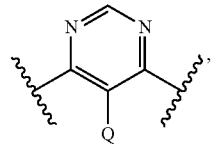

wherein Q is H, F, methyl or methoxy.

In still another embodiment, X is —NH—, Y is —NH—, and -A- is:

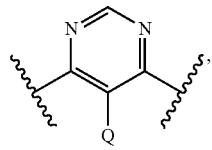

wherein Q is H, F, methyl or methoxy.

In one embodiment, X is —O— and B is phenyl or pyridyl.
In still another embodiment, X is —NH— and B is phenyl or pyridyl.

In one embodiment, X is —O— and B is:

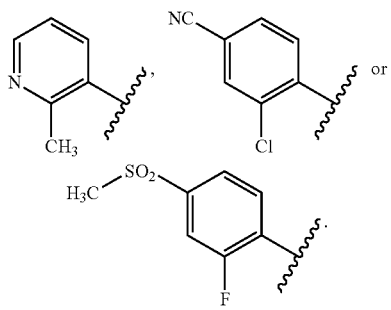

In still another embodiment, X is —NH— and B is:

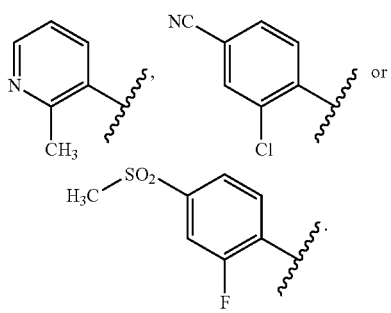

In one embodiment, X is —O—, Y is —O—, A is pyrimidinyl and B is pyridyl.
In another embodiment, X is —NH—, Y is —O—, A is pyrimidinyl and B is pyridyl.
In one embodiment, X is —O—, Y is —NH—, A is pyrimidinyl and B is pyridyl.
In another embodiment, X is —NH—, Y is —NH—, A is pyrimidinyl and B is pyridyl.
In one embodiment, X is —O—, Y is —O—, A is pyrimidinyl and B is phenyl.
In another embodiment, X is —NH—, Y is —O—, A is pyrimidinyl and B is phenyl.
In one embodiment, X is —O—, Y is —NH—, A is pyrimidinyl and B is phenyl.
In another embodiment, X is —NH—, Y is —NH—, A is pyrimidinyl and B is phenyl.
In one embodiment, X is —O—, Y is —O—, A is pyrimidinyl and B is phenyl, both of which are unsubstituted or optionally substituted with up to 3 groups, each independently selected from alkyl, —CN, —S(O)$_2$-alkyl, —S(O)$_2$-cycloalkyl, and halo.
In another embodiment, X is —NH—, Y is —O—, -, A is pyrimidinyl and B is phenyl, both of which are unsubstituted or optionally substituted with up to 3 groups, each independently selected from alkyl, —CN, —S(O)$_2$-alkyl, —S(O)$_2$-cycloalkyl, and halo.
In another embodiment, X is —NH—, Y is —NH—, -, A is pyrimidinyl and B is phenyl, both of which are unsubstituted or optionally substituted with up to 3 groups, each independently selected from alkyl, —CN, —S(O)$_2$-alkyl, —S(O)$_2$-cycloalkyl, and halo.
In still another embodiment, X is —NH—, Y is —NH—, -, A is pyrimidinyl and B is phenyl, both of which are unsubstituted or optionally substituted with up to 3 groups, each independently selected from alkyl, —CN, —S(O)$_2$-alkyl, —S(O)$_2$-cycloalkyl, and halo.

In one embodiment, Y is —O— and the group B—X-A- is:

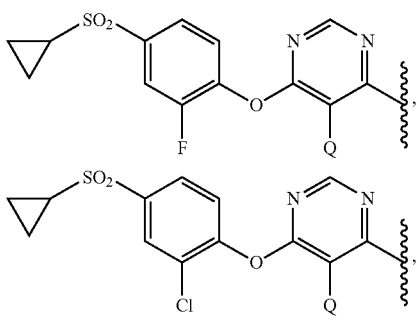

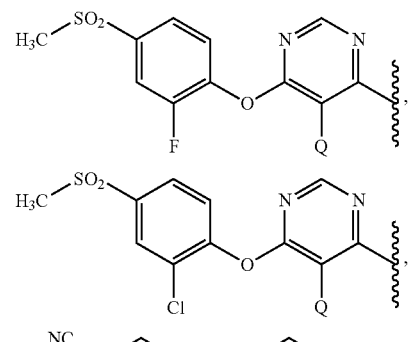

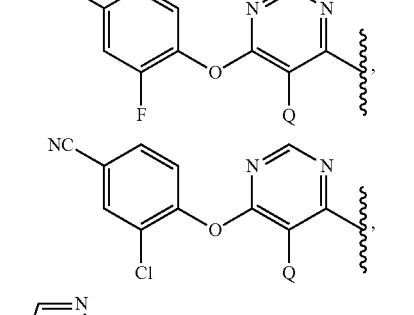

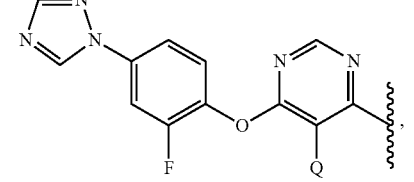

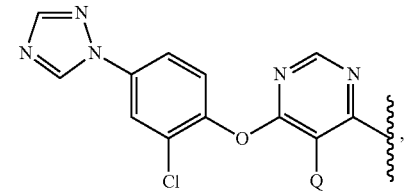

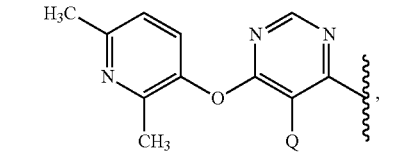

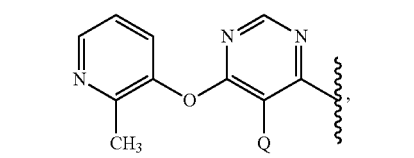

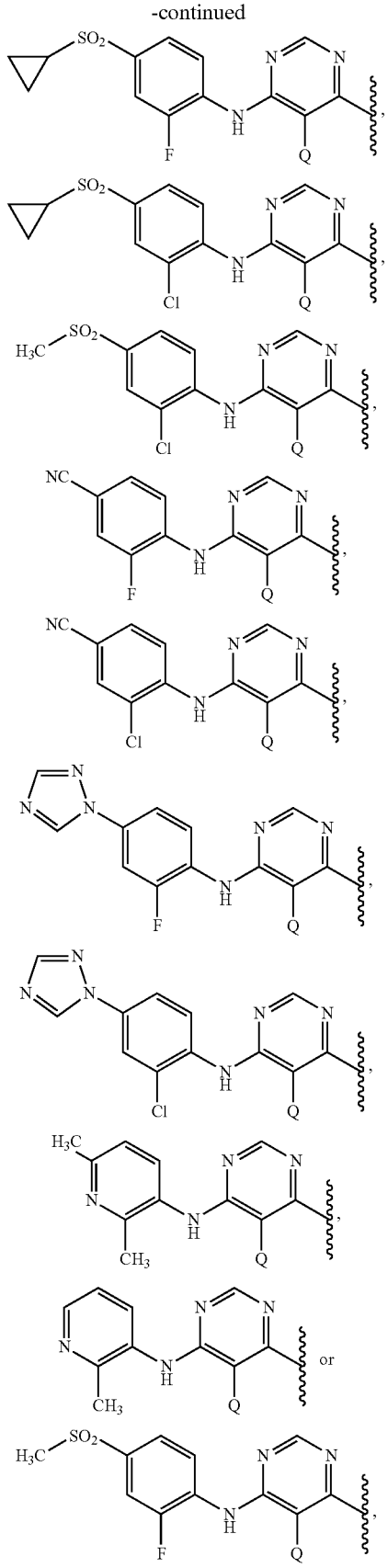
wherein Q is H, halo, alkyl or —O-alkyl.
In another embodiment, Y is —NH— and the group B—X-A- is:
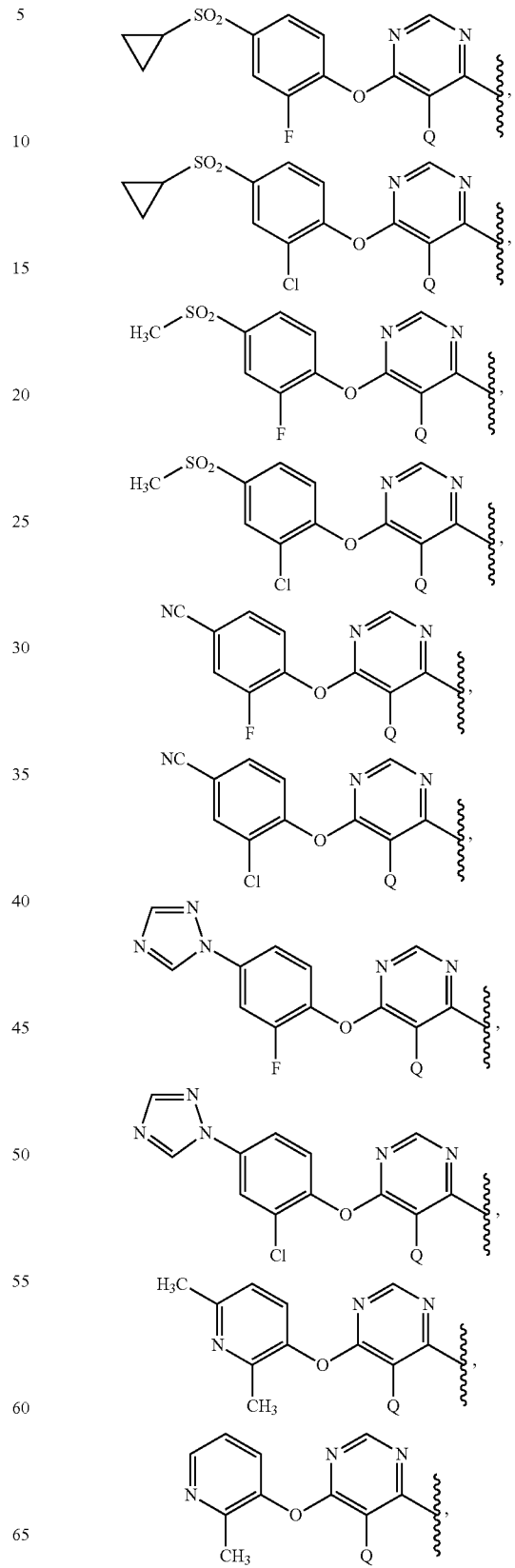

-continued
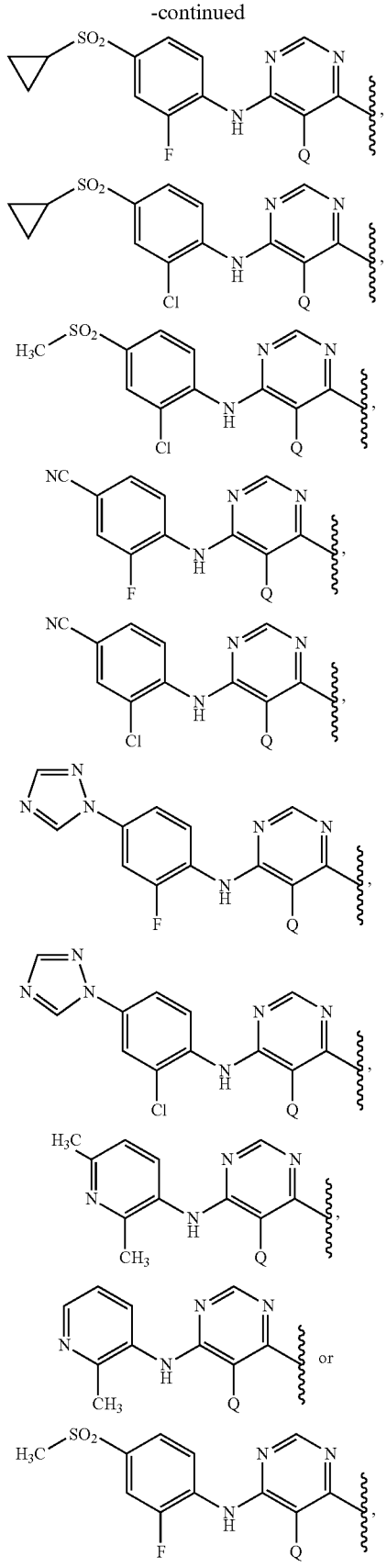
wherein Q is H, halo, alkyl or —O-alkyl.
In another embodiment, Y is —O— and the group B—X-A- is:
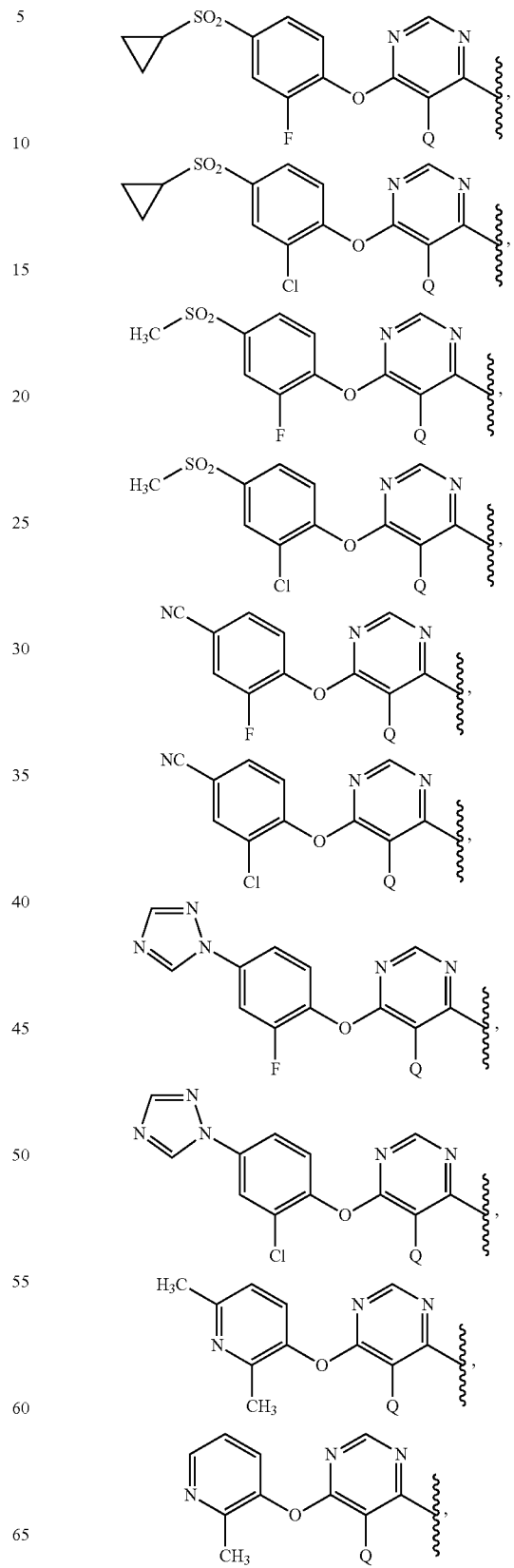

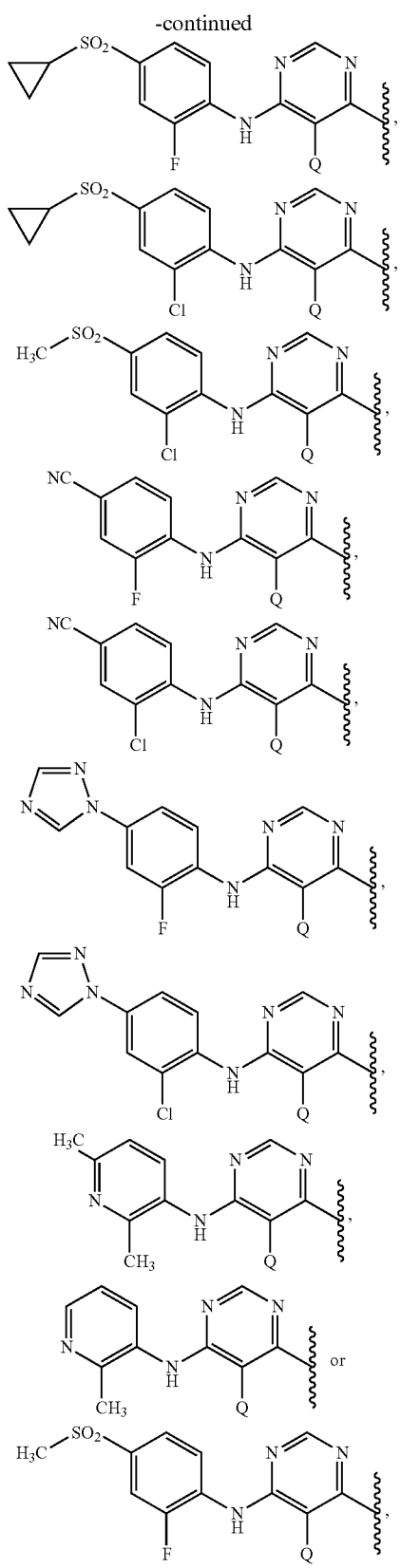
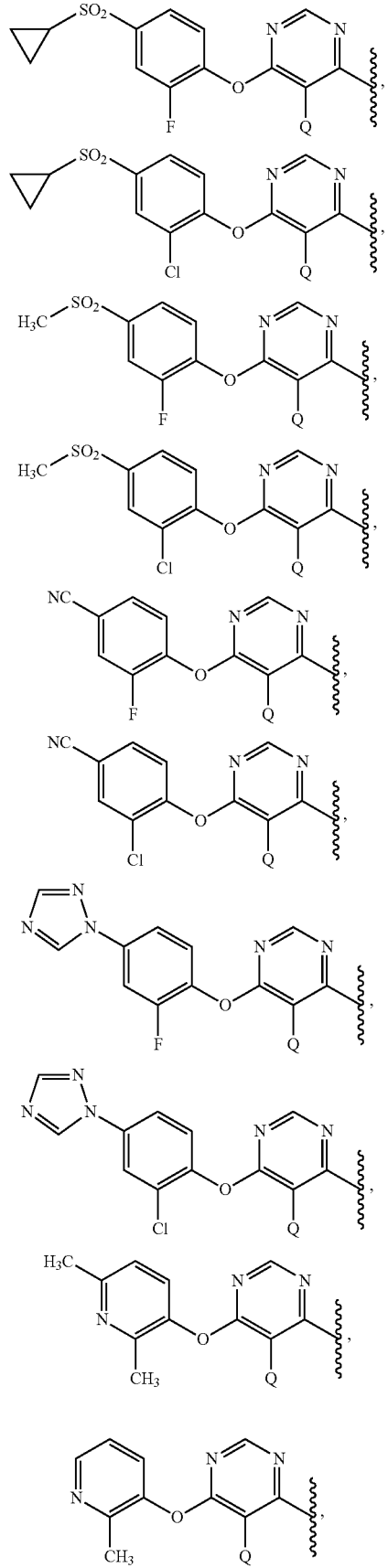
wherein Q is H, F, methyl or —OCH$_3$.
In still another embodiment, Y is —NH— and the group B—X-A- is:

-continued
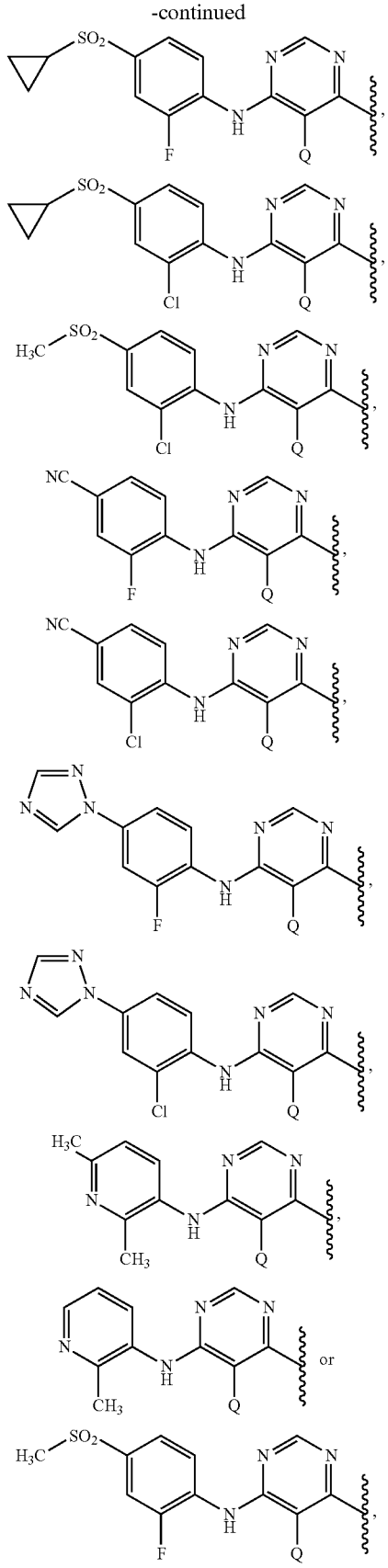
wherein Q is H, F, methyl or —OCH₃.
In one embodiment, Y is —O— and the group B—X-A- is:
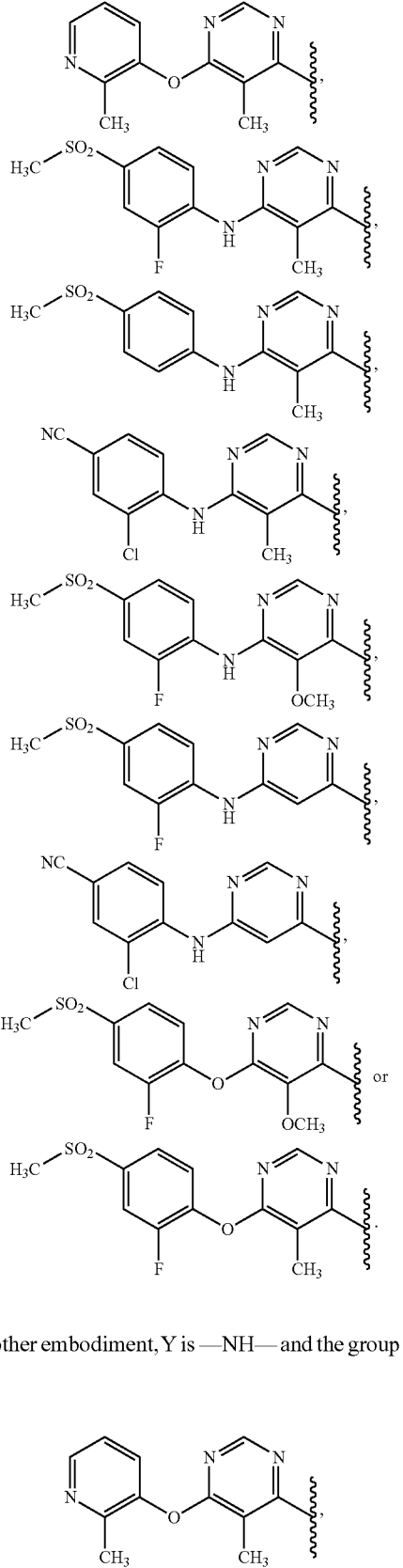
In another embodiment, Y is —NH— and the group B—X-A- is:
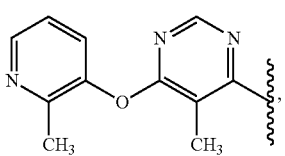

-continued
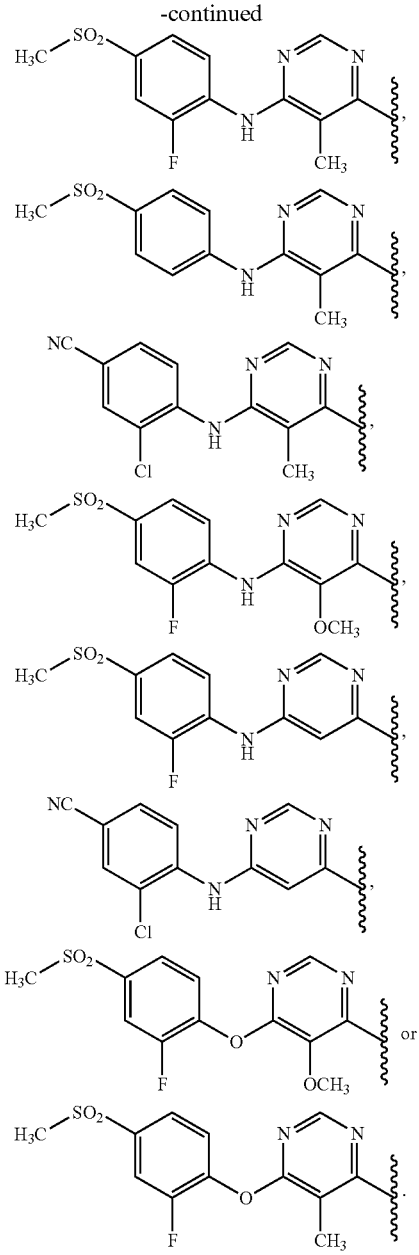
In one embodiment, the group B—X-A-Y— is:
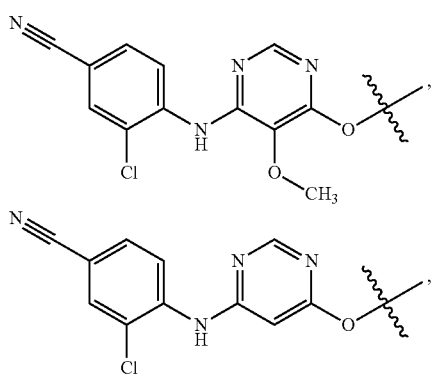
-continued
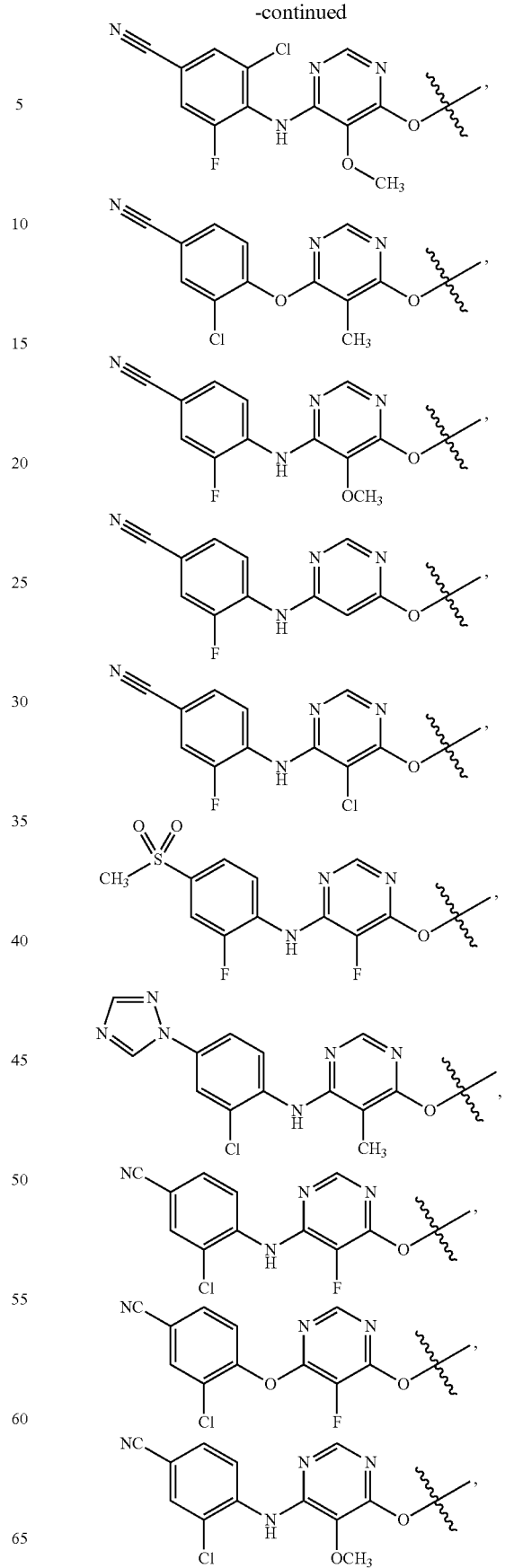

-continued

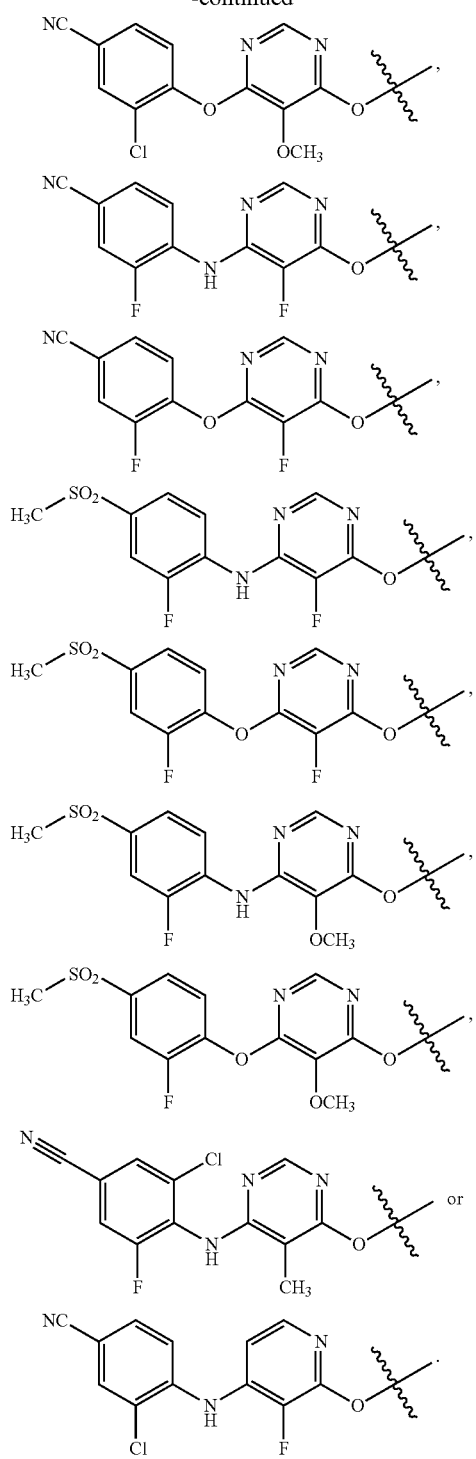

In another embodiment, the group B—X-A-Y— is:

-continued

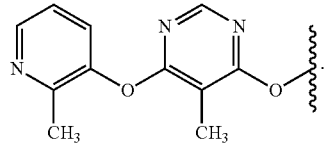 [SMILES: *Oc1ncnc(Oc2cccnc2C)c1C]

In another embodiment, the group B—X-A-Y— is:

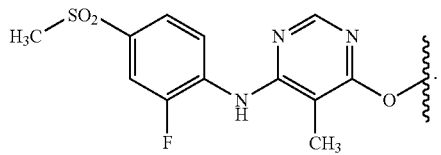 [SMILES: *Oc1ncnc(Nc2ccc(S(C)(=O)=O)cc2F)c1C]

In another embodiment, the group B—X-A-Y— is:

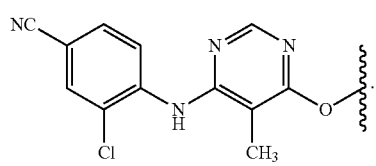 [SMILES: *Oc1ncnc(Nc2ccc(C#N)cc2Cl)c1C]

In another embodiment, the group B—X-A-Y— is:

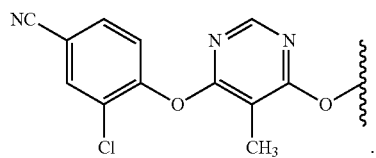 [SMILES: *Oc1ncnc(Oc2ccc(C#N)cc2Cl)c1C]

In still another embodiment, the group B—X-A-Y— is:

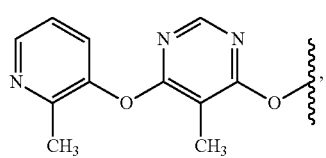

In still another embodiment, p and q are each 1 and Z is —CH—.

In another embodiment, p and q are each 1, Z is —CH—, and W is —C(O)O—.

In another embodiment, p and q are each 1, Z is —CH—, W is —C(O)O—, and $R^3$ is alkyl.

In another embodiment, p and q are each 1, Z is —CH—, W is —C(O)O—, and R³ is isopropyl or t-butyl.

In a further embodiment, p and q are each 1, Z is —CH—, W is —C(O)O—, R³ is alkyl, and X is —O— or —NH—.

In a further embodiment, p and q are each 1, Z is —CH—, W is —C(O)O—, R³ is alkyl, X is —O— or —NH—, and Y is —O— or —NH—.

In another embodiment, p and q are each 1, Z is —CH—, W is —C(O)O—, R³ is alkyl, X is —O— or —NH—, Y is —O— or —NH—, A is a 5 or 6-membered heteroaryl, and B is phenyl or a 5 or 6-membered heteroaryl.

In another embodiment, p and q are each 1, Z is —CH—, W is —C(O)O—, R³ is alkyl, X is —O— or —NH—, Y is —O— or —NH—, A is a 5 or 6-membered heteroaryl, B is phenyl or pyridyl, and R³ is heteroaryl.

In another embodiment, p and q are each 1, Z is —CH—, W is —C(O)O—, R³ is alkyl, X is —O— or —NH—, Y is —O— or —NH—, A is a 5 or 6-membered heteroaryl, B is phenyl or a 5 or 6-membered heteroaryl, each occurrence of R¹ is H, and R³ is heteroaryl.

In another embodiment, p and q are each 1, Z is —CH—, W is —C(O)O—, R³ is alkyl, X is —O— or —NH—, Y is —O— or —NH—, A is a 5 or 6-membered heteroaryl, B is phenyl or a 5 or 6-membered heteroaryl, each occurrence of R¹ and R² is H, and R³ is heteroaryl.

In one embodiment, the group:

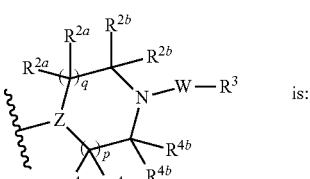

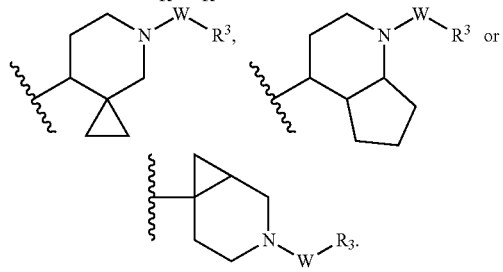

and W is —C(O)O—.

In another embodiment, the group:

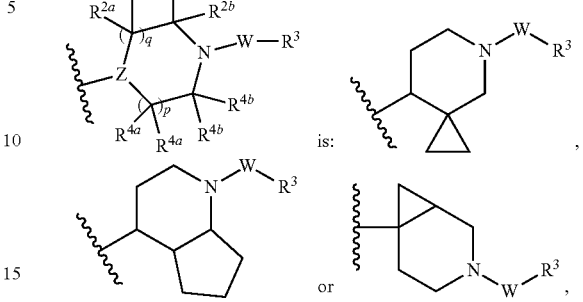

W is —C(O)O—, and R³ is alkyl.

In another embodiment, the group:

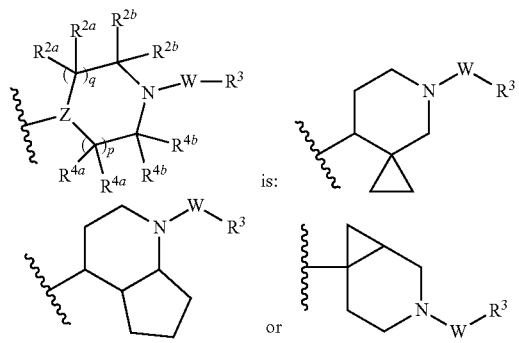

W is —C(O)O—, and R³ is isopropyl or t-butyl.

In one embodiment, Y is —O—, the group B—X—A- is:

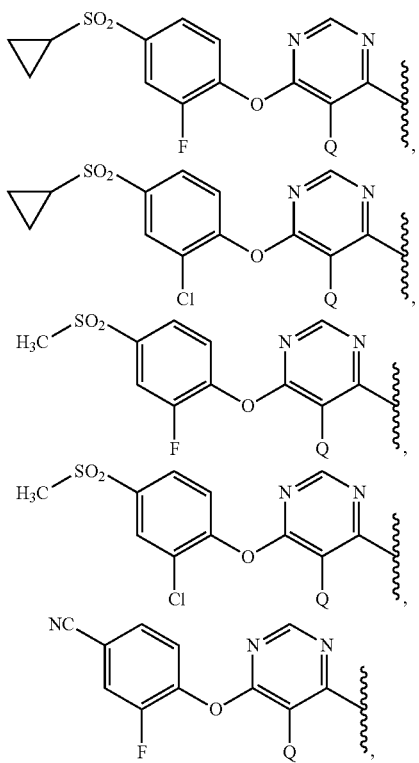

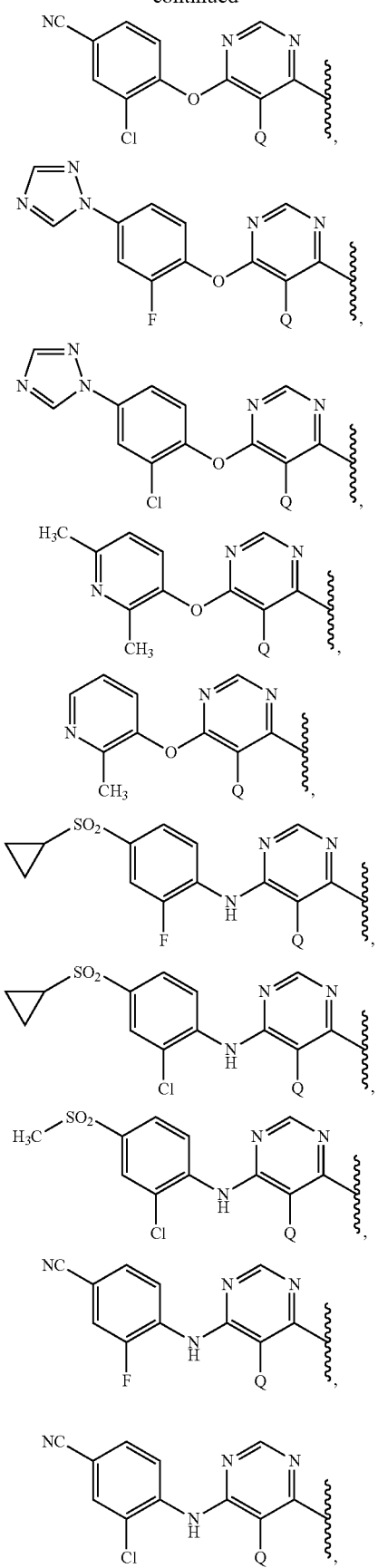
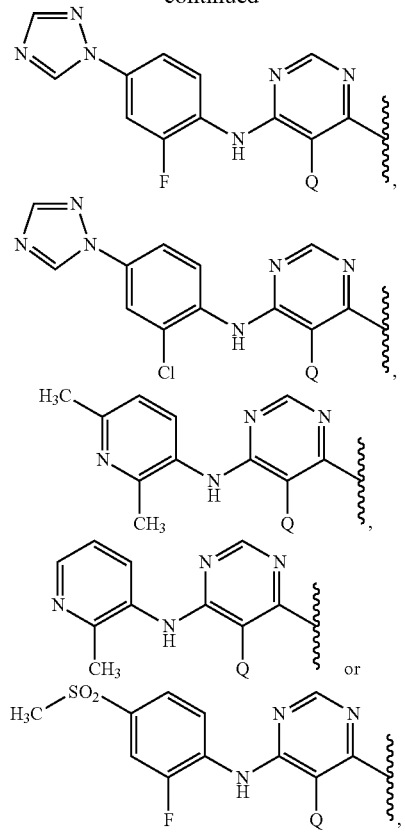
wherein Q is H, halo, alkyl or —O-alkyl, and the group:
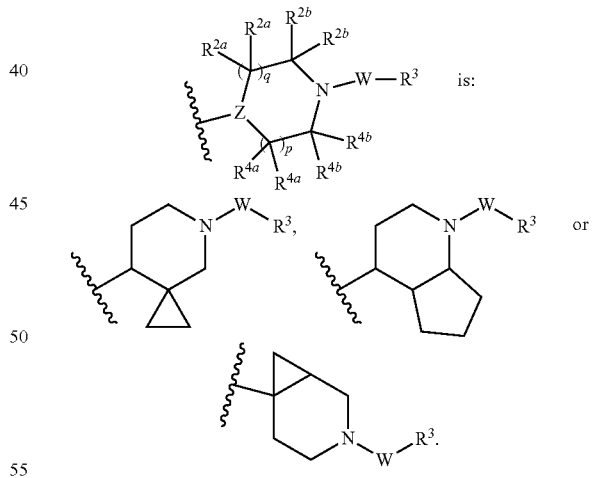
In another embodiment, Y is —NH—, the group B—X-A- is:
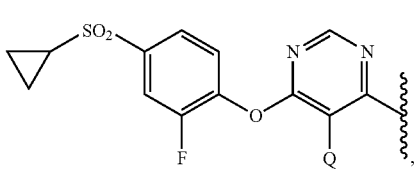

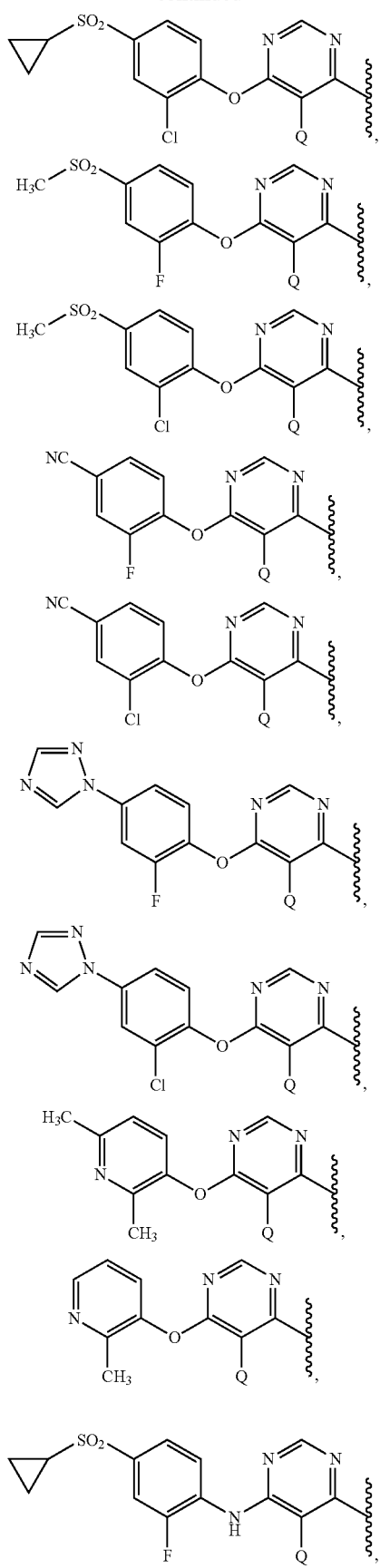
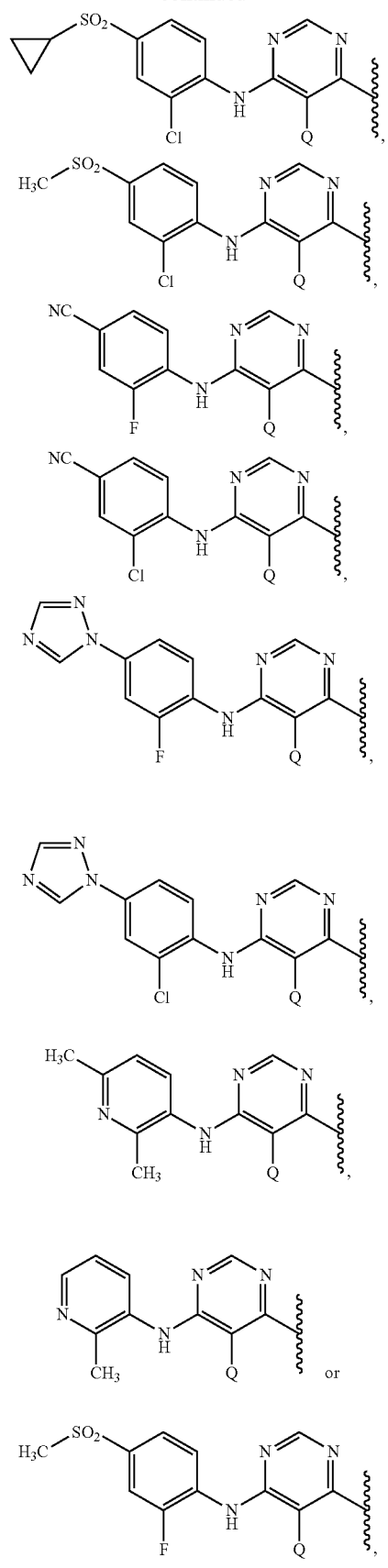

wherein Q is H, halo, alkyl or —O-alkyl, and the group:
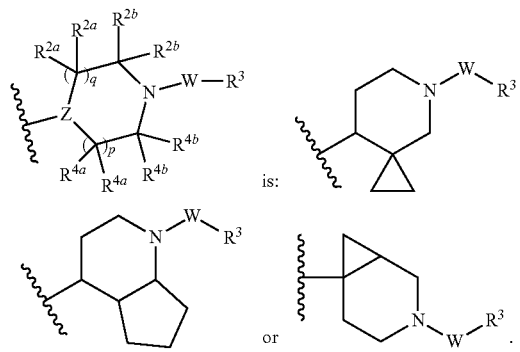
is:
In another embodiment, Y is —O—, the group B—X-A- is:
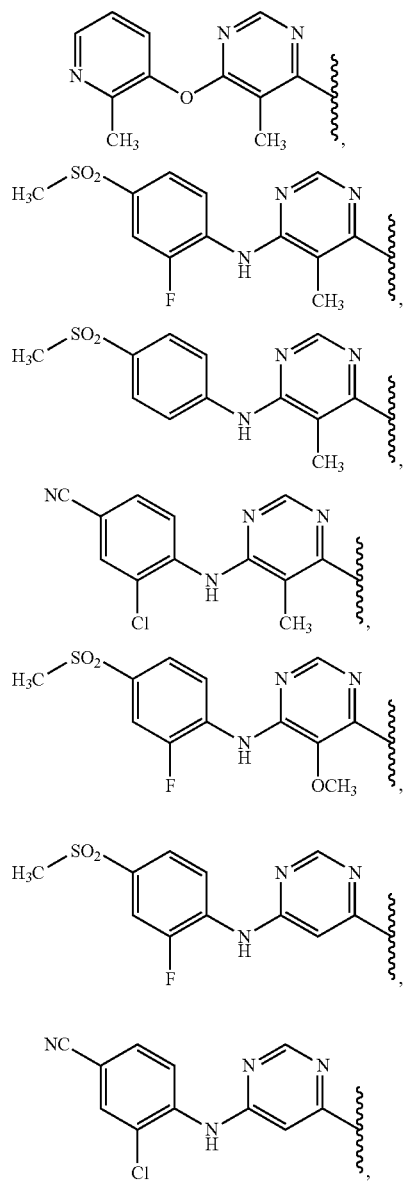
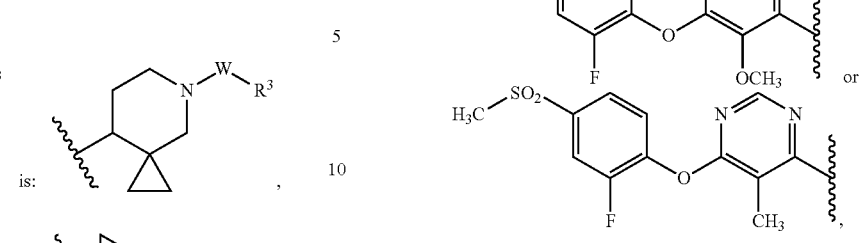
and the group
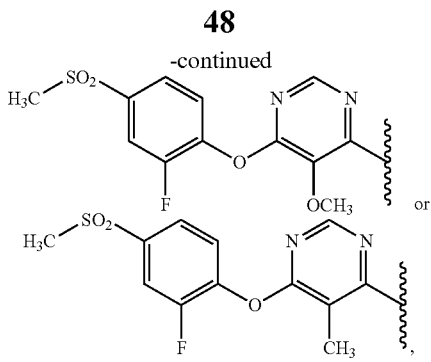
is:
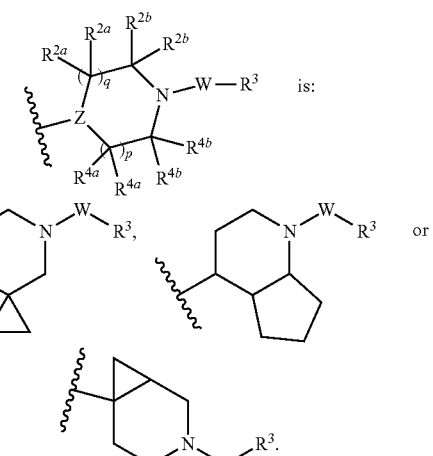
In still another embodiment, Y is —NH—, the group B—X-A- is:
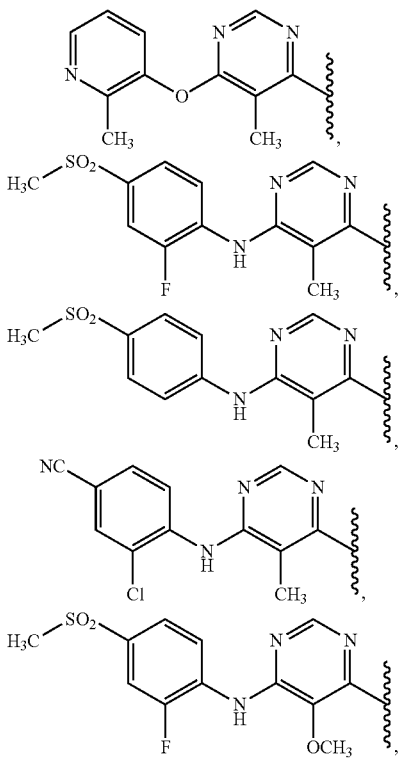

-continued

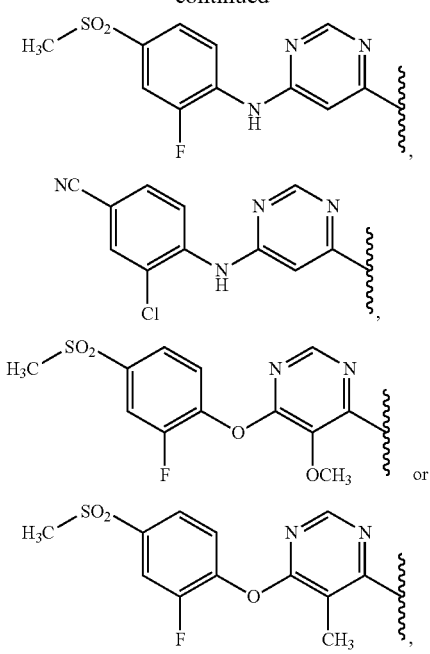

and the group

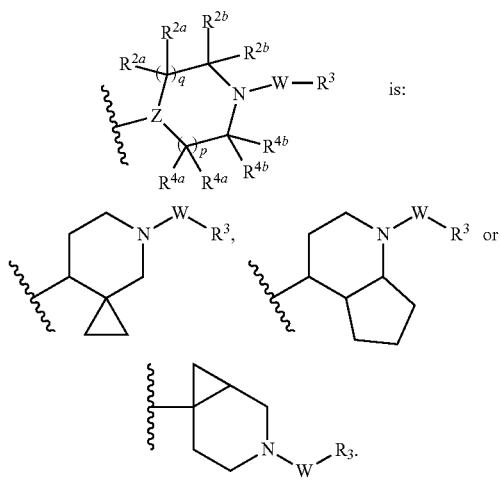

In one embodiment, the group B—X-A-Y— is:

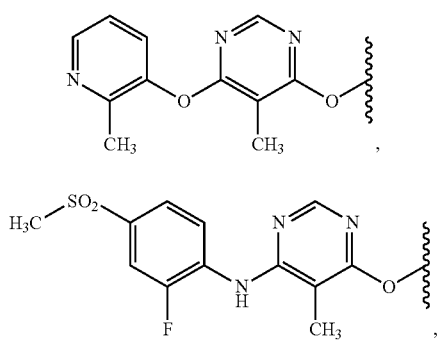

-continued

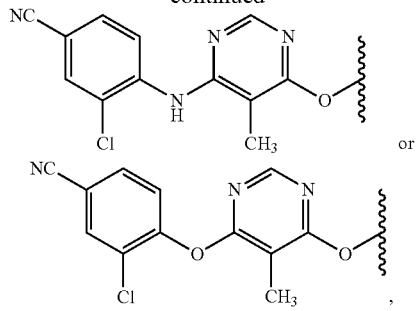

and the group

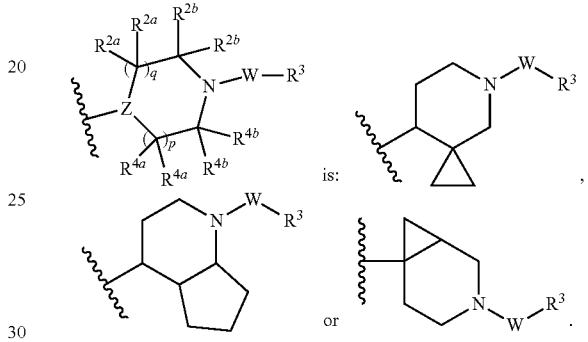

In one embodiment, the present invention provides compounds of Formula (I), wherein A, B, W, X, Y, Z, $R^{2a}$, $R^{2b}$, $R^{4a}$, $R^{4b}$, p and q are selected independently of each other.

In another embodiment, a compound of formula (I) is in purified form.

In one embodiment, the compounds of formula (I) have the formula (Ia):

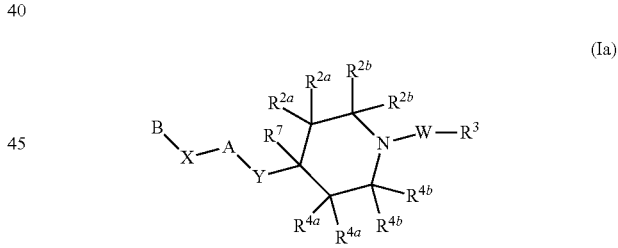

(Ia)

wherein:

A is pyrimdinyl, which can be optionally substituted with an alkyl, halo or —O-alkyl group;

B is phenyl or pyridyl, both of which can be optionally substituted with up to 3 groups, which can be the same or different, and are selected from alkyl, halo, heteroaryl, —CN, —S(O)$_2$alkyl and —S(O)$_2$cycloalkyl;

X is —O— or —NH—;

Y is —O— or —NH—;

each occurrence of $R^{2a}$ is H, wherein (i) any two $R^{2a}$ groups, together with the carbon atoms to which each are attached, can join to form a cycloalkyl or heterocycloalkyl group, (ii) an $R^{2a}$ group and an $R^{2b}$ group, together with the carbon atoms to which each are attached, can join to form a cycloalkyl or heterocycloalkyl group, or (iii) $R^7$ and an $R^{2a}$ group, together with the carbon atoms to which each are attached, can join to form a cycloalkyl group;

each occurrence of $R^{2b}$ is H, wherein (i) any two $R^{2b}$ groups, together with the carbon atoms to which each are attached, can join to form a cycloalkyl or heterocycloalkyl group, or (ii) an $R^{2b}$ group and an $R^{2a}$ group, together with the carbon atoms to which each are attached, can join to form a cycloalkyl or heterocycloalkyl group;

$R^3$ is alkyl;

each occurrence of $R^{4a}$ is H, wherein (i) any two $R^{4a}$ groups, together with the carbon atoms to which each are attached, can join to form a cycloalkyl or heterocycloalkyl group, (ii) an $R^{4a}$ group and an $R^{4b}$ group, together with the carbon atoms to which each are attached, can join to form a cycloalkyl or heterocycloalkyl group, or (iii) $R^7$ and an $R^{4a}$ group, together with the carbon atoms to which each are attached, can join to form a cycloalkyl group;

each occurrence of $R^{4b}$ is H, wherein (i) any two $R^{4b}$ groups, together with the carbon atoms to which each are attached, can join to form a cycloalkyl or heterocycloalkyl group, or (ii) an $R^{4b}$ group and an $R^{4a}$ group, together with the carbon atoms to which each are attached, can join to form a cycloalkyl or heterocycloalkyl group; and $R^7$ is H or alkyl, or: (i) $R^7$ and an $R^{2a}$, together with the carbon atoms to which each are attached, can join to form a cycloalkyl group, or (ii) $R^7$ and an $R^{4a}$ group, together with the carbon atoms to which each are attached, can join to form a cycloalkyl group, such that (i) at least one of $R^{2a}$, $R^{2b}$, $R^{4a}$ or $R^{4b}$, and the carbon atom to which it is attached, must combine with a separate $R^{2a}$, $R^{2b}$, $R^{4a}$ or $R^{4b}$ group and the carbon atom to which it is attached, to form a cycloalkyl or heterocycloalkyl group, or (ii) $R^7$ and an $R^{2a}$ group, together with the carbon atoms to which each are attached, must combine to form a cycloalkyl group, or (iii) $R^7$ and an $R^{4a}$ group, together with the carbon atoms to which each are attached, must combine to form a cycloalkyl group.

In one embodiment, for the compounds of formula (Ia), the group B—X-A-Y— is:

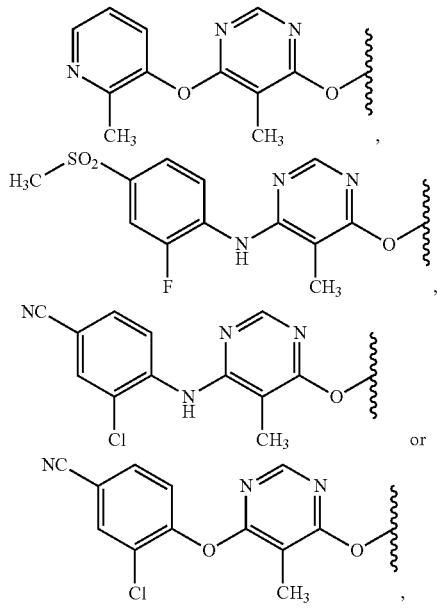

and the group

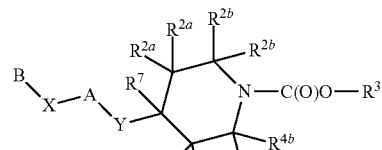

is:

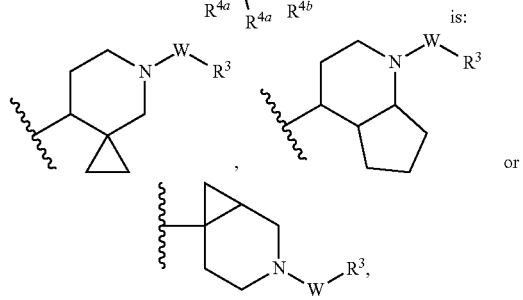

wherein W is —C(O)O—.

In another embodiment, for the compounds of formula (Ia), the group B—X-A-Y— is:

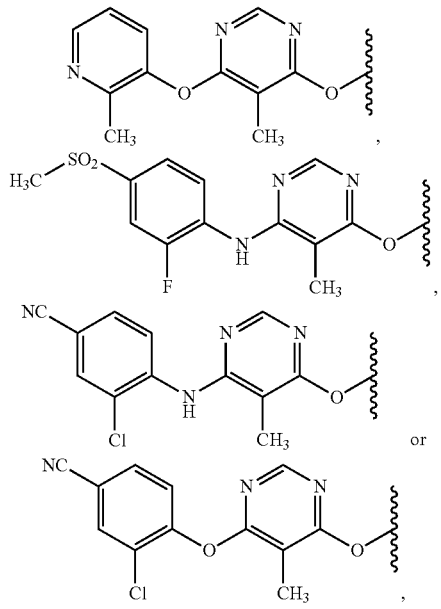

and the group

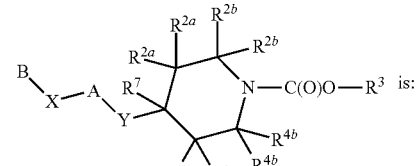

is:

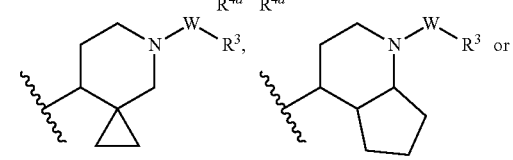

-continued

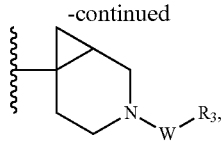

wherein W is —C(O)O— and R³ is alkyl.

In another embodiment, for the compounds of formula (Ia), the group B—X-A-Y— is:

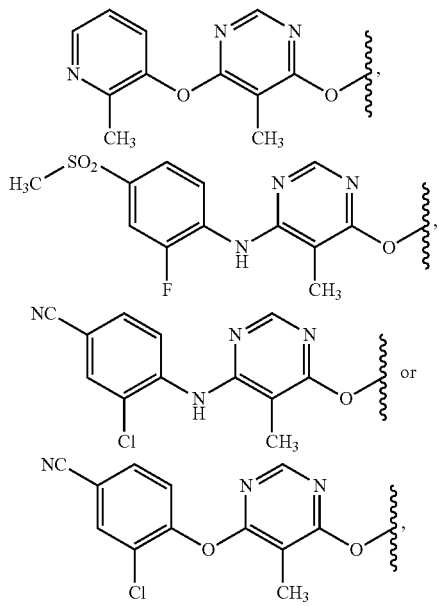

or and the group

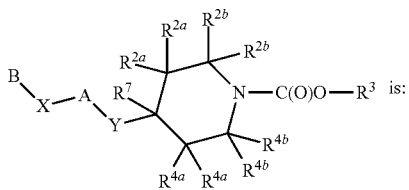

is:

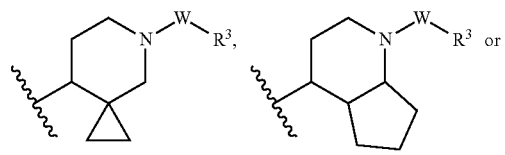

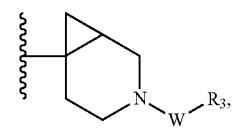

wherein W is —C(O)O— and R³ is isopropyl or t-butyl.

In one embodiment, the present invention provides compounds of Formula (Ia), wherein A, B, W, X, Y, $R^{2a}$, $R^{2b}$, $R^3$, $R^{4a}$, $R^{4b}$ and $R^7$ are selected independently of each other.

In another embodiment, a compound of formula (Ia) is in purified form.

Non-limiting examples of the Bicyclic Piperidine and piperazine Derivatives of the present invention include, but are not limited to, compounds 1-8, depicted below:

| Compound No. | Structure | MW |
|---|---|---|
| 1 | 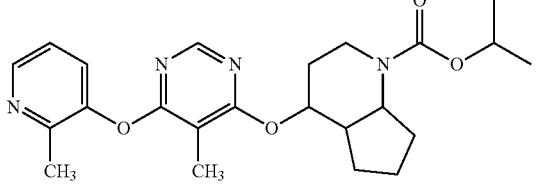<br>Isomer 1 | 427 |
| 2 | 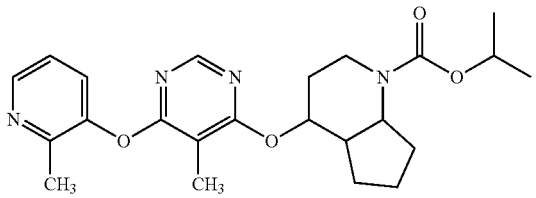<br>Isomer 2 | 427 |

-continued

| Compound No. | Structure | MW |
|---|---|---|
| 3 | 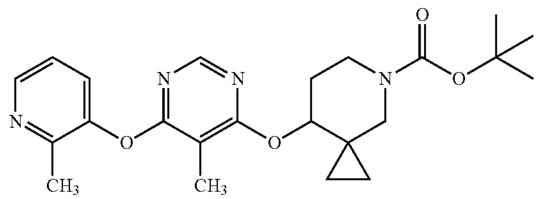 [SMILES: Cc1ncccc1Oc1ncnc(OC2CCN(C(=O)OC(C)(C)C)CC23CC3)c1C] | 427 |
| 4 | 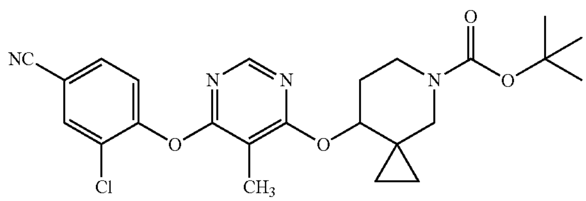 [SMILES: Cc1c(Oc2ccc(C#N)cc2Cl)ncnc1OC1CCN(C(=O)OC(C)(C)C)CC12CC2] | 471 |
| 5 | 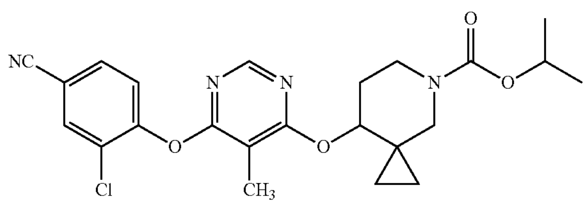 [SMILES: Cc1c(Oc2ccc(C#N)cc2Cl)ncnc1OC1CCN(C(=O)OC(C)C)CC12CC2] | 457 |
| 6 | 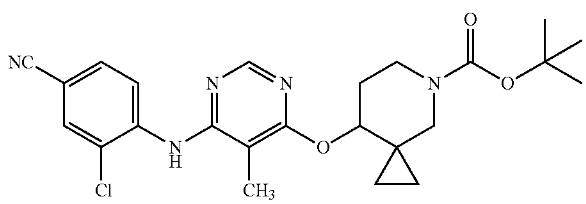 [SMILES: Cc1c(Nc2ccc(C#N)cc2Cl)ncnc1OC1CCN(C(=O)OC(C)(C)C)CC12CC2] | 470 |
| 7 | 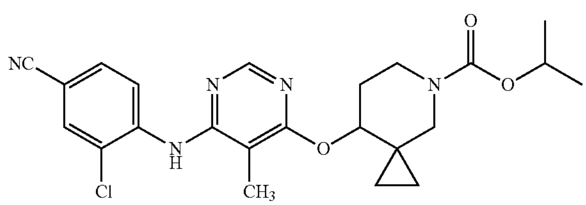 [SMILES: Cc1c(Nc2ccc(C#N)cc2Cl)ncnc1OC1CCN(C(=O)OC(C)C)CC12CC2] | 456 |
| 8 | 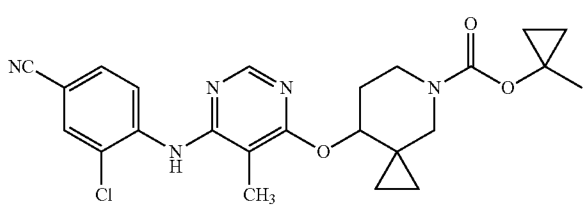 [SMILES: Cc1c(Nc2ccc(C#N)cc2Cl)ncnc1OC1CCN(C(=O)OC2(C)CC2)CC12CC2] | 468 |
| 9 | | 465 | and pharmaceutically acceptable salts, solvates, esters, prodrugs and stereoisomers thereof.
Additional non-limiting examples of the Bicyclic Piperidine and piperazine Derivatives of the present invention include, but are not limited to, the following compounds:
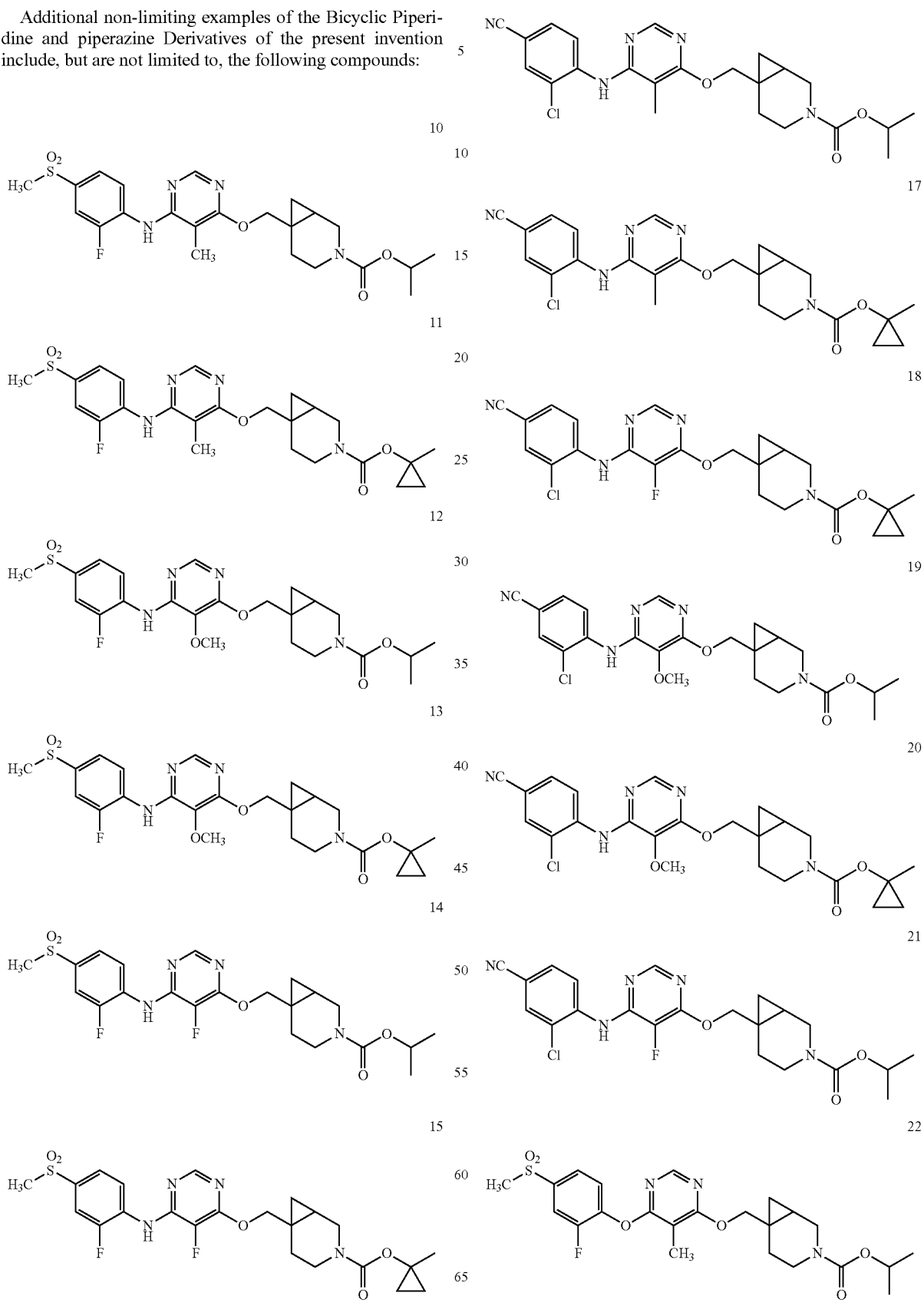

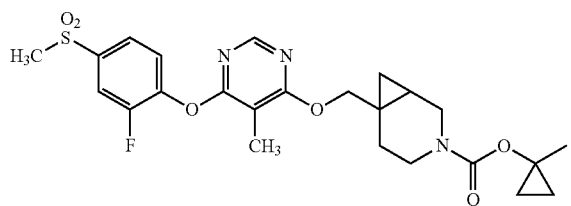
23
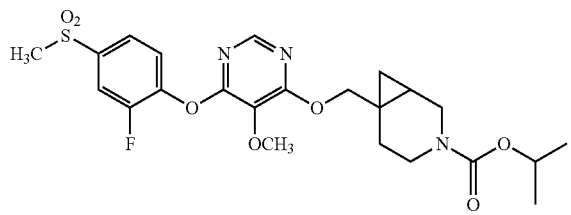
24
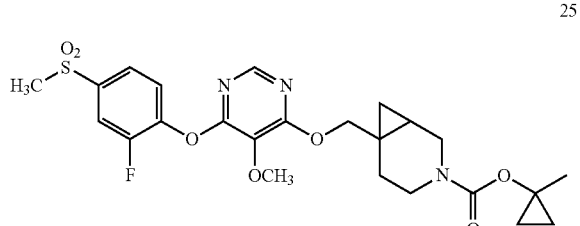
25
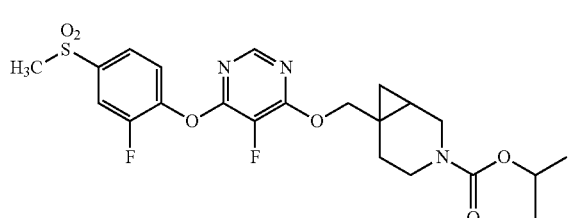
26
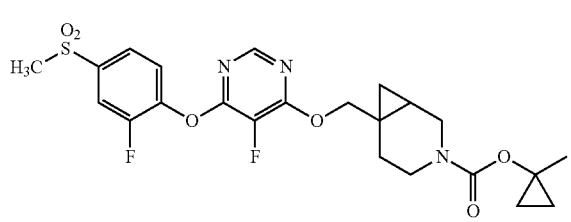
27
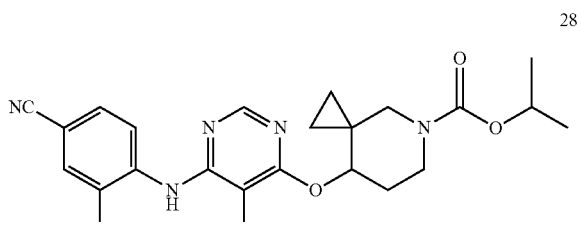
28
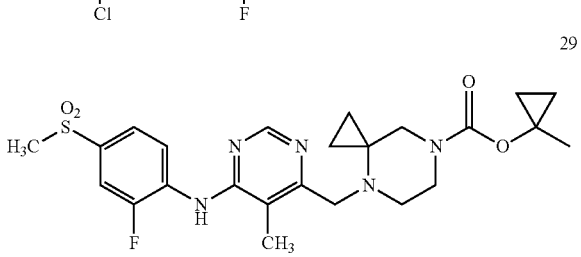
29
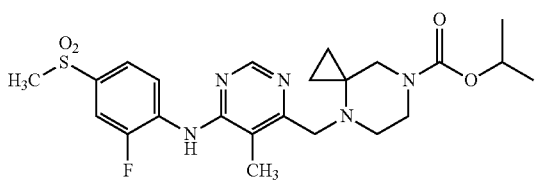
30
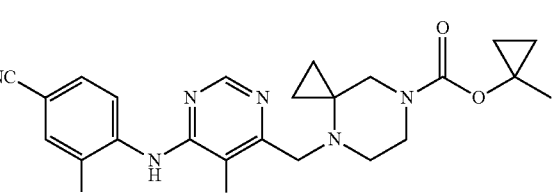
31
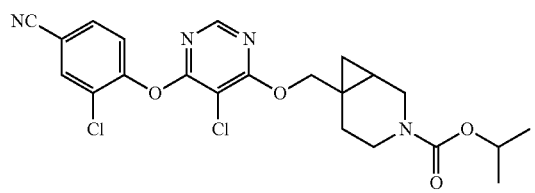
32
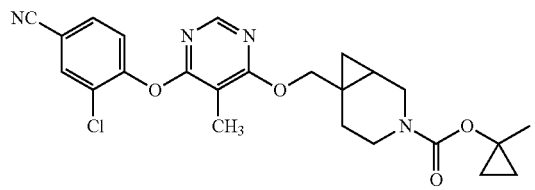
33
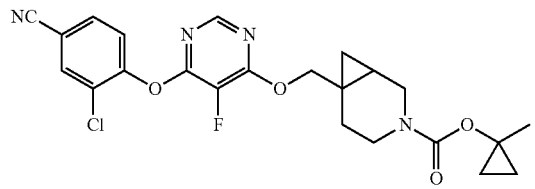
34
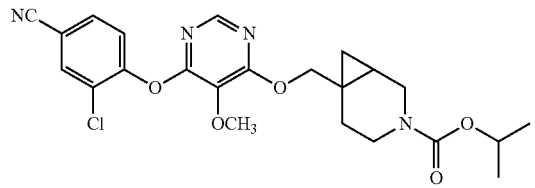
35
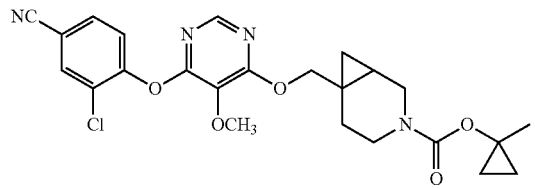
36
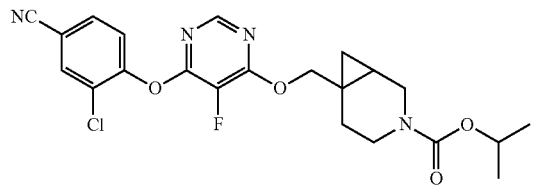
37 and pharmaceutically acceptable salts, solvates, esters, prodrugs and stereoisomers thereof.

Methods for Making the Bicyclic Piperidine and Piperazine Derivatives

Methods useful for making the Bicyclic Piperidine and piperazine Derivatives are set forth in the Examples below and generalized in Schemes 1-5. Alternative synthetic pathways and analogous structures will be apparent to those skilled in the art of organic synthesis.

Scheme 1 illustrates a method useful for making the compounds of formula iii, which are useful intermediates for making the Bicyclic Piperidine and piperazine Derivatives.

wherein G is —OH, —SH, —NHR$^{10}$ or a carbon nucleophile; X is —S—, —O—, —C(R$^1$)$_2$— or —NR$^{10}$; and A, B, R$^1$ and R$^{10}$ are defined above for the compounds of formula (I).

A dichloro aryl or heteroaryl compound of formula i can be reacted with a compound of formula ii in the presence of a non-nucleophilic base, such as potassium carbonate to provide the intermediate compounds of formula iii.

Scheme 2 illustrates a general method useful for making the compounds of formula iv, which are useful intermediates for making the Compounds of Formula (I).

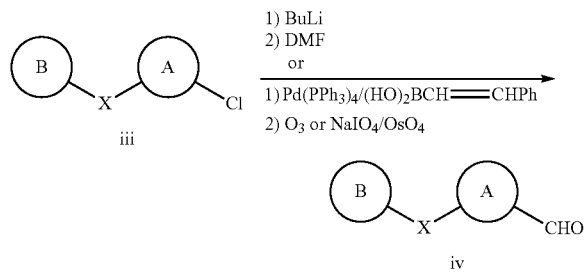

wherein X is —S—, —O—, —C(R$^1$)$_2$— or —NR$^{10}$; and A, B, R$^1$ and R$^{10}$ are defined above for the compounds of formula (I).

A compound of formula iii can be reacted with butyl lithium and quenched with DMF to form an aldehyde of formula iv. Alternatively, a compound of formula iii can form an alkene intermediate via palladium coupling. Oxidative cleavage of the alkene using ozone or sodium periodate/osmium tetroxide provides the aldehyde compounds of formula iv.

Scheme 3 illustrates a general method useful for making the compounds of formula (I) wherein Z is carbon and Y is —O—, —N(R)— or —S—.

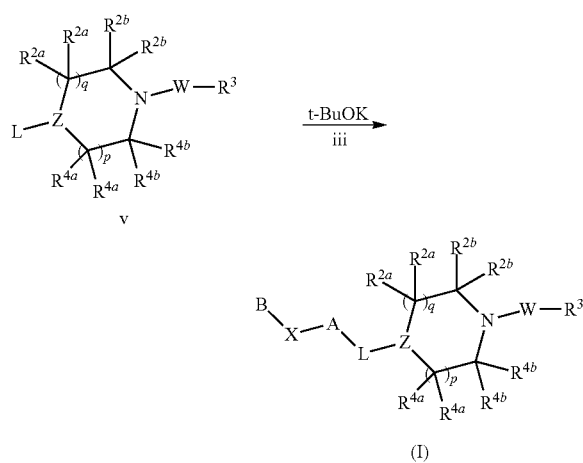

wherein Z is —C(R$^7$)—; L is —OH, —NHR$^1$ or —SH; Y is —O—, —N(R$^1$)— or —S—; and R$^{2a}$, R$^{2b}$, R$^3$ R$^{4a}$, R$^7$, W, X, Y, A, B, p and q are defined above for the compounds of formula (I).

A compound of formula v can be coupled with a compound of formula iii in the presence of potassium tert-butoxide using the method described in International Publication No. WO 07/035,355 to Jones et al., to provide the compounds of formula (I) wherein Z is carbon and Y is —O—, —N(R$^1$)— or —S—.

The compounds of formula v can be commercially available or can be prepared using methods well-known to one skilled in the art of organic synthesis.

Scheme 4 illustrates a general method useful for making the compounds of formula (I) wherein Z is —N—.

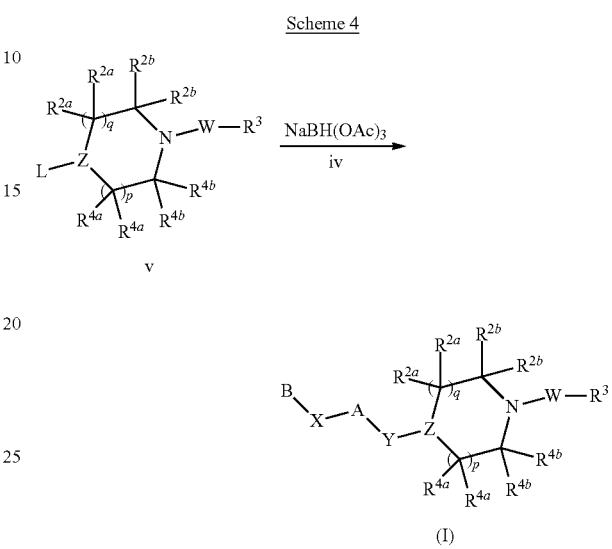

wherein Z is —N— and L is —H; Y must be joined to Z via a carbon atom and all R$^{2a}$ and/or R$^{4a}$ groups attached to any carbon atom adjacent to Z are each independently selected from H, alkyl, cycloalkyl and aryl; and R$^{2a}$, R$^{2b}$, R$^3$, R$^{4a}$, R$^{4b}$, W, X, A, B, p and q are defined above for the compounds of formula (I).

A compound of formula v can be coupled with a compound of formula iv using a reductive amination process to make the compounds of formula (I), wherein Z is —N—.

It will be apparent to one skilled in the art of organic synthesis as to how to construct the compounds of formula (I) wherein group Y is joined to group Z via a carbon-carbon bond. Such compounds can be made using the compounds of formula iii and formula iv, for example, or by using other intermediates analogous to compounds of formula iii and formula iv and employing well-known methods for forming carbon-carbon bonds. Such methods include, but are not limited to, organometallic coupling reactions, Wittig-type reactions and nucleophilic substitution reactions.

Scheme 5 illustrates a method for making compound ix, which is a useful intermediate for making the compounds of formula (I) wherein the group

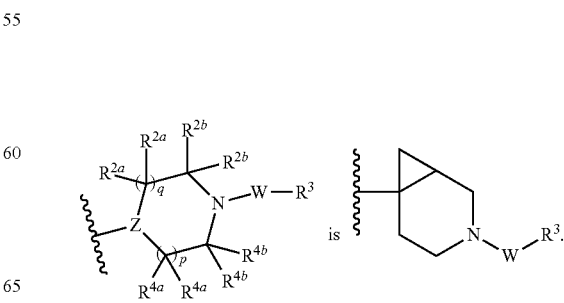

Scheme 5

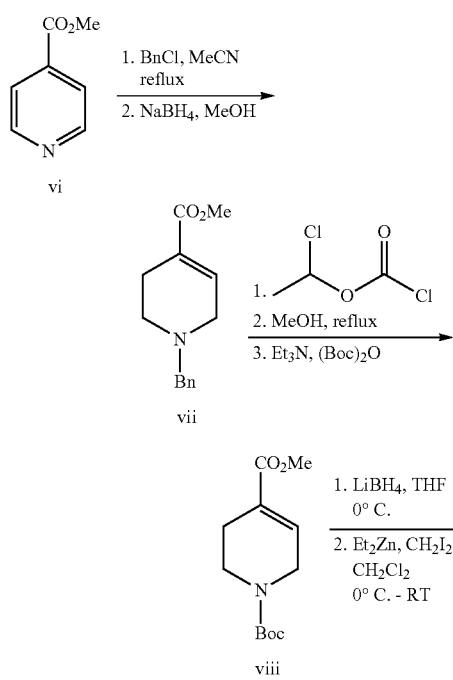

Methyl isonicotinate (vi) can be reduced to provide compound vii. The N-benzyl group of compound vii can then be replaced with a Boc group to provide compound viii. Finally, the alkene group of compound viii can be subjected to a cyclopropanation process to provide the intermediate compound ix.

The starting materials and reagents depicted in Schemes 1-5 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of the Bicyclic Piperidine and piperazine Derivatives of the present invention may require the need for the protection of certain functional groups (i.e., derivatization for the purpose of chemical compatibility with a particular reaction condition). Suitable protecting groups for the various functional groups of the Bicyclic Piperidine and piperazine Derivatives and methods for their installation and removal may be found in Greene et al., *Protective Groups in Organic Synthesis*, Wiley-Interscience, New York, (1999).

EXAMPLES

The following examples exemplify illustrative examples of compounds of the present invention and are not to be construed as limiting the scope of the disclosure. Alternative mechanistic pathways and analogous structures within the scope of the invention may be apparent to those skilled in the art.

General Methods

Solvents, reagents, and intermediates that are commercially available were used as received. Reagents and intermediates that are not commercially available were prepared in the manner described below. $^1$H NMR spectra were obtained on a Gemini AS-400 (400 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% $CH_3CN$, 5 min—95% $CH_3CN$, 7 min—95% $CH_3CN$, 7.5 min—10% $CH_3CN$, 9 min—stop. The observed parent ions are given.

Example 1

Preparation of Intermediate Compound 1C

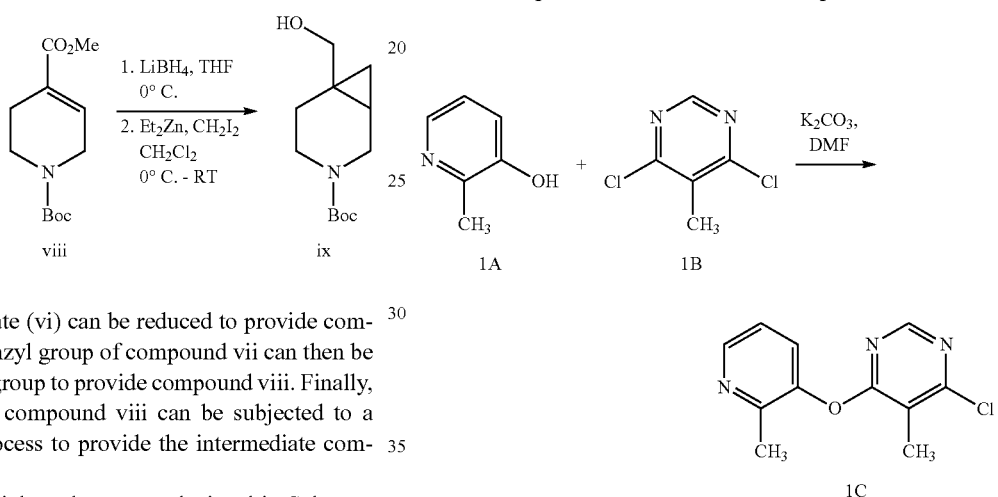

A solution of 2-methyl-pyridin-3-ol (1A, 3.3 g, 30.7 mmol) and 4,6-dichloro-5-methylpyrimidine (1B, 5.0 g, 30.7 mmol) in DMF (39 mL) was cooled to −5° C. and stirred for 1 hour. After, potassium carbonate (4.2 g, 30.7 mmol) was added in one portion and the reaction was warmed to room temperature and stirred for 18 hours. The reaction was cooled to 0° C. and cold water (40 mL) was added slowly. The solid precipitate was filtered and washed with cold water several times to provide the desired product 1C (5.5 g, 76%).

Example 2

Preparation of Intermediate Compound 2C

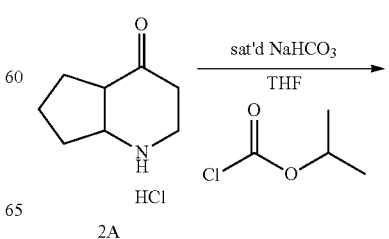

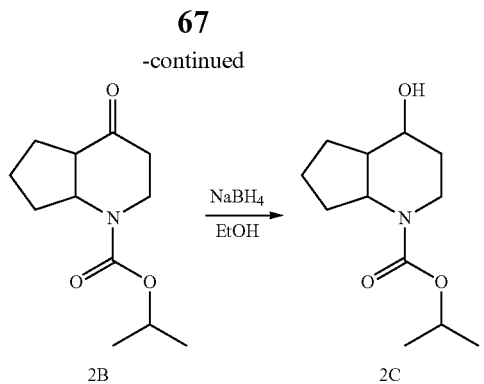

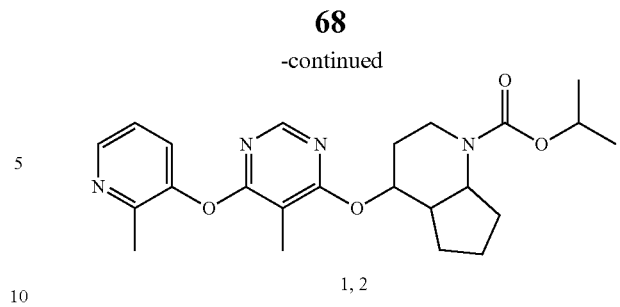

To a mixture of octahydro-4H-cyclopenta[b]pyridin-4-one hydrochloride (2A, 55 mg, 0.30 mmol) in THF (3 mL) was added sat'd NaHCO$_3$ (3 mL). The reaction was cooled to 0° C. and isopropyl chloroformate (1.0 M in toluene, 0.35 mmol) was added dropwise. The reaction was warmed to room temperature and stirred. After 16 h, the reaction was quenched with water and extracted with EtOAc. The combined organics were dried over MgSO$_4$, filtered and concentrated in vacuo to provide intermediate compound 2B (68 mg, 100%) which was used in the next reaction without further purification.

To a solution of compound 2B (68 mg, 0.30 mmol) in EtOH (4 mL) was added sodium borohydride (16 mg, 0.42 mmol). The reaction was stirred at room temperature under nitrogen. After 2.5 h, the solvent was removed in vacuo and the residue was quenched with water and extracted with DCM. The organic layer was dried over MgSO$_4$, filtered and concentrated to provide intermediate compound 2C (66 mg, 98%) which was used without further purification.

Example 3

Preparation of Compounds 1 and 2

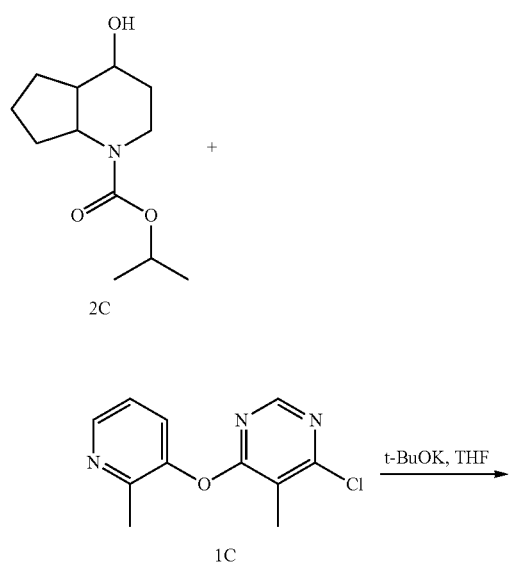

Potassium t-butoxide (1.0 M in THF, 0.3 mL) was added to a solution containing compound 2C (64 mg, 0.28 mmol) and compound 1C (67 mg, 0.28 mmol) in anhydrous THF (3 mL) under nitrogen at 0° C. The reaction was gradually warmed to room temperature and stirred for 16 hours. The reaction was quenched with water and extracted with DCM. The organic layer was dried over MgSO$_4$, filtered and concentrated in vacuo. The residue was purified by preparative thin layer chromatography (70/25/5 hexanes/EtOAc/IPA) to provide compound 1 (38 mg, 31%) and compound 2 (33 mg, 28%). Compound 2 was treated with HCl (1.0 M in ether, 0.08 mL) to provide the HCl salt of compound 2 (37 mg). M+H=427

Example 4

Preparation of Intermediate Compound 4C

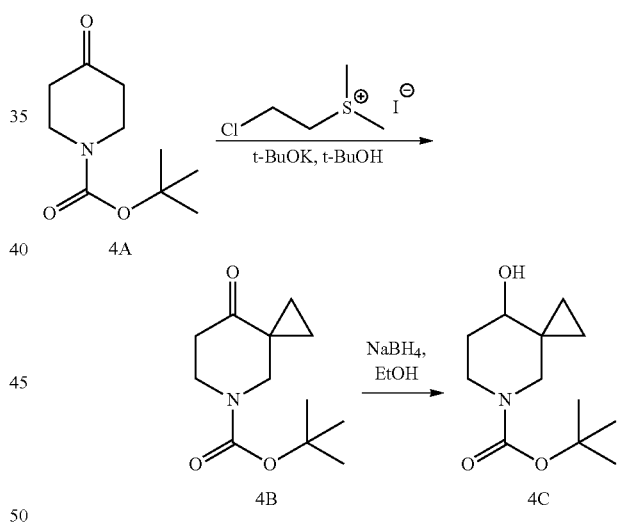

To a solution of potassium t-butoxide (0.85 g, 7.5 mol) in t-butanol (12 mL) was added t-butyl-4-oxopiperidine-1-carboxylate (4A, 1.5 g, 7.5 mol) under nitrogen. After 5 minutes, 2-chloroethyldimethyl sulfonium iodide (1.7 g, 6.8 mol) was added in portions over 10 minutes. 2-Chloroethyldimethyl sulfonium iodide was prepared according to Tet. Lett. 1984, 25, 5501-04. After stirring for 2 hours, additional potassium t-butoxide (0.85 g, 7.5 mol) in t-butanol (12 mL) was added and the reaction was stirred at room temperature for 16 hours. The reaction mixture was poured onto water and extracted with EtOAc. The combined organics were dried over MgSO$_4$, filtered and concentrated in vacuo Purification by silica gel flash chromatography (0-40% EtOAc/hexanes) afforded compound 4B (428 mg, 25%)

To a solution of compound 4B (422 mg, 1.87 mmol) in EtOH (28 mL) was added sodium borohydride (98 mg, 2.62 mmol) under nitrogen at 0° C. The reaction was warmed to room temperature and stirred for 18 hours. The reaction was quenched with water and extracted with DCM. The organic layer was dried over Na₂SO₄, filtered and concentrated in vacuo to provide the crude product 4C (420 mg, 99%) which was used without further purification.

Example 5

Preparation of Compound 3

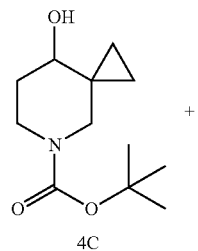

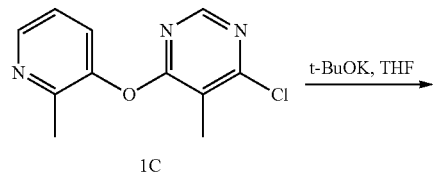

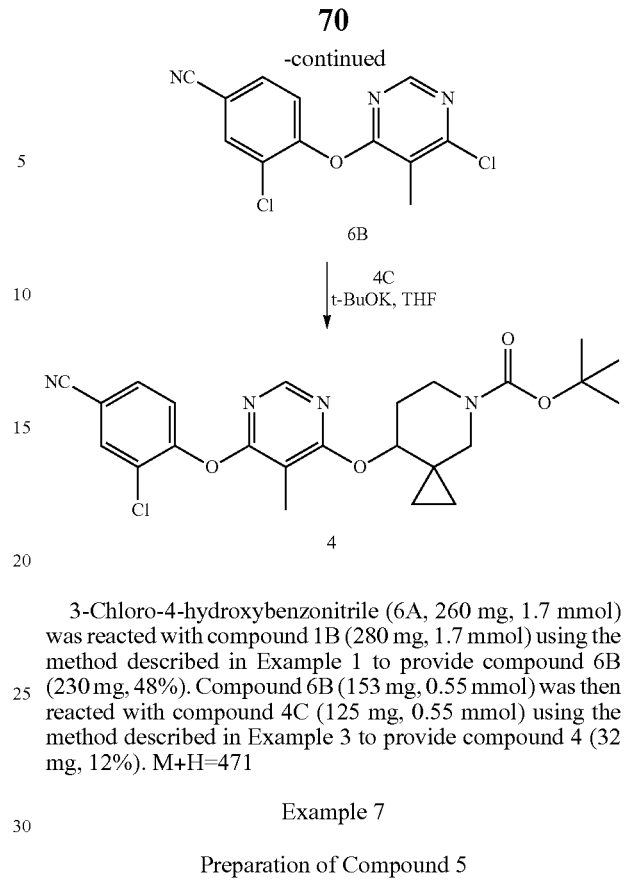

3-Chloro-4-hydroxybenzonitrile (6A, 260 mg, 1.7 mmol) was reacted with compound 1B (280 mg, 1.7 mmol) using the method described in Example 1 to provide compound 6B (230 mg, 48%). Compound 6B (153 mg, 0.55 mmol) was then reacted with compound 4C (125 mg, 0.55 mmol) using the method described in Example 3 to provide compound 4 (32 mg, 12%). M+H=471

Example 7

Preparation of Compound 5

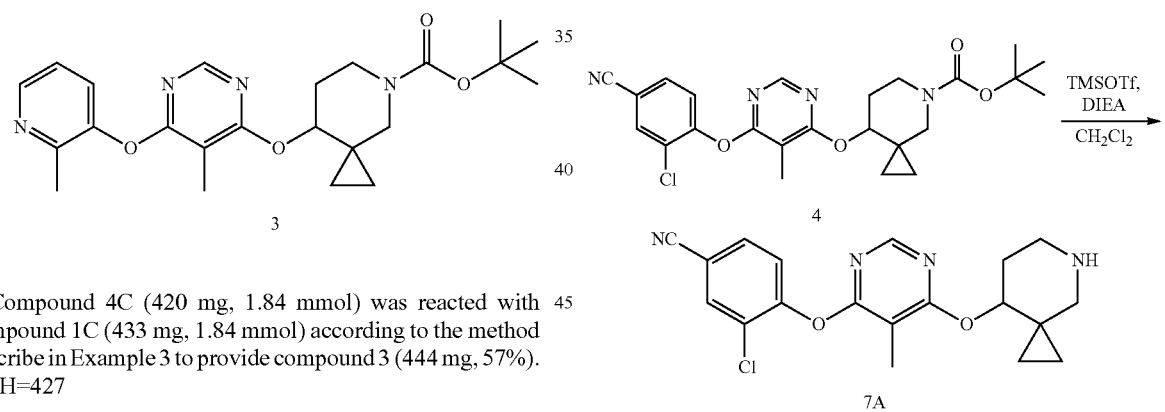

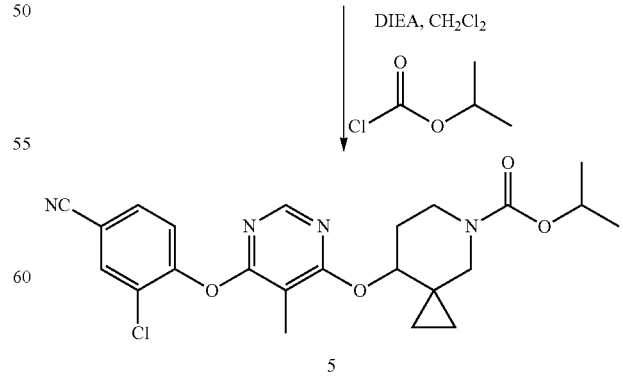

Compound 4C (420 mg, 1.84 mmol) was reacted with compound 1C (433 mg, 1.84 mmol) according to the method describe in Example 3 to provide compound 3 (444 mg, 57%). M+H=427

Example 6

Preparation of Compound 4

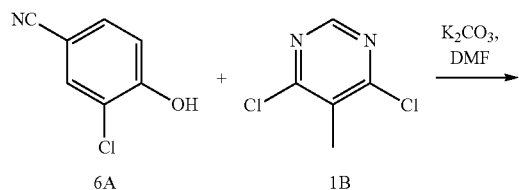

To a solution of compound 4 (20 mg, 0.043 mmol) in DCM (3 mL) was added DIEA (0.03 mL, 0.13 mmol), followed by trimethylsilyl trifluoromethanesulfonate (0.012 mL, 0.064 mmol) at 0° C. under nitrogen. The reaction was warmed to room temperature and allowed to stir at this temperature for 1.5 hours. The reaction was then quenched with water and extracted with DCM. The organic layer was dried over MgSO₄, filtered and concentrated in vacuo to provide the compound 7A, which was used without further purification.

To a solution of compound 7A in DCM (3 mL) was added DIEA (0.03 mL, 0.13 mmol) followed by isopropyl chloroformate (1.0 M in toluene, 0.086 mL, 0.086 mmol) at 0° C. under nitrogen. The reaction was warmed to room temperature and allowed to stir at this temperature for 2 hours. The reaction was then diluted with DCM and washed with saturated aqueous NH₄Cl solution. The organic phase was collected, dried over MgSO₄, filtered and concentrated in vacuo. The residue obtained was purified using preparative thin layer chromatography (4% MeOH/DCM) to provide compound 5 (16 mg, 80% over two steps). M+H=457

Example 8

Preparation of Compound 6

Compound 4C (70 mg, 0.31 mmol) was reacted with compound 1B (50 mg, 0.31 mmol) using the method described in Example 3 to provide intermediate compound 8A (55 mg, 50%) which was used in the next step without further purification.

A mixture of 4-amino-3-chlorobenzonitrile (8B, 25 mg, 0.16 mmol) and NaH (60%, 32 mg, 0.80 mmol) in THF (4 mL) was stirred at room temperature for 30 minutes. The reaction was then cooled to 0° C. and a solution of compound 8A (55 mg, 0.16 mmol) in THF (1.5 mL) was added. The reaction was gradually warmed to room temperature and then heated to 85° C. and allowed to stir at this temperature for 18 hours. The reaction mixture was cooled to room temperature and concentrated in vacuo. The residue obtained was purified using preparative thin layer chromatography (20% acetone/hexanes) to provide compound 6 (60 mg, 80%). M+H=470

Example 9

Preparation of Compound 7

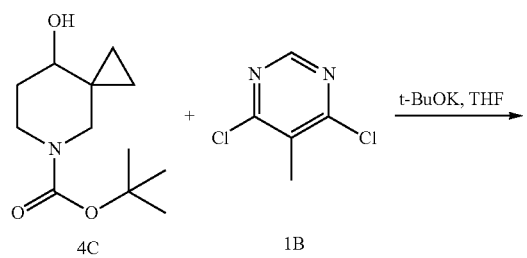

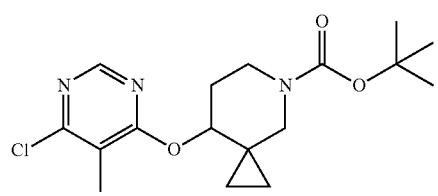

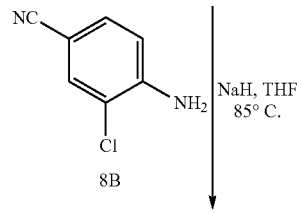

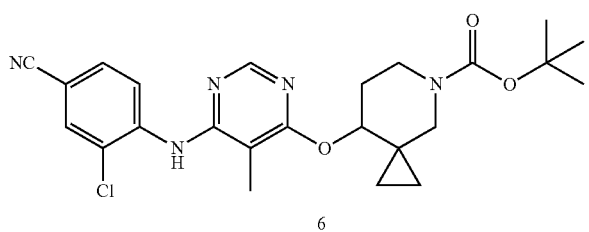

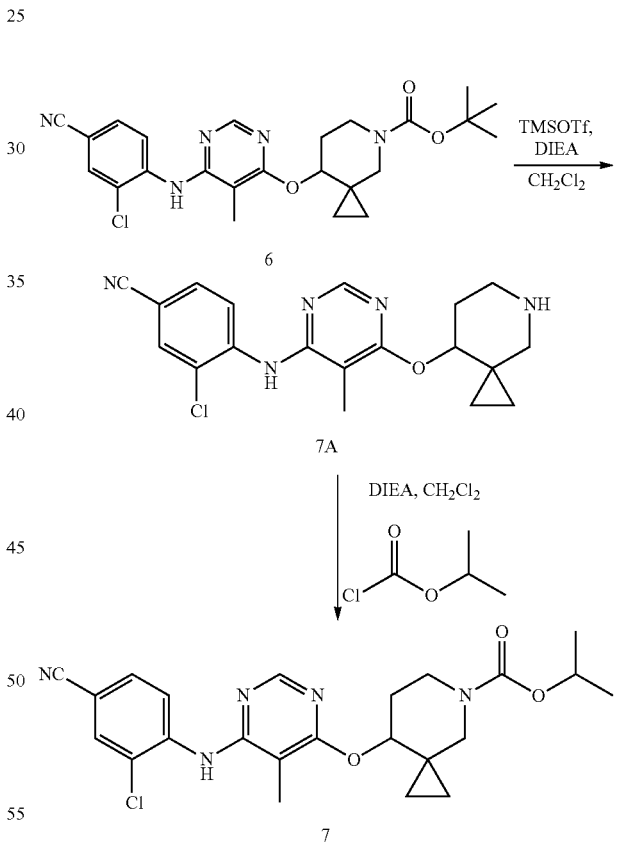

Compound 6 (55 mg, 0.12 mmol) was deprotected using the method described in Example 7 to provide intermediate 9A (44 mg, 100%) which was used in the next step without further purification.

Compound 9A (22 mg, 0.06 mmol) was reacted with isopropyl chloroformate using the method described in Example 7 to provide according to compound 7 (18 mg, 64%). M+H=456

Example 10

Preparation of Compound 8

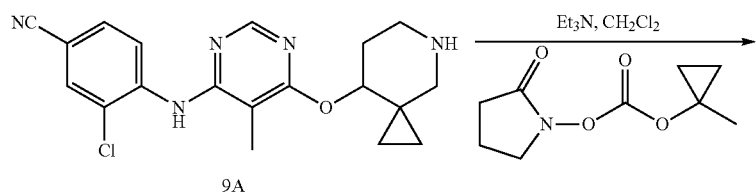

9A

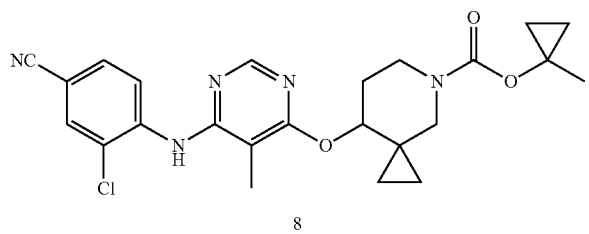

8

To a solution of compound 9A (22 mg, 0.06 mmol) in DCM (2 mL) was added triethylamine (0.03 mL, 0.22 mmol) under nitrogen. The reaction was cooled to 0° and 2,5-dioxopyrrolidin-1-yl 1-methylcyclopropyl carbonate (10A, 26 mg, 0.12 mmol) was added. The reaction was warmed to room temperature and stirred for 18 hours. The reaction mixture was diluted with DCM and washed with water several times. The organic layer was dried over $MgSO_4$, filtered and concentrated in vacuo. Purification by preparative thin flash chromatography (50% EtOAc/hexanes) afforded compound 8 (25 mg, 89%). M H=468

Example 11

Preparation of Compound 9

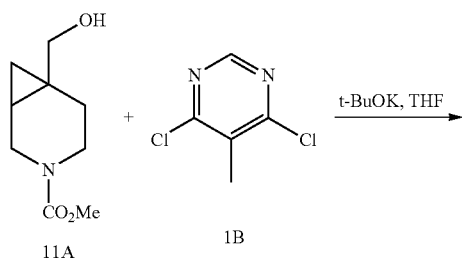

11A + 1B → (t-BuOK, THF)

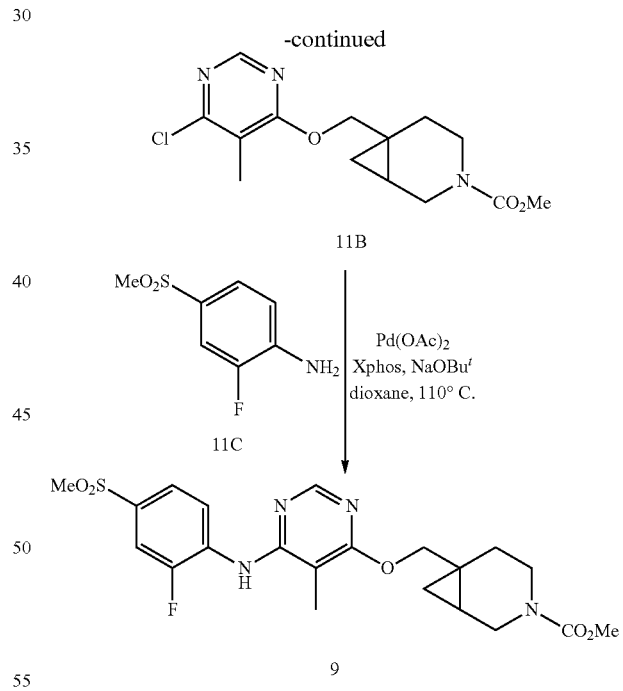

Compound 11A (40 mg, 0.18 mmol, prepared as described in U.S. Pat. No. 6,518,423) was reacted with 4,6-dichloro-5-methylpyrimidine 1B (28 mg, 0.18 mmol) using the method described in Example 8. The crude product obtained was purified using preparative thin layer chromatography (30% EtOAc/Hexanes) to provide compound 11B (35 mg, 62%).

To a solution of Compound 11B (34 mg, 0.11 mmol) in dioxane (1.8 mL), in a sealed tube, was added 2-fluoro-4-(methylsulfonyl)aniline (11C, 26 mg, 0.14 mmol), Xphos (24 mg, 0.05 mmol), palladium acetate (15 mg, 0.02 mmol) and sodium t-butoxide (16 mg, 0.016 mmol). The resulting reaction was heated to 110° C. and allowed to stir at this temperature for 16 hours, then cooled to room temperature and filtered. The filtrate was concentrated in vacuo and the residue obtained was purified using preparative thin layer chromatography (4% MeOH/DCM) to provide compound 9 (11 mg, 21%). M+H=465

Example 12 cAMP Assay

The ability of illustrative compounds of the invention to activate GPR119 and stimulate increases in cAMP levels was determined using the LANCE™ cAMP kit (Perkin Elmer). HEK293 cells expressing human GPR119 were maintained in culture flasks at 37° C./5% $CO_2$ in DMEM containing 10% fetal bovine serum, 100 U/ml Pen/Strep, and 0.5 mg/ml geneticin. The media was changed to Optimem and cells were incubated overnight at 37° C./5% $CO_2$. The Optimem was then aspirated and the cells were removed from the flasks using room temperature Hank's balanced saline solution (HBSS). The cells were pelleted using centrifugation (1300 rpm, 7 minutes, room temperature), then resuspended in stimulation buffer (HBSS, 0.1% BSA, 5 mM HEPES, 15 RO-20) at $2.5 \times 10^6$ cells/mL. Alexa Fluor 647-anti cAMP antibody (1:100) was then added to the cell suspension and incubated for 30 minutes. A representative Bicyclic Piperidine and piperazine Derivative (6 µl at 2× concentration) in stimulation buffer containing 2% DMSO were then added to white 384 well Matrix plates. Cell suspension mix (6 µl) was added to each well and incubated with the Bicyclic Piperidine and piperazine Derivative for 30 minutes. A cAMP standard curve was also created in each assay according to the kit protocol. Standard concentrations of cAMP in stimulation buffer (6 µl) were added to white 384 well plates. Subsequently, 6 µl of 1:100 anti-cAMP antibody was added to each well. Following the 30 minute incubation period, 12 µl of detection mix (included in kit) was added to all wells and incubated for 2-3 hours at room temperature. Fluorescence was detected on the plates using an Envision instrument. The level of cAMP in each well is determined by extrapolation from the cAMP standard curve.

Using this assay, $EC_{50}$ values for various illustrative Bicyclic Piperidine and piperazine Derivatives of the present invention were calculated and range from about 12 nM to about 10 µM.

Example 13

Effect of the Compounds of the Invention in Oral Glucose Tolerance Test

Male C57Bl/6NCrl mice (6-8 week old) are fasted overnight and randomly dosed with either vehicle (20% hydroxypropyl-β-cyclodextrin) or a representative compound of the invention (at 3, 10 or 30 mg/kg) via oral gavage (n=8 mice/group). Glucose is then administered to the animals 30 minutes post-dosing (3 g/kg p.o.). Blood glucose is measured prior to administration of test compound and glucose, and at 20 minutes after glucose administration using a hand-held glucometer (Ascensia Elite, Bayer) and the before and after treatment measurements can then be compared to determine the effect of the test compound in response to glucose challenge.

Example 14

Effect of the Compounds of the Invention in an Animal Model of Diabetes

Four week old male C57Bl/6NCrl mice can be used to generate a nongenetic model of type 2 diabetes mellitus as previously described (*Metabolism* 47(6): 663-668, 1998). Briefly, mice are made insulin resistant by high fat feeding (60% of kcal as fat) and hyperglycemia is then induced using a low dose of streptozotocin (100 mg/kg i.p.). Eight weeks after streptozotocin administration, the diabetic mice are placed into one of 4 groups (n=13/gp) receiving the following treatments: vehicle (20% hydroxypropyl-β-cyclodextrin p.o.), compound to be tested (30 mg/kg p.o.), glipizide (20 mg/kg p.o.) or exendin-4 (10 ug/kg i.p.). Mice are dosed once daily for 13 consecutive days, and blood glucose levels are measured daily using, for example, a hand held glucometer, to determine the effects of the test compound(s) on glucose levels of the diabetic animals.

Uses of the Bicyclic Piperidine and Piperazine Derivatives

The Bicyclic Piperidine and piperazine Derivatives are useful in human and veterinary medicine for treating or preventing a Condition in a patient. In accordance with the invention, the Bicyclic Piperidine and piperazine Derivatives can be administered to a patient in need of treatment or prevention of a Condition.

In one embodiment, the present invention provides for the use of a Compound of Formula (I) or a pharmaceutically acceptable salt thereof, in the manufacture of a medicament for use in treating a condition selected from the group consisting of obesity, diabetes, a diabetic complication, a metabolic disorder, a cardiovascular disease or a disorder related to the activity of a G-Protein Coupled Receptor ("GPCR") in a patient.

Treatment of Obesity and Obesity-Related Disorders

The Bicyclic Piperidine and piperazine Derivatives can also be useful for treating obesity or an obesity-related disorder.

Accordingly, in one embodiment, the invention provides methods for treating obesity or an obesity-related disorder in a patient, wherein the method comprises administering to the patient an effective amount of one or more Bicyclic Piperidine and piperazine Derivatives, or a pharmaceutically acceptable salt, solvate, ester, prodrug or stereoisomer thereof.

Treatment of Diabetes

The Bicyclic Piperidine and piperazine Derivatives are useful for treating diabetes in a patient. Accordingly, in one embodiment, the present invention provides a method for treating diabetes in a patient, comprising administering to the patient an effective amount of one or more Bicyclic Piperidine and piperazine Derivatives.

Examples of diabetes treatable or preventable using the Bicyclic Piperidine and piperazine Derivatives include, but are not limited to, type I diabetes (insulin-dependent diabetes mellitus), type II diabetes (non-insulin dependent diabetes mellitus), gestational diabetes, autoimmune diabetes, insulinopathies, idiopathic type I diabetes (Type 1b), latent autoimmumne diabetes in adults, early-onset type 2 diabetes (EOD), youth-onset atypical diabetes (YOAD), maturity onset diabetes of the young (MODY), malnutrition-related diabetes, diabetes due to pancreatic disease, diabetes associated with other endocrine diseases (such as Cushing's Syndrome, acromegaly, pheochromocytoma, glucagonoma, primary aldosteronism or somatostatinoma), type A insulin resistance syndrome, type B insulin resistance syndrome, lipatrophic diabetes, diabetes induced by β-cell toxins, and diabetes induced by drug therapy (such as diabetes induced by antipsychotic agents).

In one embodiment, the diabetes is type I diabetes.

In another embodiment, the diabetes is type II diabetes.

Treatment of a Diabetic Complication

The Bicyclic Piperidine and piperazine Derivatives are also useful for treating a diabetic complication in a patient. Accordingly, in one embodiment, the present invention provides a method for treating a diabetic complication in a patient, comprising administering to the patient an effective amount of one or more Bicyclic Piperidine and piperazine Derivatives.

Examples of diabetic complications treatable or preventable using the Bicyclic Piperidine and piperazine Derivatives include, but are not limited to, diabetic cataract, glaucoma, retinopathy, aneuropathy (such as diabetic neuropathy, polyneuropathy, mononeuropathy, autonomic neuropathy, microaluminuria and progressive diabetic neuropathyl), nephropathy, gangrene of the feet, immune-complex vasculitis, systemic lupus erythematosus (SLE), atherosclerotic coronary arterial disease, peripheral arterial disease, nonketotic hyperglycemic-hyperosmolar coma, foot ulcers, joint problems, a skin or mucous membrane complication (such as an infection, a shin spot, a candidal infection or necrobiosis lipoidica diabeticorumobesity), hyperlipidemia, cataract, hypertension, syndrome of insulin resistance, coronary artery disease, a fungal infection, a bacterial infection, and cardiomyopathy.

Treatment of a Metabolic Disorder

The Bicyclic Piperidine and piperazine Derivatives can also be useful for treating a metabolic disorder. Examples of metabolic disorders treatable include, but are not limited to, metabolic syndrome (also known as "Syndrome X"), impaired glucose tolerance, impaired fasting glucose, hypercholesterolemia, hyperlipidemia, hypertriglyceridemia, low HDL levels, hypertension, phenylketonuria, post-prandial lipidemia, a glycogen-storage disease, Gaucher's Disease, Tay-Sachs Disease, Niemann-Pick Disease, ketosis and acidosis.

Accordingly, in one embodiment, the invention provides methods for treating a metabolic disorder in a patient, wherein the method comprises administering to the patient an effective amount of one or more Bicyclic Piperidine and piperazine Derivatives, or a pharmaceutically acceptable salt, solvate, ester, prodrug or stereoisomer thereof.

In one embodiment, the metabolic disorder is hypercholesterolemia.

In another embodiment, the metabolic disorder is hyperlipidemia.

In another embodiment, the metabolic disorder is hypertriglyceridemia.

In still another embodiment, the metabolic disorder is metabolic syndrome.

In a further embodiment, the metabolic disorder is low HDL levels.

Methods for Treating a Cardiovascular Disease

The Bicyclic Piperidine and piperazine Derivatives are useful for treating or preventing a cardiovascular disease in a patient.

Accordingly, in one embodiment, the present invention provides a method for treating a cardiovascular disease in a patient, comprising administering to the patient an effective amount of one or more Bicyclic Piperidine and piperazine Derivatives.

Illustrative examples of cardiovascular diseases treatable or preventable using the present methods, include, but are not limited to atherosclerosis, congestive heart failure, cardiac arrhythmia, myocardial infarction, atrial fibrillation, atrial flutter, circulatory shock, left ventricular hypertrophy, ventricular tachycardia, supraventricular tachycardia, coronary artery disease, angina, infective endocarditis, non-infective endocarditis, cardiomyopathy, peripheral artery disease, Reynaud's phenomenon, deep venous thrombosis, aortic stenosis, mitral stenosis, pulmonic stenosis and tricuspid stenosis.

In one embodiment, the cardiovascular disease is atherosclerosis.

In another embodiment, the cardiovascular disease is congestive heart failure.

In another embodiment, the cardiovascular disease is coronary artery disease.

Combination Therapy

In one embodiment, the present invention provides methods for treating a Condition in a patient, the method comprising administering to the patient one or more Bicyclic Piperidine and piperazine Derivatives, or a pharmaceutically acceptable salt, solvate, ester, prodrug or stereoisomer thereof and at least one additional therapeutic agent that is not a Bicyclic Piperidine and piperazine Derivative, wherein the amounts administered are together effective to treat or prevent a Condition.

Non-limiting examples of additional therapeutic agents useful in the present methods for treating or preventing a Condition include, anti-obesity agents, antidiabetic agents, any agent useful for treating metabolic syndrome, any agent useful for treating a cardiovascular disease, cholesterol biosynthesis inhibitors, cholesterol absorption inhibitors, bile acid sequestrants, probucol derivatives, IBAT inhibitors, nicotinic acid receptor (NAR) agonists, ACAT inhibitors, cholesteryl ester transfer proten (CETP) inhibitors, low-density lipoprotein (LDL) activators, fish oil, water-soluble fibers, plant sterols, plant stanols, fatty acid esters of plant stanols, or any combination of two or more of these additional therapeutic agents.

Non-limiting examples of anti-obesity agents useful in the present methods for treating a Condition include CB1 antagonists or inverse agonists such as rimonabant, neuropeptide Y antagonists, MCR4 agonists, MCH receptor antagonists, histamine $H_3$ receptor antagonists or inverse agonists, metabolic rate enhancers, nutrient absorption inhibitors, leptin, appetite suppressants and lipase inhibitors.

Non-limiting examples of appetite suppressant agents useful in the present methods for treating or preventing a Condition include cannabinoid receptor 1 ($CB_1$) antagonists or inverse agonists (e.g., rimonabant); Neuropeptide Y (NPY1, NPY2, NPY4 and NPY5) antagonists; metabotropic glutamate subtype 5 receptor (mGluR5) antagonists (e.g., 2-methyl-6-(phenylethynyl)-pyridine and 3[(2-methyl-1,4-thiazol-4-yl)ethynyl]pyridine); melanin-concentrating hormone receptor (MCH1R and MCH2R) antagonists; melanocortin receptor agonists (e.g., Melanotan-II and Mc4r agonists); serotonin uptake inhibitors (e.g., dexfenfluramine and fluoxetine); serotonin (5HT) transport inhibitors (e.g., paroxetine, fluoxetine, fenfluramine, fluvoxamine, sertaline and imipramine); norepinephrine (NE) transporter inhibitors (e.g., desipramine, talsupram and nomifensine); ghrelin antagonists; leptin or derivatives thereof; opioid antagonists (e.g., nalmefene, 3-methoxynaltrexone, naloxone and nalterxone); orexin antagonists; bombesin receptor subtype 3 (BRS3) agonists; Cholecystokinin-A (CCK-A) agonists; ciliary neurotrophic factor (CNTF) or derivatives thereof (e.g., butabindide and axokine); monoamine reuptake inhibitors (e.g., sibutramine); glucagon-like peptide 1 (GLP-1) agonists; topiramate; and phytopharm compound 57.

Non-limiting examples of metabolic rate enhancers useful in the present methods for treating or preventing a Condition include acetyl-CoA carboxylase-2 (ACC2) inhibitors; beta adrenergic receptor 3 (β3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, aminone, milrinone, cilostamide, rolipram and cilomilast); thyroid hormone 13 agonists; uncoupling protein activators (UCP-1, 2 or 3) (e.g., phytanic acid, 4-[(E)-2-(5,6,7,8-tetramethyl-2-naphthalenyl)-1-propenyl]benzoic acid and retinoic acid); acyl-estrogens (e.g., oleoyl-estrone); glucocorticoid antagonists; 11-beta hydroxy steroid dehydrogenase type 1 (11β HSD-1) inhibitors; melanocortin-3 receptor (Mc3r) agonists; and stearoyl-CoA desaturase-1 (SCD-1) compounds.

Non-limiting examples of nutrient absorption inhibitors useful in the present methods for treating or preventing a Condition include lipase inhibitors (e.g., orlistat, lipstatin, tetrahydrolipstatin, teasaponin and diethyl umbelliferyl phosphate); fatty acid transporter inhibitors; dicarboxylate transporter inhibitors; glucose transporter inhibitors; and phosphate transporter inhibitors.

Non-limiting examples of cholesterol biosynthesis inhibitors useful in the present methods for treating or preventing a Condition include HMG-CoA reductase inhibitors, squalene synthase inhibitors, squalene epoxidase inhibitors, and mixtures thereof.

Non-limiting examples of cholesterol absorption inhibitors useful in the present methods for treating or preventing a Condition include ezetimibe. In one embodiment, the cholesterol absorption inhibitor is ezetimibe.

HMG-CoA reductase inhibitors useful in the present methods for treating or preventing a Condition include, but are not limited to, statins such as lovastatin, pravastatin, fluvastatin, simvastatin, atorvastatin, cerivastatin, CI-981, resuvastatin, rivastatin, pitavastatin, rosuvastatin or L-659,699 ((E,E)-11-[3'R-(hydroxy-methyl)-4'-oxo-2'R-oxetanyl]-3,5,7R-trimethyl-2,4-undecadienoic acid).

Squalene synthesis inhibitors useful in the present methods for treating or preventing a Condition include, but are not limited to, squalene synthetase inhibitors; squalestatin 1; and squalene epoxidase inhibitors, such as NB-598 ((E)-N-ethyl-N-(6,6-dimethyl-2-hepten-4-ynyl)-3-[(3,3'-bithiophen-5-yl)methoxy]benzene-methanamine hydrochloride).

Bile acid sequestrants useful in the present methods for treating or preventing a Condition include, but are not limited to, cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl)alkylamines and poliglusam, insoluble quaternized polystyrenes, saponins and mixtures thereof. Suitable inorganic cholesterol sequestrants include bismuth salicylate plus montmorillonite clay, aluminum hydroxide and calcium carbonate antacids.

Probucol derivatives useful in the present methods for treating or preventing a Condition include, but are not limited to, AGI-1067 and others disclosed in U.S. Pat. Nos. 6,121,319 and 6,147,250.

IBAT inhibitors useful in the present methods for treating or preventing a Condition include, but are not limited to, benzothiepines such as therapeutic compounds comprising a 2,3,4,5-tetrahydro-1-benzothiepine 1,1-dioxide structure such as are disclosed in International Publication No. WO 00/38727.

Nicotinic acid receptor agonists useful in the present methods for treating or preventing a Condition include, but are not limited to, those having a pyridine-3-carboxylate structure or a pyrazine-2-carboxylate structure, including acid forms, salts, esters, zwitterions and tautomers, where available. Other examples of nicotinic acid receptor agonists useful in the present methods include nicotinic acid, niceritrol, nicofuranose and acipimox. An example of a suitable nicotinic acid product is NIASPAN® (niacin extended-release tablets) which are available from Kos Pharmaceuticals, Inc. (Cranbury, N.J.). Further nicotinic acid receptor agonists useful in the present methods for treating or preventing a Condition include, but are not limited to, the compounds disclosed in U.S. Patent Publication Nos. 2006/0264489 and 2007/0066630, and U.S. patent application Ser. No. 11/771,538, each of which is incorporated herein by reference.

ACAT inhibitors useful in the present methods for treating or preventing a Condition include, but are not limited to, avasimibe, HL-004, lecimibide and CL-277082 (N-(2,4-difluorophenyl)-N-[[4-(2,2-dimethylpropyl)phenyl]-methyl]-N-heptylurea). See P. Chang et al., "Current, New and Future Treatments in Dyslipidaemia and Atherosclerosis", *Drugs* 2000 July; 60(1); 55-93, which is incorporated by reference herein.

CETP inhibitors useful in the present methods for treating or preventing a Condition include, but are not limited to, those disclosed in International Publication No. WO 00/38721 and U.S. Pat. No. 6,147,090, which are incorporated herein by reference.

LDL-receptor activators useful in the present methods for treating or preventing a Condition include, but are not limited to, include HOE-402, an imidazolidinyl-pyrimidine derivative that directly stimulates LDL receptor activity. See M. Huettinger et al., "Hypolipidemic activity of HOE-402 is Mediated by Stimulation of the LDL Receptor Pathway", *Arterioscler Thromb.* 1993; 13:1005-12.

Natural water-soluble fibers useful in the present methods for treating or preventing a Condition include, but are not limited to, psyllium, guar, oat and pectin.

Fatty acid esters of plant stanols useful in the present methods for treating or preventing a Condition include, but are not limited to, the sitostanol ester used in BENECOL® margarine.

Non-limiting examples of antidiabetic agents useful in the present methods for treating a Condition include insulin sensitizers, α-glucosidase inhibitors, DPP-IV inhibitors, insulin secretagogues, hepatic glucose output lowering compounds, antihypertensive agents, sodium glucose uptake transporter 2 (SGLT-2) inhibitors, insulin and insulin-containing compositions, and anti-obesity agents as set forth above.

In one embodiment, the antidiabetic agent is an insulin secretagogue. In one embodiment, the insulin secretagogue is a sulfonylurea.

Non-limiting examples of sulfonylureas useful in the present methods include glipizide, tolbutamide, glyburide, glimepiride, chlorpropamide, acetohexamide, gliamilide, gliclazide, gliquidone, glibenclamide and tolazamide.

In another embodiment, the insulin secretagogue is a meglitinide.

Non-limiting examples of meglitinides useful in the present methods for treating a Condition include repaglinide, mitiglinide, and nateglinide.

In still another embodiment, the insulin secretagogue is GLP-1 or a GLP-1 mimetic.

Non-limiting examples of GLP-1 mimetics useful in the present methods include Byetta-Exanatide, Liraglutinide, CJC-1131 (ConjuChem), Exanatide-LAR (Amylin), BIM-51077 (Ipsen/LaRoche), ZP-10 (Zealand Pharmaceuticals), and compounds disclosed in International Publication No. WO 00/07617.

Other non-limiting examples of insulin secretagogues useful in the present methods include exendin, GIP and secretin.

In another embodiment, the antidiabetic agent is an insulin sensitizer.

Non-limiting examples of insulin sensitizers useful in the present methods include PPAR activators or agonists, such as troglitazone, rosiglitazone, pioglitazone and englitazone; biguanidines such as metformin and phenformin; PTP-1B inhibitors; and glucokinase activators.

In another embodiment, the antidiabetic agent is a α-Glucosidase inhibitor.

Non-limiting examples of α-Glucosidase inhibitors useful the present methods include miglitol, acarbose, and voglibose.

In another embodiment, the antidiabetic agent is an hepatic glucose output lowering agent.

Non-limiting examples of hepatic glucose output lowering agents useful in the present methods include Glucophage and Glucophage XR.

In yet another embodiment, the antidiabetic agent is insulin, including all formulations of insulin, such as long acting and short acting forms of insulin.

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In another embodiment, the antidiabetic agent is a DPP-IV inhibitor.

Non-limiting examples of DPP-IV inhibitors useful in the present methods include sitagliptin, saxagliptin (Januvia™, Merck), denagliptin, vildagliptin (Galvus™, Novartis), alogliptin, alogliptin benzoate, ABT-279 and ABT-341 (Abbott), ALS-2-0426 (Alantos), ARI-2243 (Arisaph), BI-A and BI-B (Boehringer Ingelheim), SYR-322 (Takeda), MP-513 (Mitsubishi), DP-893 (Pfizer), RO-0730699 (Roche) or a combination of sitagliptin/metformin HCl (Janumet™, Merck).

In a further embodiment, the antidiabetic agent is a SGLT-2 inhibitor.

Non-limiting examples of SGLT-2 inhibitors useful in the present methods include dapagliflozin and sergliflozin, AVE2268 (Sanofi-Aventis) and T-1095 (Tanabe Seiyaku).

Non-limiting examples of antihypertensive agents useful in the present methods for treating a Condition include β-blockers and calcium channel blockers (for example diltiazem, verapamil, nifedipine, amlopidine, and mybef radii), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

In one embodiment, the antidiabetic agent is an agent that slows or blocks the breakdown of starches and certain sugars.

Non-limiting examples of antidiabetic agents that slow or block the breakdown of starches and certain sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in International Publication No. WO 00/07617.

Other specific additional therapeutic agents useful in the present methods for treating or preventing a Condition include, but are not limited to, rimonabant, 2-methyl-6-(phenylethynyl)-pyridine, 3[(2-methyl-1,4-thiazol-4-yl)ethynyl] pyridine, Melanotan-II, dexfenfluramine, fluoxetine, paroxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, aminone, milrinone, cilostamide, rolipram, cilomilast, phytanic acid, 4-[(E)-2-(5,6,7,8-tetramethyl-2-naphthalenyl)-1-propenyl]benzoic acid, retinoic acid, oleoyl-estrone, orlistat, lipstatin, tetrahydrolipstatin, teasaponin and diethylumbelliferyl phosphate.

In one embodiment, the present combination therapies for treating or preventing diabetes comprise administering a Bicyclic Piperidine and piperazine Derivative, an antidiabetic agent and/or an antiobesity agent.

In another embodiment, the present combination therapies for treating or preventing diabetes comprise administering a Bicyclic Piperidine and piperazine Derivative and an antidiabetic agent.

In another embodiment, the present combination therapies for treating or preventing diabetes comprise administering a Bicyclic Piperidine and piperazine Derivative and an anti-obesity agent.

In one embodiment, the present combination therapies for treating or preventing obesity comprise administering a Bicyclic Piperidine and piperazine Derivative, an antidiabetic agent and/or an antiobesity agent.

In another embodiment, the present combination therapies for treating or preventing obesity comprise administering a Bicyclic Piperidine and piperazine Derivative and an antidiabetic agent.

In another embodiment, the present combination therapies for treating or preventing obesity comprise administering a Bicyclic Piperidine and piperazine Derivative and an antiobesity agent.

In one embodiment, the present combination therapies for treating or preventing metabolic syndrome comprise administering a Bicyclic Piperidine and piperazine Derivative and one or more additional therapeutic agents selected from: antiobesity agents, antidiabetic agents, any agent useful for treating metabolic syndrome, any agent useful for treating a cardiovascular disease, cholesterol biosynthesis inhibitors, sterol absorption inhibitors, bile acid sequestrants, probucol derivatives. IBAT inhibitors, nicotinic acid receptor (NAR) agonists, ACAT inhibitors, cholesteryl ester transfer proten (CETP) inhibitors, low-density lipoprotein (LDL) activators, fish oil, water-soluble fibers, plant sterols, plant stanols and fatty acid esters of plant stanols.

In one embodiment, the additional therapeutic agent is a cholesterol biosynthesis inhibitor. In another embodiment, the cholesterol biosynthesis inhibitor is a squalene synthetase inhibitor. In another embodiment, the cholesterol biosynthesis inhibitor is a squalene epoxidase inhibitor. In still another embodiment, the cholesterol biosynthesis inhibitor is an HMG-CoA reductase inhibitor. In another embodiment, the HMG-CoA reductase inhibitor is a statin. In yet another embodiment, the statin is lovastatin, pravastatin, simvastatin or atorvastatin.

In one embodiment, the additional therapeutic agent is a cholesterol absorption inhibitor. In another embodiment, the cholesterol absorption inhibitor is ezetimibe.

In one embodiment, the additional therapeutic agent comprises a cholesterol absorption inhibitor and a cholesterol biosynthesis inhibitor. In another embodiment, the additional therapeutic agent comprises a cholesterol absorption inhibitor and a statin. In another embodiment, the additional therapeutic agent comprises ezetimibe and a statin. In another embodiment, the additional therapeutic agent comprises ezetimibe and simvastatin.

In one embodiment, the present combination therapies for treating or preventing metabolic syndrome comprise administering a Bicyclic Piperidine and piperazine Derivative, an antidiabetic agent and/or an antiobesity agent.

In another embodiment, the present combination therapies for treating or preventing metabolic syndrome comprise administering a Bicyclic Piperidine and piperazine Derivative and an antidiabetic agent.

In another embodiment, the present combination therapies for treating or preventing metabolic syndrome comprise administering a Bicyclic Piperidine and piperazine Derivative and an anti-obesity agent.

In one embodiment, the present combination therapies for treating or preventing a cardiovascular disease comprise administering one or more Bicyclic Piperidine and piperazine Derivatives, and an additional agent useful for treating or preventing a cardiovascular disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Bicyclic Piperidine and piperazine Derivatives are administered during a time when the additional therapeutic agent(s) exert their prophylactic or therapeutic effect, or vice versa.

In another embodiment, the one or more Bicyclic Piperidine and piperazine Derivatives and the additional therapeutic agent(s) are administered in doses commonly employed when such agents are used as monotherapy for treating a Condition.

In another embodiment, the one or more Bicyclic Piperidine and piperazine Derivatives and the additional therapeutic agent(s) are administered in doses lower than the doses commonly employed when such agents are used as monotherapy for treating a Condition.

In still another embodiment, the one or more Bicyclic Piperidine and piperazine Derivatives and the additional therapeutic agent(s) act synergistically and are administered in doses lower than the doses commonly employed when such agents are used as monotherapy for treating a Condition.

In one embodiment, the one or more Bicyclic Piperidine and piperazine Derivatives and the additional therapeutic agent(s) are present in the same composition. In one embodiment, this composition is suitable for oral administration. In another embodiment, this composition is suitable for intravenous administration.

The one or more Bicyclic Piperidine and piperazine Derivatives and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Bicyclic Piperidine and piperazine Derivatives and the additional therapeutic agent(s) may inhibit the resistance of a Condition to these agents.

In one embodiment, when the patient is treated for diabetes or a diabetic complication, the additional therapeutic agent is an antidiabetic agent which is not a Bicyclic Piperidine and piperazine Derivative. In another embodiment, the additional therapeutic agent is an agent useful for reducing any potential side effect of a Bicyclic Piperidine and piperazine Derivative. Such potential side effects include, but are not limited to, nausea, vomiting, headache, fever, lethargy, muscle aches, diarrhea, general pain, and pain at an injection site.

In one embodiment, the additional therapeutic agent is used at its known therapeutically effective dose. In another embodiment, the additional therapeutic agent is used at its normally prescribed dosage. In another embodiment, the additional therapeutic agent is used at less than its normally prescribed dosage or its known therapeutically effective dose.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Bicyclic Piperidine and piperazine Derivative(s) and the other agent(s) for treating diseases or conditions listed above can be administered simultaneously or sequentially. This particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Bicyclic Piperidine and piperazine Derivatives and the additional therapeutic agent(s) can when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

Compositions and Administration

In one embodiment, the invention provides compositions comprising an effective amount of one or more Bicyclic Piperidine and piperazine Derivatives or a pharmaceutically acceptable salt, solvate, ester, prodrug or stereoisomer thereof, and a pharmaceutically acceptable carrier.

For preparing compositions comprising one or more Bicyclic Piperidine and piperazine Derivatives, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, a Bicyclic Piperidine and piperazine Derivative is administered orally.

In another embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation is from about 0.1 to about 2000 mg. Variations will necessarily occur depending on the target of the therapy, the patient and the route of administration. In one embodiment, the unit dose dosage is from about 0.2 to about 1000 mg. In another embodiment, the unit dose dosage is from about 1 to about 500 mg. In another embodiment, the unit dose dosage is from about 1 to about 100 mg/day. In still another embodiment, the unit dose dosage is from about 1 to about 50 mg. In yet another embodiment, the unit dose dosage is from about 1 to about 10 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, the condition and size of the patient, as well as severity of the symptoms being treated. A typical recommended daily dosage regimen for oral administration can range from about 1 mg/day to about 1000 mg/day, 1 mg/day to about 500 mg/day, 1 mg/day to about 300 mg/day, 1 mg/day to about 75 mg/day, 1 mg/day to about 50 mg/day, or 1 mg/day to about 20 mg/day, in one dose or in two to four divided doses.

When the invention comprises a combination of one or more Bicyclic Piperidine and piperazine Derivatives and an additional therapeutic agent, the two active components may be co-administered simultaneously or sequentially, or a single composition comprising one or more Bicyclic Piperidine and piperazine Derivatives and the additional therapeutic agent(s) in a pharmaceutically acceptable carrier can be administered. The components of the combination can be administered individually or together in any conventional dosage form such as capsule, tablet, powder, cachet, suspension, solution, suppository, nasal spray, etc. The dosage of the additional therapeutic agent can be determined from published material, and may range from about 1 to about 1000 mg per dose. In one embodiment, when used in combination, the dosage levels of the individual components are lower than the recommended individual dosages because of an advantageous effect of the combination.

In one embodiment, the components of a combination therapy regimen are to be administered simultaneously, they can be administered in a single composition with a pharmaceutically acceptable carrier.

In another embodiment, when the components of a combination therapy regimen are to be administered separately or sequentially, they can be administered in separate compositions, each containing a pharmaceutically acceptable carrier.

Kits

In one aspect, the present invention provides a kit comprising an effective amount of one or more Bicyclic Piperidine and piperazine Derivatives, or a pharmaceutically acceptable salt, solvate, ester, prodrug or stereoisomer thereof, and a pharmaceutically acceptable carrier.

In another aspect the present invention provides a kit comprising an amount of one or more Bicyclic Piperidine and piperazine Derivatives, or a pharmaceutically acceptable salt, solvate, ester, prodrug or stereoisomer thereof, and an amount of one or more additional therapeutic agents listed above, wherein the combined amounts are effective for treating or preventing a Condition in a patient.

When the components of a combination therapy regimen are to be administered in more than one composition, they can be provided in a kit comprising a single package containing one or more containers, wherein one container contains one or more Bicyclic Piperidine and piperazine Derivatives in a pharmaceutically acceptable carrier, and a second, separate container comprises an additional therapeutic agent in a pharmaceutically acceptable carrier, with the active components of each composition being present in amounts such that the combination is therapeutically effective.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula:

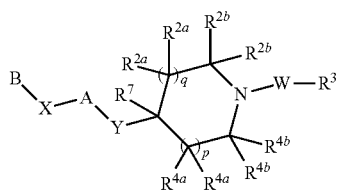

(I)

or a pharmaceutically acceptable salt or stereoisomer thereof, wherein:

A is aryl or -5- or 6-membered heteroaryl, wherein said aryl group or said -5- or 6-membered heteroaryl group can be optionally substituted with up to 4 groups, which can be the same or different, and are selected from alkyl, aryl, alkenyl, cycloalkyl, cycloalkenyl, haloalkyl, hydroxyalkyl, halo, —OH, —O-haloalkyl, —O-alkyl, —O-alkyl-OH, —O-alkyl-O-alkyl, —O-aryl, -alkylene-O-alkyl, —CN, —N($R^4$)$_2$, —C(O)H, —C(O)$R^4$, —C(O)O$R^4$, —C(O)N($R^4$)$_2$, —NHC(O)$R^4$, —NHS(O)$_m$$R^4$, —S(O)$_n$$R^4$ and —S(O)$_m$N($R^4$)$_2$;

B is aryl or heteroaryl, wherein said aryl group or said heteroaryl group can be the same or different, and are selected from alkyl, aryl, alkenyl, cycloalkyl, cycloalkenyl, haloalkyl, hydroxyalkyl, heteroaryl, halo, —OH, —O-haloalkyl, —O-alkyl, —O-aryl, -alkylene-O-alkyl, -alkylene-S(O)$_2$-alkyl, —CN, —N($R^4$)$_2$, —C(O)$R^4$, —C(O)O$R^4$, —C(O)N($R^4$)$_2$, —NHC(O)$R^4$, —NHS(O)$_m$$R^4$, —S(O)$_n$$R^4$ and —S(O)$_m$N($R^4$)$_2$, wherein said cycloalkyl or said heteroaryl substituent group can be unsubstituted or optionally substituted with $R^9$, and wherein when B is aryl, the aryl group can be optionally fused to a 4 to 7-membered cycloalkyl group or cycloalkanoyl group;

W is —C(O)O—, alkylene, —C(O)—, —C(O)—O—, —S(O)$_2$—, —S(O)$_2$—N($R^7$)— or —C(O)—N($R^7$)—;

X is —C($R^1$)$_2$—, —O—, —N($R^{10}$)— or —S—;

Y is a bond, alkylene, -(alkylene)$_r$-O-(alkylene)$_r$-, -(alkylene)$_r$-N($R^{12}$)-(alkylene)$_r$- or -(alkylene)$_r$-S-(alkylene)$_r$-;

Z is C($R^7$);

each occurrence of $R^1$ is independently H, alkyl, cycloalkyl, halo or —O$R^7$; wherein said alkyl group can be unsubstituted or optionally substituted with one or more of the following groups: —O-alkyl, —OH or —N($R^4$)$_2$; and wherein any two geminal $R^1$ groups, together with the common carbon atom to which they are attached, can join to form a spirocyclic 3- to 6-membered cycloalkyl group, a spirocyclic 3- to 6-membered heterocycloalkyl group or a spirocyclic 3- to 6-membered heterocycloalkenyl group; and wherein any two $R^1$ groups present on separate ring carbon atoms can join to form a cycloalkyl or heterocycloalkyl bridge; and wherein any particular $R^1$ group is —OH, then any other $R^1$ group attached to the same carbon atom must be other than halo or —O$R^7$;

each occurrence of $R^{2a}$ is H or alkyl, wherein: (i) any two $R^{2a}$ groups, together with the carbon atoms to which each are attached, can join to form a cycloalkyl or heterocycloalkyl group; (ii) an $R^{2a}$ group and an $R^{2b}$ group, together with the carbon atoms to which each are attached, can join to form a cycloalkyl or heterocycloalkyl group; or (iii) $R^7$ and an $R^{2a}$ group that is attached to a carbon atom adjacent to Z, together with the carbon atoms to which each are attached, can join to form a cycloalkyl or heterocycloalkyl group;

each occurrence of $R^{2b}$ is H or alkyl, wherein (i): any two $R^{2b}$ groups, together with the carbon atoms to which each are attached, can join to form a cycloalkyl or heterocycloalkyl group; or (ii) an $R^{2b}$ group and an $R^{2a}$ group, together with the carbon atoms to which each are attached, can join to form a cycloalkyl or heterocycloalkyl group;

$R^3$ is alkyl, alkenyl, alkynyl, haloalkyl, -alkylene-O-(alkylene)$_r$-aryl, -alkylene-S-aryl, -alkylene-N($R^4$)C(O)O-alkyl, —CH(cycloalkyl)$_2$, —CH(heterocycloalkyl)$_2$, -(alkylene)$_r$-aryl, -(alkylene)$_r$-cycloalkyl, -(alkylene)$_r$-cycloalkenyl, -(alkylene)$_r$-heterocycloalkyl, -(alkylene)$_r$-heterocycloalkenyl or -(alkylene)$_r$-heteroaryl, wherein said aryl, cycloalkyl, cycloalkenyl, heterocycloalkyl, heterocycloalkenyl or heteroaryl groups can be unsubstituted or optionally substituted with $R^8$;

each occurrence of $R^4$ is H, alkyl, cycloalkyl or -(alkylene)$_r$-alkenyl, wherein said alkyl group can be optionally substituted with halo, —OH or —O-alkyl;

each occurrence of $R^{4a}$ is H or alkyl, wherein (i) any two $R^{4a}$ groups, together with the carbon atoms to which each are attached, can join to form a cycloalkyl or heterocycloalkyl group, (ii) an $R^{4a}$ group and an $R^{4b}$ group, together with the carbon atoms to which each are attached, can join to form a cycloalkyl or heterocycloalkyl group, or (iii) $R^7$ and an $R^{4a}$ group that is attached to a carbon atom adjacent to Z, together with the carbon atoms to which each are attached, can join to form a cycloalkyl or heterocycloalkyl group;

each occurrence of $R^{4b}$ is H or alkyl, wherein (i) any two $R^{4b}$ groups, together with the carbon atoms to which each are attached, can join to form a cycloalkyl or heterocycloalkyl group, or (ii) an $R^{4b}$ group and an $R^{4a}$ group, together with the carbon atoms to which each are attached, can join to form a cycloalkyl or heterocycloalkyl group;

R$^7$ is H or alkyl, or: (i) R$^7$ and an R$^{2a}$ group that is attached to a carbon atom adjacent to Z, together with the carbon atoms to which each are attached, can join to form a cycloalkyl or heterocycloalkyl group, or (ii) R$^7$ and an R$^{4a}$ group that is attached to a carbon atom adjacent to Z, together with the carbon atoms to which each are attached, can join to form a cycloalkyl or heterocycloalkyl group;

R$^8$ is aryl, heteroaryl, heterocycloalkenyl, cycloalkenyl, cycloalkyl or heterocycloalkyl, any of which can be optionally substituted with R$^9$;

R$^9$ represents from 1 to 4 optional substituents, which can be the same or different, and which are selected from alkyl, alkenyl, alkynyl, halo, haloalkyl, —CN, —NO$_2$, —O-(alkylene)$_t$-R$^{13}$, —S-(alkylene)$_t$-R$^{13}$, —N(R$^{13}$)-(alkylene)$_t$-R$^{13}$, -(alkylene)$_t$-R$^{13}$, —C(O)-(alkylene)$_t$-R$^{13}$, —C(O)O-(alkylene)$_t$-R$^{13}$, —N(R$^7$)C(O)-(alkylene)$_t$-R$^{13}$, —C(O)N(R$^7$)-(alkylene)$_t$-R$^{13}$, —OC(O)-(alkylene)$_t$-R$^{13}$, —N(R$^7$)C(O)N(R$^7$)-(alkylene)$_t$-R$^{13}$, —N(R$^7$)C(O)O-(alkylene)$_t$-R$^{13}$, —S(O)-(alkylene)$_t$-R$^{13}$ or —S(O)$_2$(alkylene)$_t$-R$^{13}$;

R$^{10}$ is H, alkyl, aryl, or —C(O)OR$^4$, wherein said alkyl group is unsubstituted or optionally substituted with —OH or —O-alkyl;

R$^{12}$ is H, alkyl or aryl;

each occurrence of R$^{13}$ is independently H, haloalkyl, aryl, cycloalkyl, cycloalkenyl, heterocycloalkyl, heterocycloalkenyl or heteroaryl;

each occurrence of m is independently 1 or 2;

each occurrence of n is independently 0, 1 or 2, such that the sum of n and m is an integer ranging from 0 to 4;

p is an integer ranging from 0 to 4;

q is an integer ranging from 0 to 4; and each occurrence of t is independently 0 or 1, such that (i) at least one of R$^{2a}$, R$^{2b}$, R$^{4a}$ or R$^{4b}$, and the carbon atom to which it is attached, must combine with a separate R$^{2a}$, R$^{2b}$, R$^{4a}$ or R$^{4b}$ group and the carbon atom to which it is attached, to form a cycloalkyl or heterocycloalkyl group, or (ii) R$^7$ and an R$^{2a}$ group that is attached to a carbon atom adjacent to Z, together with the carbon atoms to which each are attached, must combine to form a cycloalkyl or heterocycloalkyl group, or (iii) R$^7$ and an R$^{4a}$ group that is attached to a carbon atom adjacent to Z, together with the carbon atoms to which each are attached, must combine to form a cycloalkyl or heterocycloalkyl group.

2. The compound of claim 1, wherein A and B are each independently aryl or 5- or 6-membered heteroaryl.

3. The compound of claim 1, wherein Y is —O— or —NH—, and the group B—X-A- is:

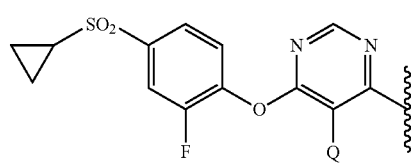

-continued

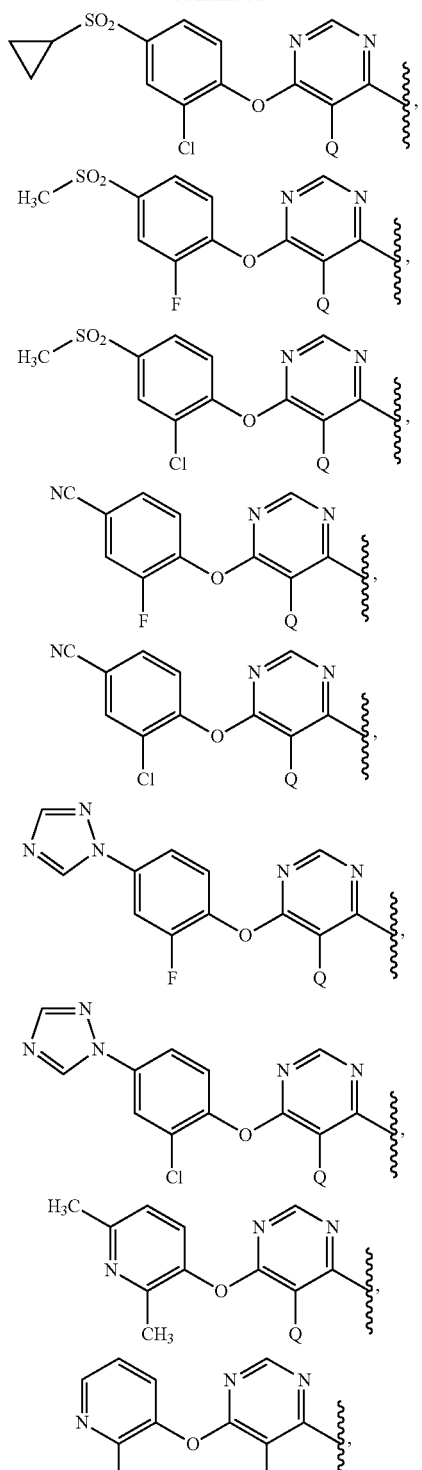

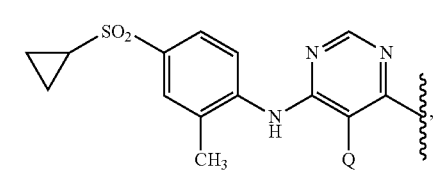

-continued
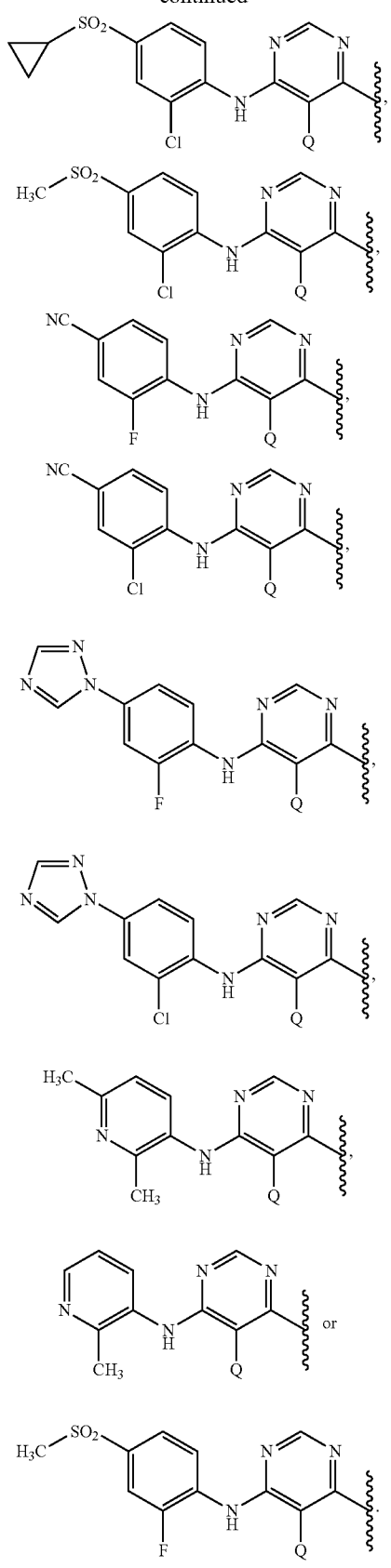
wherein Q is H, halo, alkyl or —O-alkyl.
4. The compound of claim 1, wherein the group B—X-A- is:
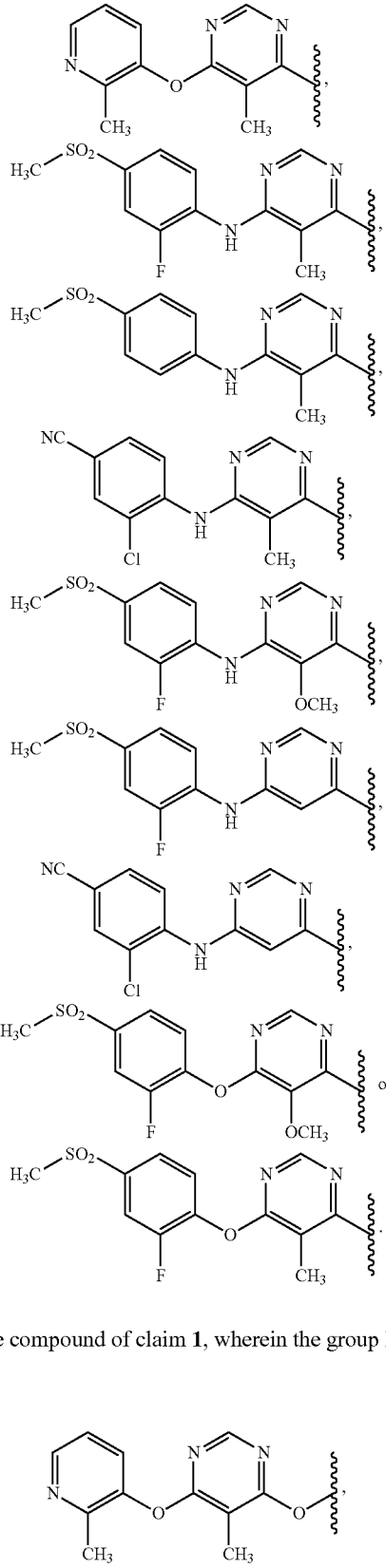
5. The compound of claim 1, wherein the group B—X-A-Y— is:

-continued
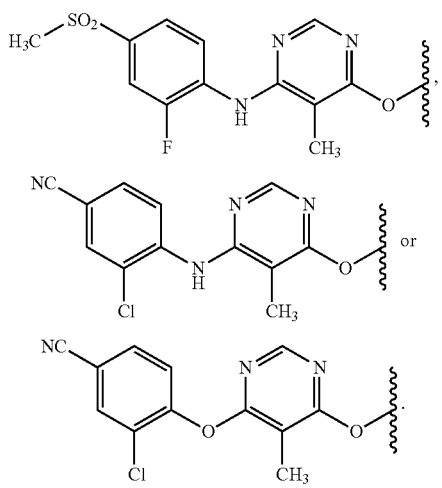
6. The compound of claim 1, wherein the group:
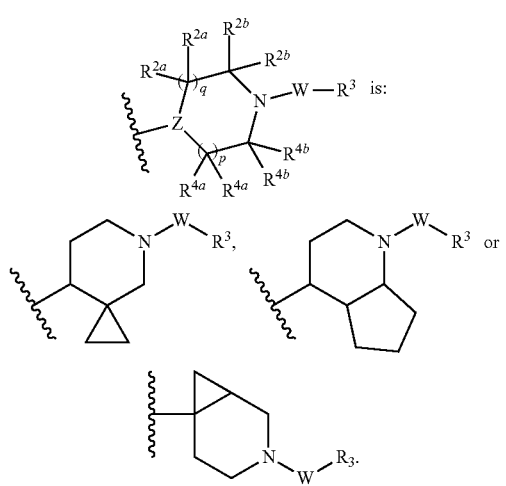
7. The compound of claim 3, wherein the group:
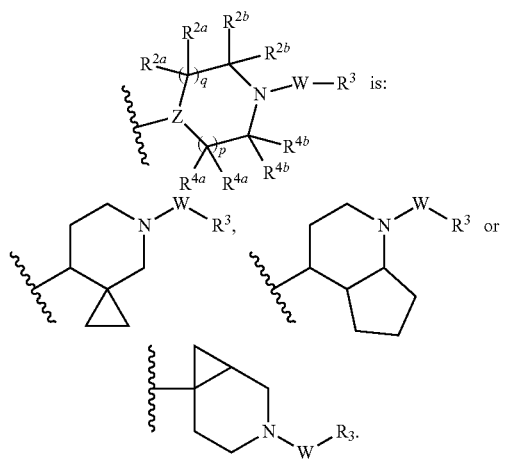
8. A compound having the structure:
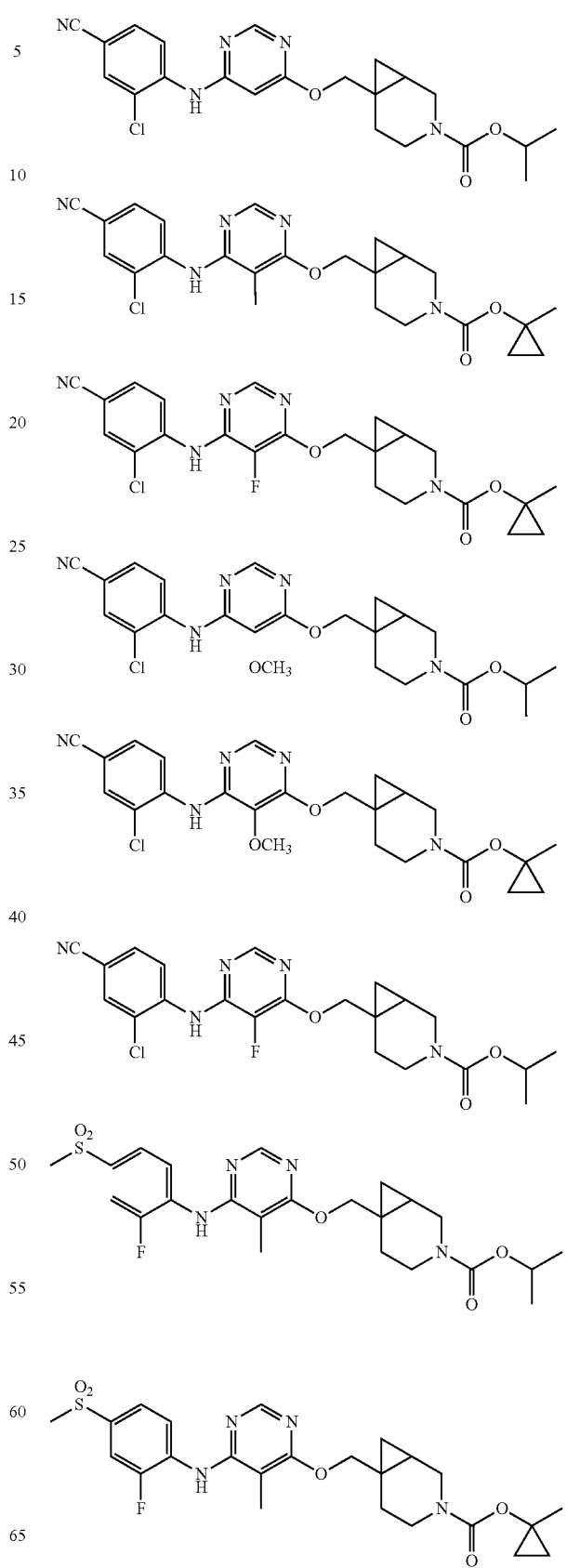

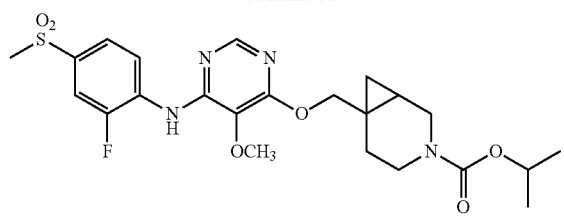
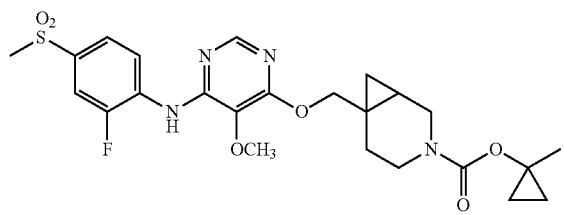
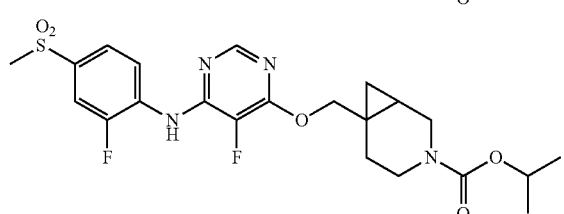
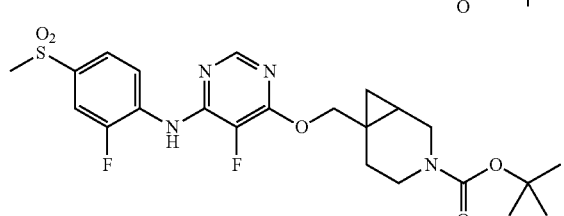
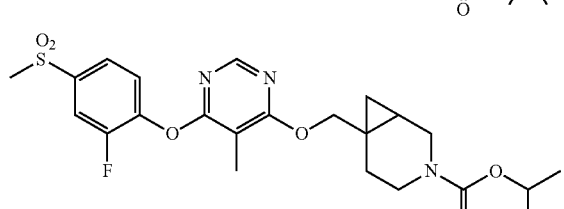
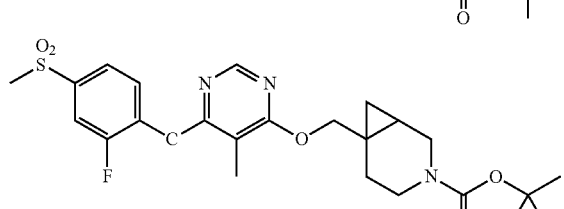
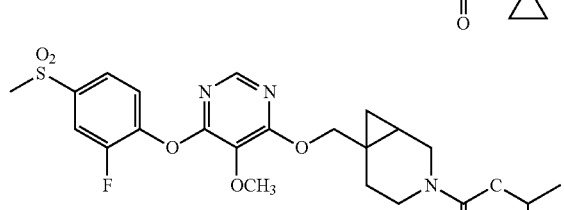
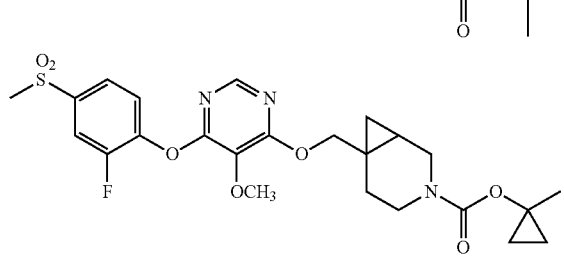
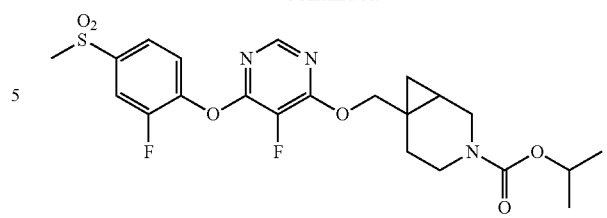
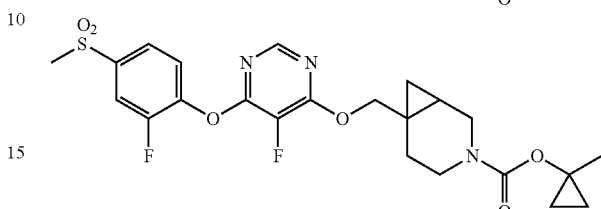
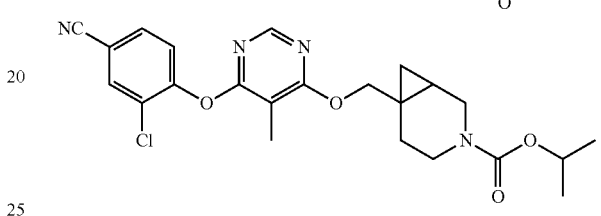
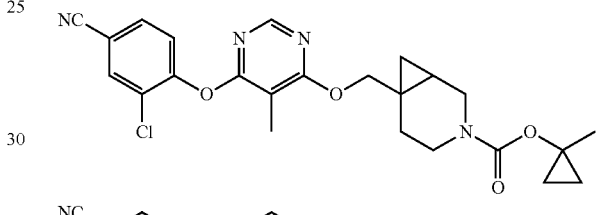
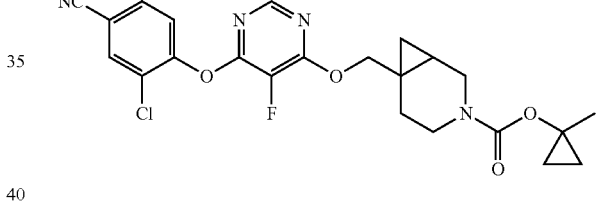
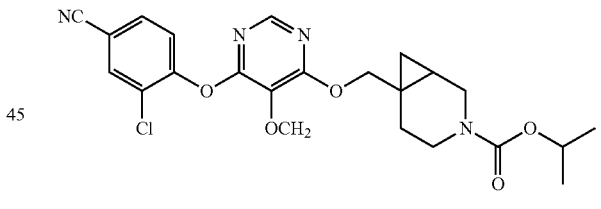
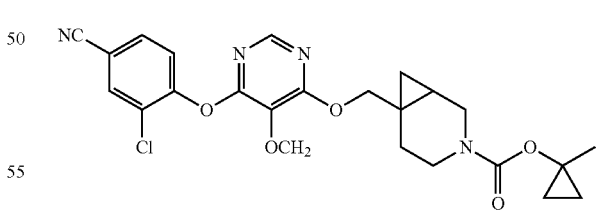
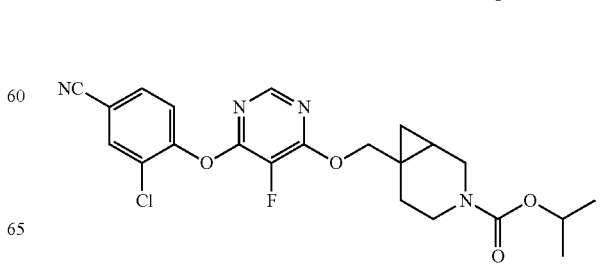

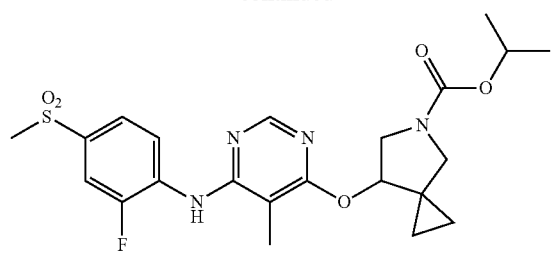
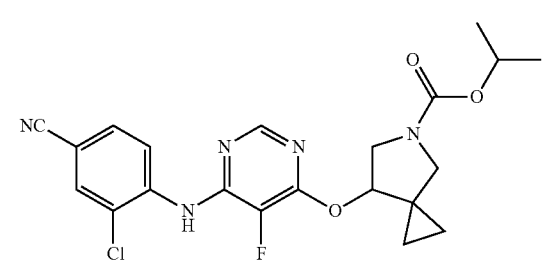
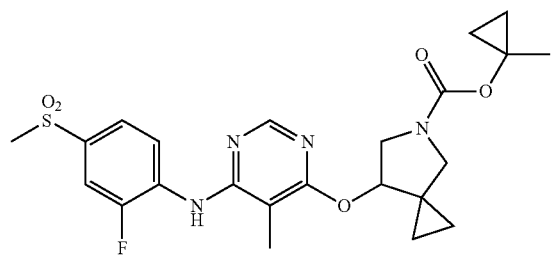
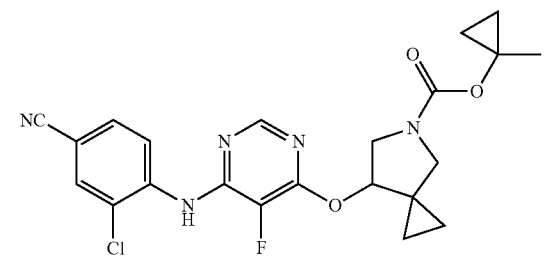
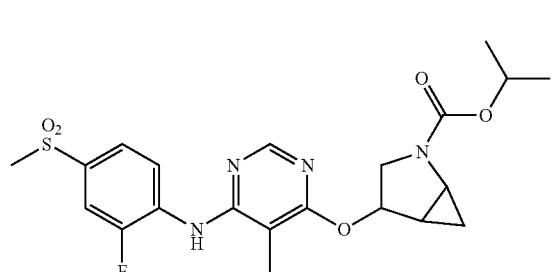
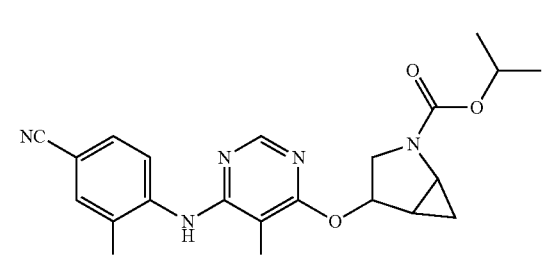
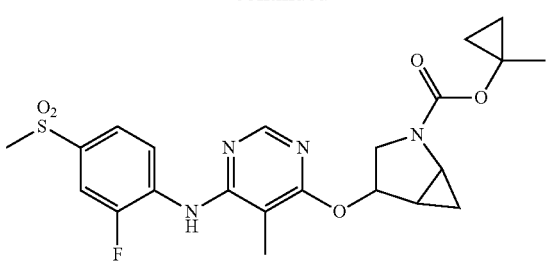
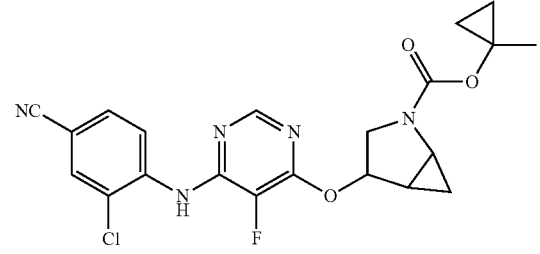
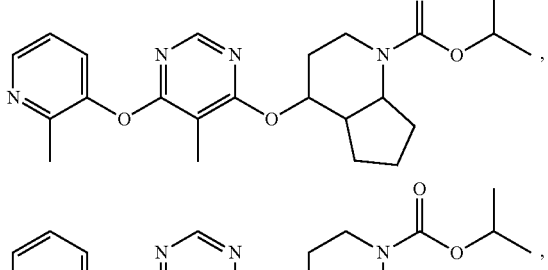
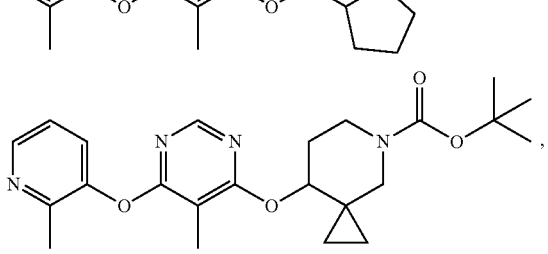
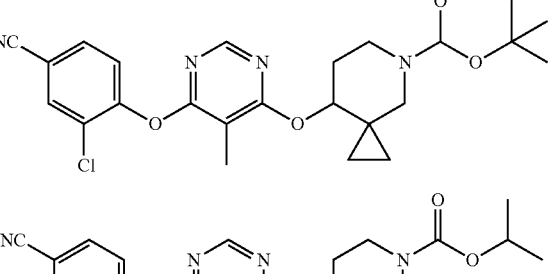
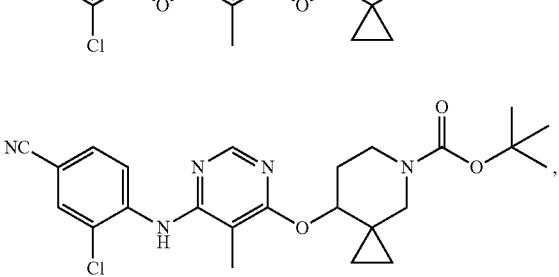

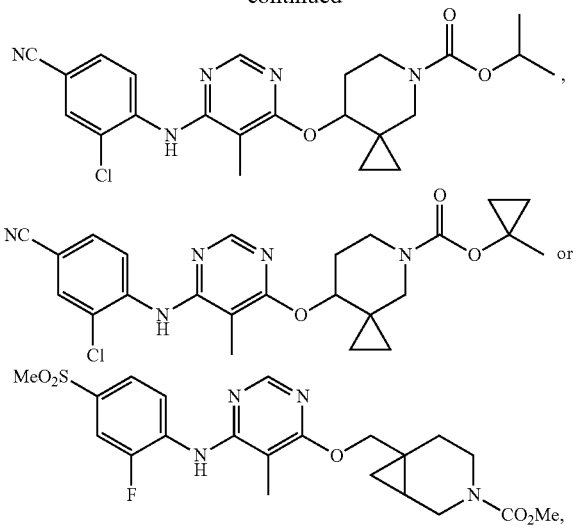

or a pharmaceutically acceptable salt or stereoisomer thereof.

9. A composition comprising an effective amount of one or more compounds of claim 1 or a pharmaceutically acceptable salt or stereoisomer thereof, and at least one pharmaceutically acceptable carrier.

10. The composition of claim 9, further comprising an effective amount of one or more additional therapeutic agents, wherein the additional therapeutic agents are selected from antidiabetic agents and antiobesity agents.

11. The composition of claim 10, wherein the antidiabetic agents are selected from an insulin sensitizer, an α-glucosidase inhibitor, a DPP-IV inhibitor, an insulin secretagogue, an hepatic glucose output lowering compound, an antihypertensive agent, a sodium glucose uptake transporter 2 (SGLT-2) inhibitor, insulin and an insulin-containing composition.

12. The composition of claim 10, wherein the antiobesity agents are selected from a neuropeptide Y antagonist, an MCR4 agonist, an MCH receptor antagonist, a protein hormone, an AMP kinase activator, a CB1 antagonist, a GLP-1 agonist and a lipase inhibitor.

13. A method for treating diabetes, obesity or metabolic syndrome in a patient, the method comprising administering to the patient an effective amount of one or more compounds of claim 1 or a pharmaceutically acceptable salt or stereoisomer thereof.

14. The method of claim 13, wherein the treating is for diabetes.

15. The method of claim 14, wherein the treating is for type II diabetes.

16. The method of claim 13, wherein the treating is for obesity.

17. The method of claim 13, further comprising administering an effective amount of one or more additional therapeutic agents, wherein the additional therapeutic agents are selected from antidiabetic agents and antiobesity agents.

* * * * *